United States Patent
Michal et al.

(10) Patent No.: US 7,641,643 B2
(45) Date of Patent: Jan. 5, 2010

(54) METHODS AND COMPOSITIONS TO TREAT MYOCARDIAL CONDITIONS

(75) Inventors: Eugene T. Michal, San Francisco, CA (US); Evgenia Mandrusov, Campbell, CA (US); Charles D. Claude, Santa Clara, CA (US); Nadine Ding, San Jose, CA (US); Murthy Simhambhatla, San Jose, CA (US); Syed Faiyez Ahmed Hossainy, Fremont, CA (US); Srinivasan Sridharan, Morgan Hill, CA (US); Paul Consigny, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1146 days.

(21) Appl. No.: 10/414,767

(22) Filed: Apr. 15, 2003

(65) Prior Publication Data
US 2004/0213756 A1    Oct. 28, 2004

(51) Int. Cl.
*A61M 31/00* (2006.01)
(52) U.S. Cl. .................................................. 604/500
(58) Field of Classification Search ................ 604/524, 604/264; 424/93.1; 435/325, 326, 173.1; 607/50, 2, 3; 623/1.41, 3.1
See application file for complete search history.

(56) References Cited

U.S. PATENT DOCUMENTS

| | | | |
|---|---|---|---|
| 3,780,733 A | 12/1973 | Martinez-Manzor | |
| 4,617,186 A | 10/1986 | Schafer et al. | |
| 4,794,931 A | 1/1989 | Yock | |
| 4,818,291 A | 4/1989 | Iwatsuki et al. | |
| 5,000,185 A | 3/1991 | Yock | |
| 5,024,234 A | 6/1991 | Leary et al. | |
| 5,049,130 A | 9/1991 | Powell | |
| 5,092,848 A | 3/1992 | DeCiutiis | |
| 5,100,185 A | 3/1992 | Menke et al. | |

(Continued)

FOREIGN PATENT DOCUMENTS

EP      0331584      9/1989

(Continued)

OTHER PUBLICATIONS

Hutcheson et al. "Comparison of Benefits on Myocardial Performance of Cellular Cardiomyoplasty with Skeletal Myoblasts and Fibroblasts" Cell Transplant 2000 9(3).

(Continued)

*Primary Examiner*—Manuel A Mendez
(74) *Attorney, Agent, or Firm*—Blakely Sokoloff Taylor & Taylor LLP

(57) ABSTRACT

Methods, devices, kits and compositions to treat a myocardial infarction. In one embodiment, the method includes the prevention of remodeling of the infarct zone of the ventricle. In other embodiments, the method includes the introduction of structurally reinforcing agents. In other embodiments, agents are introduced into a ventricle to increase compliance of the ventricle. In an alternative embodiment, the prevention of remodeling includes the prevention of thinning of the ventricular infarct zone. In another embodiment, the prevention of remodeling and thinning of the infarct zone involves the cross-linking of collagen and prevention of collagen slipping. In other embodiments, the structurally reinforcing agent may be accompanied by other therapeutic agents. These agents may include but are not limited to pro-fibroblastic and angiogenic agents.

34 Claims, 35 Drawing Sheets

U.S. PATENT DOCUMENTS

| | | | |
|---|---|---|---|
| 5,128,326 A | 7/1992 | Balazs et al. | |
| 5,171,217 A | 12/1992 | March et al. | |
| 5,202,745 A | 4/1993 | Sorin et al. | |
| 5,203,338 A | 4/1993 | Jang | |
| 5,270,300 A | 12/1993 | Hunziker | |
| 5,291,267 A | 3/1994 | Sorin et al. | |
| 5,306,250 A | 4/1994 | March et al. | |
| 5,321,501 A | 6/1994 | Swanson et al. | |
| 5,328,955 A | 7/1994 | Rhee et al. | |
| 5,336,252 A | 8/1994 | Cohen | |
| 5,354,279 A | 10/1994 | Hofling | |
| 5,365,325 A | 11/1994 | Kumasaka et al. | |
| 5,372,138 A | 12/1994 | Crowley et al. | |
| 5,380,292 A | 1/1995 | Wilson | |
| 5,437,632 A | 8/1995 | Engelson | |
| 5,455,039 A | 10/1995 | Edelman et al. | |
| 5,459,570 A | 10/1995 | Swanson et al. | |
| 5,464,395 A | 11/1995 | Faxon et al. | |
| 5,465,147 A | 11/1995 | Swanson | |
| 5,485,486 A | 1/1996 | Gilhousen et al. | |
| 5,499,630 A | 3/1996 | Hiki et al. | |
| 5,540,912 A | 7/1996 | Roorda et al. | |
| 5,546,948 A | 8/1996 | Hamm et al. | |
| 5,575,815 A | 11/1996 | Slepian et al. | |
| 5,580,714 A | 12/1996 | Polovina | |
| 5,580,856 A | 12/1996 | Prestrelski et al. | |
| 5,588,432 A | 12/1996 | Crowley | |
| 5,621,610 A | 4/1997 | Moore et al. | |
| 5,642,234 A | 6/1997 | Altman et al. | |
| 5,655,548 A | 8/1997 | Nelson et al. | |
| 5,667,778 A | 9/1997 | Atala | |
| 5,693,029 A | 12/1997 | Leonhardt | |
| 5,722,403 A | 3/1998 | McGee et al. | |
| 5,740,808 A | 4/1998 | Panescu et al. | |
| 5,785,689 A | 7/1998 | De Toledo et al. | |
| 5,811,533 A | 9/1998 | Gold et al. | |
| 5,827,313 A | 10/1998 | Ream et al. | |
| 5,843,156 A | 12/1998 | Slepian et al. | |
| 5,874,500 A | 2/1999 | Rhee et al. | |
| 5,879,713 A | 3/1999 | Roth et al. | |
| 5,900,433 A | 5/1999 | Igo et al. | |
| 5,919,449 A | 7/1999 | Dinsmore | |
| 5,935,160 A | 8/1999 | Auricchio et al. | |
| 5,939,323 A | 8/1999 | Valentini et al. | |
| 5,941,868 A | 8/1999 | Kaplan et al. | |
| 5,957,941 A | 9/1999 | Ream | |
| 5,968,064 A | 10/1999 | Selmon | |
| 5,979,449 A | 11/1999 | Steer | |
| 5,981,568 A | 11/1999 | Kunz et al. | |
| 5,984,908 A * | 11/1999 | Davis et al. | 604/524 |
| 5,997,536 A | 12/1999 | Osswald et al. | |
| 6,022,540 A | 2/2000 | Bruder et al. | |
| 6,045,565 A | 4/2000 | Ellis et al. | |
| 6,051,071 A | 4/2000 | Charvet et al. | |
| 6,051,648 A | 4/2000 | Rhee et al. | |
| 6,056,744 A | 5/2000 | Edwards | |
| 6,058,329 A | 5/2000 | Salo et al. | |
| 6,060,053 A | 5/2000 | Atala | |
| 6,071,305 A | 6/2000 | Brown et al. | |
| 6,086,582 A | 7/2000 | Altman et al. | |
| 6,093,177 A | 7/2000 | Javier, Jr. et al. | |
| 6,099,563 A | 8/2000 | Zhong | |
| 6,099,864 A | 8/2000 | Morrison et al. | |
| 6,102,887 A | 8/2000 | Altman | |
| 6,102,904 A | 8/2000 | Vigil et al. | |
| 6,102,926 A | 8/2000 | Tartaglia et al. | |
| 6,120,520 A | 9/2000 | Saadat et al. | |
| 6,120,904 A | 9/2000 | Hostettler et al. | |
| 6,127,448 A | 10/2000 | Domb | |
| 6,133,231 A | 10/2000 | Ferrara et al. | |
| 6,134,003 A | 10/2000 | Tearney et al. | |
| 6,151,525 A * | 11/2000 | Soykan et al. | 607/50 |
| 6,152,141 A | 11/2000 | Stevens et al. | |
| 6,153,428 A | 11/2000 | Gustafsson et al. | |
| 6,159,443 A | 12/2000 | Hallahan et al. | |
| 6,175,669 B1 | 1/2001 | Colston et al. | |
| 6,177,407 B1 | 1/2001 | Rodgers et al. | |
| 6,179,809 B1 | 1/2001 | Khairkhahan et al. | |
| 6,183,432 B1 | 2/2001 | Milo | |
| 6,183,444 B1 | 2/2001 | Glines et al. | |
| 6,187,330 B1 | 2/2001 | Wang et al. | |
| 6,190,353 B1 | 2/2001 | Makower et al. | |
| 6,191,144 B1 | 2/2001 | Isner | |
| 6,193,763 B1 | 2/2001 | Mackin | |
| 6,197,324 B1 | 3/2001 | Crittenden | |
| 6,201,608 B1 | 3/2001 | Mandella et al. | |
| 6,206,893 B1 | 3/2001 | Klein et al. | |
| 6,206,914 B1 | 3/2001 | Soykan et al. | |
| 6,207,180 B1 | 3/2001 | Ottoboni et al. | |
| 6,210,392 B1 | 4/2001 | Vigil et al. | |
| 6,217,527 B1 | 4/2001 | Selmon et al. | |
| 6,217,554 B1 | 4/2001 | Green | |
| 6,221,049 B1 | 4/2001 | Selmon et al. | |
| 6,231,546 B1 | 5/2001 | Milo et al. | |
| 6,235,000 B1 | 5/2001 | Milo et al. | |
| 6,241,710 B1 | 6/2001 | Van et al. | |
| 6,251,104 B1 | 6/2001 | Kesten et al. | |
| 6,283,947 B1 | 9/2001 | Mirzaee | |
| 6,287,285 B1 | 9/2001 | Michal et al. | |
| 6,290,729 B1 | 9/2001 | Slepian et al. | |
| 6,296,602 B1 | 10/2001 | Headley | |
| 6,299,604 B1 | 10/2001 | Ragheb et al. | |
| 6,309,370 B1 | 10/2001 | Haim et al. | |
| 6,312,725 B1 | 11/2001 | Wallace et al. | |
| 6,315,994 B2 | 11/2001 | Usala et al. | |
| 6,323,278 B2 | 11/2001 | Rhee et al. | |
| RE37,463 E | 12/2001 | Altman | |
| 6,328,229 B1 | 12/2001 | Duronio et al. | |
| 6,333,194 B1 | 12/2001 | Levy et al. | |
| 6,334,872 B1 | 1/2002 | Termin et al. | |
| 6,346,098 B1 | 2/2002 | Yock et al. | |
| 6,346,099 B1 | 2/2002 | Altman | |
| 6,346,515 B1 | 2/2002 | Pitaru et al. | |
| 6,358,247 B1 | 3/2002 | Altman et al. | |
| 6,358,258 B1 | 3/2002 | Arcia et al. | |
| 6,368,285 B1 | 4/2002 | Osadchy et al. | |
| 6,371,935 B1 | 4/2002 | Macoviak et al. | |
| 6,371,992 B1 | 4/2002 | Tanagho et al. | |
| 6,379,379 B1 | 4/2002 | Wang | |
| 6,385,476 B1 | 5/2002 | Osadchy et al. | |
| 6,391,052 B2 | 5/2002 | Buirge et al. | |
| 6,395,023 B1 | 5/2002 | Summers | |
| 6,409,716 B1 | 6/2002 | Sahatjian et al. | |
| 6,416,510 B1 | 7/2002 | Altman et al. | |
| 6,432,119 B1 | 8/2002 | Saadat | |
| 6,436,135 B1 | 8/2002 | Goldfarb | |
| 6,443,941 B1 | 9/2002 | Slepian et al. | |
| 6,443,949 B2 | 9/2002 | Altman | |
| 6,447,504 B1 | 9/2002 | Ben-Haim et al. | |
| 6,458,095 B1 | 10/2002 | Wirt et al. | |
| 6,458,098 B1 | 10/2002 | Kanesaka | |
| 6,464,862 B2 | 10/2002 | Bennett et al. | |
| 6,465,001 B1 | 10/2002 | Hubbell et al. | |
| 6,478,776 B1 | 11/2002 | Rosenman et al. | |
| 6,482,231 B1 | 11/2002 | Abatangelo et al. | |
| 6,485,481 B1 | 11/2002 | Pfeiffer | |
| 6,494,862 B1 | 12/2002 | Ray et al. | |
| 6,548,081 B2 | 4/2003 | Sadozai et al. | |
| 6,554,801 B1 | 4/2003 | Steward et al. | |
| 6,599,267 B1 | 7/2003 | Ray et al. | |
| 6,624,245 B2 | 9/2003 | Wallace et al. | |
| 6,628,988 B2 | 9/2003 | Kramer et al. | |
| 6,629,947 B1 | 10/2003 | Sahatjian et al. | |
| 6,632,457 B1 | 10/2003 | Sawhney | |

| | | | |
|---|---|---|---|
| 6,635,267 B1 | 10/2003 | Miyoshi et al. | |
| 6,660,034 B1 | 12/2003 | Mandrusov et al. | |
| 6,682,730 B2 | 1/2004 | Mickel et al. | |
| 6,689,608 B1 | 2/2004 | Mikos et al. | |
| 6,692,466 B1 | 2/2004 | Chow et al. | |
| 6,702,744 B2 | 3/2004 | Mandrusov et al. | |
| 6,706,034 B1 | 3/2004 | Bhat | |
| 6,737,072 B1 | 5/2004 | Angele et al. | |
| 6,748,258 B1 | 6/2004 | Mueller et al. | |
| 6,749,617 B1 | 6/2004 | Palasis et al. | |
| 6,759,431 B2 * | 7/2004 | Hunter et al. | 514/449 |
| 6,777,231 B1 | 8/2004 | Katz et al. | |
| 6,790,455 B2 | 9/2004 | Chu et al. | |
| 6,858,229 B1 | 2/2005 | Hubbell et al. | |
| 6,916,648 B2 * | 7/2005 | Goddard et al. | 435/252.3 |
| 6,992,172 B1 | 1/2006 | Chang et al. | |
| 7,112,587 B2 | 9/2006 | Timmer et al. | |
| 7,129,210 B2 | 10/2006 | Lowinger et al. | |
| 2001/0023349 A1 | 9/2001 | VanTassel et al. | |
| 2002/0013408 A1 | 1/2002 | Rhee et al. | |
| 2002/0042473 A1 | 4/2002 | Trollsas et al. | |
| 2002/0072706 A1 | 6/2002 | Hiblar et al. | |
| 2002/0076441 A1 | 6/2002 | Shih et al. | |
| 2002/0090725 A1 | 7/2002 | Simpson et al. | |
| 2002/0124855 A1 | 9/2002 | Chachques | |
| 2002/0142458 A1 | 10/2002 | Williams et al. | |
| 2002/0146557 A1 | 10/2002 | Claude et al. | |
| 2002/0188170 A1 | 12/2002 | Santamore et al. | |
| 2003/0023202 A1 | 1/2003 | Nielson | |
| 2003/0040712 A1 | 2/2003 | Ray et al. | |
| 2003/0050597 A1 | 3/2003 | Dodge et al. | |
| 2003/0078671 A1 | 4/2003 | Lesniak et al. | |
| 2003/0105493 A1 | 6/2003 | Salo | |
| 2003/0175410 A1 | 9/2003 | Campbell et al. | |
| 2004/0181206 A1 | 9/2004 | Chiu et al. | |
| 2004/0185084 A1 | 9/2004 | Rhee et al. | |
| 2004/0208845 A1 | 10/2004 | Michal et al. | |
| 2004/0213756 A1 | 10/2004 | Michal et al. | |
| 2005/0015048 A1 | 1/2005 | Chiu et al. | |
| 2005/0031874 A1 | 2/2005 | Michal et al. | |
| 2005/0042254 A1 | 2/2005 | Freyman et al. | |
| 2005/0070844 A1 | 3/2005 | Chow et al. | |
| 2005/0186240 A1 | 8/2005 | Ringeisen et al. | |
| 2005/0281883 A1 | 12/2005 | Daniloff et al. | |
| 2006/0233850 A1 | 10/2006 | Michal | |
| 2007/0270948 A1 | 11/2007 | Wuh | |

FOREIGN PATENT DOCUMENTS

| | | |
|---|---|---|
| EP | 0861632 | 9/1998 |
| EP | 0938871 | 9/1999 |
| GB | 2194144 | 3/1988 |
| JP | 61205446 | 9/1986 |
| WO | WO-9210142 | 6/1992 |
| WO | WO-9830207 | 7/1998 |
| WO | WO-9854301 | 12/1998 |
| WO | WO-0016818 | 3/2000 |
| WO | WO-0071196 | 11/2000 |
| WO | WO-0124775 | 4/2001 |
| WO | WO-0145548 | 6/2001 |
| WO | WO-0149357 | 7/2001 |
| WO | WO-0228450 | 4/2002 |
| WO | WO-0240070 | 5/2002 |
| WO | WO-02072166 | 9/2002 |
| WO | WO-02087623 | 11/2002 |
| WO | WO-03022909 | 3/2003 |
| WO | WO-03027234 | 4/2003 |
| WO | WO-03064637 | 8/2003 |
| WO | WO-2004000915 | 12/2003 |
| WO | WO-2004050013 | 6/2004 |
| WO | WO-2004066829 | 8/2004 |
| WO | WO-2004091592 | 10/2004 |
| WO | WO-2005061019 | 7/2005 |
| WO | WO-2005067890 | 7/2005 |
| WO | WO-2006039704 | 4/2006 |
| WO | WO-2006113407 | 10/2006 |
| WO | WO-2007048831 | 3/2007 |

OTHER PUBLICATIONS

Kelley et al., "Restraining Infarct Expansion Preserves Left Ventricular Geometry and Function After Acute Anteroapical Infarction" Circ., 1999; 99:135-142.

Lindsey et al. "Selective matrix metalloproteinase inhibitors reduce left ventricle remodeling bud does not inhibit angiogenesis after myocardial infarction," Circulation Feb. 12, 2002; 105 (6): 753-8.

Lyman, MD et al. "Characterization of the formation of interfacially photopolymeedrized thin hudrogels in contact with aterial tissue biomaterials" Feb. 1996; 17 (3):359-64.

Sawhney, A.S. et al., "Bioerodible Hydrogels Based on Photopolymerized Poly(ethylene glycol)-co-poly(a-hydroxy acid) Diacrylare Macromers" Macromolecules (1993) 26, 581-587.

Agocha A. et al. "Hypoxia regulates basal and induced DNA synthesis and collagen type I production in human cardiac fibroblasts: effects of transforming growth factor-beta 1, thyroid hormone, angiotensin II snd fibroblast growth factor" J. Mol. Cell. Cardiol. (1997) 29(8): 2233-2244.

Lu, L et al. "Biodegradable Polymer Scaffolds for Cartilage Tissue Engineering" Clin Orthop 2001 Oct; (391 Suppl): S251-70.

Luo, Y., Kirker, K.R., Prestwich, G.D. "Cross linked hyaluronic acid hydrogel films: new biomaterials for drug delivery." J. Control Rel, 69, (2000) p. 169-184.

K. Huang, et al. "Synthesis and Characterization of Self-Assembling Block Copolymers Containing Bioadhesive End Groups" Biomacromolecules 3(2) 397-406 (2002).

Ohyanagi, H. et al. "Proceedings of First Meeting" Int. Soc. Arti Org 1:90 (1977).

Creemers et al. "Matrix Metalloproteinase Inhibition After MI: A new Approach to prevent Hear Failure?" Circ. Res vol. 89:201-210 2001.

Gupta et al. "Changes in Passive Mechanical Stiffness of Myocardial Tissue with Aneurysm Formation" Circulation vol. 89 No. 5 May 1994 pp. 2315-2326.

A. Berger et al. "Ply-L-Cysteine"J. Am Chem Soc 78 4483 (1956).

L. Zervas et al. J. Am Chem Soc 85 1337 (1963).

Kyati Truong Nguyen, Jennifer L. West, "Photopolymerizable hydrogels for tissue engineering applications", Biomaterials , 23, 2002 pp. 4307-4314.

J.V. Crivello, et al. "Synthesis and Photoinitiated Cationic Polymerization of Monomers with the Silsesquioxane Core" J Polym Science Part A Polym Chem 35 407-425 (1997).

Suna Ozbas-Turan "Controlled Release of Interleukin-2 from Chitosan Microspheres" Jorunal of Pharmaceutical Sciences, vol. 91, 1245-1251 (2002).

Francis G. Spinale "Matrix Metalloproteinases Regulation and Dysregulation in the Failing Heart" Circ. Res. 2002; 90:520-530.

Li YY et al. "Differential Expression of Tissue Inhibitors of Metalloproteinases in the Failing Human Heart" Circ. Oct. 27, 1998; 98(17): 1728-34.

Internet Website: http://www.fusionmed.com/docs/surgion/default.asp.

Internet Website: http://www.canderm.com/artecoll/tech.html.

Abbott Cardiovascular Systems, Office Action dated Apr. 6, 2009 for U.S. Appl. No. 11/447,340.

Abbott Cardiovascular Systems, Office Action dated Mar. 30, 2009 for U.S. Appl. No. 10/792,960.

Abbott Cardiovascular Systems, Office Action dated Apr. 13, 2009 for U.S. Appl. No. 11/566,643.

Abbott Cardiovascular Systems, Office Action dated Apr. 29, 2009 for U.S. Appl. No. 12/013,286.

Abbott Cardiovascular Systems, Office Action dated May 12, 2009 for U.S. Appl. No. 11/496,824.

Abbott Cardiovascular Systems, Non-Final Office Action dated Mar. 13, 2009 for U.S. Appl. No. 10/414,602.

Abbott Cardiovascular Systems in, PCT International Preliminary Report on Patentability and Written Opinion dated Dec. 24, 2008 for PCT/US2007/013181., P4437X2PCT, 11 pages.

Abbott Cardiovascular Systems in, "PCT International Search Report and Written Opinion mailed Feb. 10, 2009", PCT/US2007/023419, 17 pages.

Allemann, E., et al., "Kinetics of Blood Component Adsorption on poly(D,L-lactic acid) Nanoparticles: Evidence of Complement C3 Component Involvement", J. Biomed. Mater. Res., 37(2), Abstract downloaded from the Internet at: http://www.ncbi.nlm.nih.gov/entrez/query.fcgi?cmd=Retrieve&db=PubMed, (Nov. 1997), pp. 229-234.

Anderson, James M., et al., "Biodegradation and biocompatibility of PLA and PLGA microspheres", Advanced Drug Delivery Reviews 28, (1997), 5-24.

Assmus, B., et al., "Transplantation of Progenitor Cells and Regeneration Enhancement in Acute Myocardial Infarction (Topcare-AMI)", Clinical Investigation and Reports, Department of Molecular Cardiology and Department of hematology (H.M., D.H.) University of Frankfurt, Frankfurt, germany. Circulation Available at http://www.circulationha.org DOI: 10.116, (Oct. 8, 2002), pp. 3009-3017.

Bernatowicz, M. , et al., "Preparation of Boc-[S-(3-nitro-2-pyridinesulfenyl)]-cysteine and its use for Unsymmetrical Disulfide Bond Formation", Int. J. Peptide Protein Res. 28(2), (Aug. 1996), pp. 107-112.

Boland, E. D., "Electrospinning Collagen and Elastin: Preliminary Vascular Tissue Engineering", Frontiers in Bioscience, vol. 9, (May 1, 2004), pp. 1422-1432.

Brust, G., "Polyimides", downloaded from the Internet at: http://www.pslc.ws/macrog/imide.htm, (2005), 4 pages.

Buschmann, I, et al., "Arteriogenesis versus angiogenesis: Two mechanisms of vessel growth", News Physiol. Sci., vol. 14, (Jun. 1999), 121-125.

Capan, Y., et al., "Preparation and Characterization of Poly(D,L-lactide-co-glycolide) Microspheres for Controlled Release of Human Growth Hormone", AAPS PharmSciTech.; 4(2): article 28, Downloaded from the Internet at: http://www.aapspharmscitech.org/view.asp?art=pt040228&pdf=yes, (2003), 12 pages.

Caplan, Michael J., et al., "Dependence on pH of polarized sorting of secreted proteins", Dept. of Cell Biology and Dept. of Pathology, Yale Universit School of Medicine, Nature vol. 329, (Oct. 15, 1987), 630.

Carpino, L., et al., "Tris(2-aminoethyl)amine as a Substitute for 4-(Aminomethyl)piperidine in the FMOC/Polyamine Approach to Rapid Peptide Synthesis", J. Org. Chem., 55(5), (Mar. 1990), pp. 1673-1675.

Chandy, et al., "The development of porous alginate/elastin/PEG composite matrix for cardiovascular engineering", Journal of Biomaterials Applications, vol. 17, (Apr. 2003), 287-301.

Choi, Young Seon, et al., "Study on gelatin-containing artificial skin: I. Preparation and characteristics of novel gelatin-alginate sponge", Biomaterials, vol. 20, (1999), 409-417.

Corbett, S., et al., "Covalent Cross-linking of Fibronectin to Fibrin is Required for Maximal Cell Adhesion to a Fibronectin-Fibrin Matrix", The Journal of Biological Chemistry, 272(40), (Oct. 3, 1997), pp. 24999-25005.

Davis, M. E., et al., "Injectable Self-Assembling Peptide Nanofibers Create Intramyocardial Microenvironments for Endothelial Cells", Circulation, 111, (Feb. 2005), pp. 442-450.

De Rosa, et al., "Biodegradable Microparticles for the Controlled Delivery of Oligonucleotides", International Journal of Pharmaceutics, 242, (Aug. 21, 2002), pp. 225-228.

Desai, M. , et al., "Polymer bound EDC (P-EDC): A convenient reagent for formation of an amide bond", Tetrahedron Letters, 34(48), Abstract downloaded from the Internet at: http://www.sciencedirect.com, 1 page, (Nov. 1993), pp. 7685-7688.

Dinbergs, et al., "Cellular response to transforming growth factor-β1 and basic fibroblast growth factor depends on release kinetics and extracellular matrix interactions", The Journal of Biological Chemistry, vol. 271, No. 47, (Nov. 1996), 29822-29829.

Dong, Zhanfeng , et al., "Alginate/gelatin blend films and their properties for drug controlled release", Journal of Membrane Science, vol. 280, (2006), 37-44.

Edelman, "Controlled and modulated release of basic fibroblast growth factor", Biomaterials, vol. 12, (Sep. 1999), 619-626.

Elbert, D. L., et al., "Protein delivery from materials formed by self-selective conjugate addition reactions", Journal of Controlled Release, 76, (2001), 11-25.

Etzion, S. , et al., "Influence of Embryonic Cardiomyocyte Transplantation on the Progression of Heart Failure in a Rat Model of Extensive Myocardial Infarction", J. Mol. Cell Cardiol., 33, (May 2001), pp. 1321-1330.

Ferrara, N. , "Role of Vascular Endothelial Growth Factor in the Regulation of Angiogenesis", Kidney International, 56(3), Abstract downloaded from the Internet at: http://www.nature.com/ki/journal/v56/n3/abs/4490967a.html, 1 page, (1999), pp. 794-814.

Friedman, Paul M., et al., "Safety Data of Injectable Nonanimal Stabilized Hyaluronic Acid Gel for Soft Tissue Augmentation", Dermatologic Surgery, vol. 28, (2002), pp. 491-494.

Fuchs, S. , et al., "Catheter-Based Autologous Bone Marrow Myocardial Injection in No-Option Patients with Advanced Coronary Artery Disease", J. Am. Coll. Cardiol., 41(10), (2003), pp. 1721-1724.

Fukumoto, S. , et al., "Protein Kinase C δ Inhibits the Proliferation of Vascular Smooth Muscle Cells by Suppressing G1 Cyclin Expression", The Journal of Biological Chemistry, 272(21), (May 1997), pp. 13816-13822.

Giordano, F. , et al., "Angiogenesis: the Role of the Microenvironment in Flipping the Switch", Current Opinion in Genetics and Development, 11, (2001), pp. 35-40.

Gossler, et al., "Transgenesis by means of blastocyst-derived embryonic stem cell lines", Proc. Natl. Acad. Sci. USA, 83, (Dec. 1986), pp. 9065-9069.

Grafe, T. H., "Nanofiber Webs from Electrospinning", Presented at the Nonwovens in Filtration—Fifth International Conference,, Stuttgart, Germany, (Mar. 2003), pp. 1-5.

Gref, R. , et al., "Biodegradable Long-Circulating Polymeric Nanospheres", Science, 263(5153), Abstract downloaded from the Internet at: http://www.sciencemag.org/cgi/content/abstract/263/5153/1600, 1 page, (Mar. 1994), pp. 1600-1603.

Grund, F. , et al., "Microembolization in Pigs: Effects on Coronary Blood Flow and Myocardial Ischemic Tolerance", Am. J. Physiol., 277 (Heart Circ. Physiol. 46), (1999), pp. H533-H542.

Hanawa, T. , et al., "New oral dosage form for elderly patients: preparation and characterization of silk fibroin gel", Chemical and Pharmaceutical Bulletin, Pharmaceutical Society of Japan, Tokyo, vol. 43, No. 2, (Jan. 1995), 284-288.

Hashimoto, T. , et al., "Development of Alginate Wound Dressings Linked with Hybrid Peptides Derived from Laminin and Elastin", Biomaterials, 25, (2004), pp. 1407-1414.

Haugland, et al., "Dialkylcarbocyanine and Dialkylaminostryryl Probes", Handbook of Fluorescent Probes and Research Products, Molecular Probes, Inc., (2002), 530-534.

Haugland, et al., "Membrane-permeant reactive tracers", Handbook of Fluorescent Probes and Research Products, Molecular Probes, Inc., (2002), 458-553.

Heeschen, C. , et al., "Nicotine Stimulates Tumor Angiogenesis", American College of Cardiology, 37(2) Supplement A,, Abstract downloaded from the Internet at: http://24.132.160.238/ciw-01acc/abstract_search_author.cfm?SearchName=Heeschen, 1 page, (Feb. 2001), pp. 1A-648A.

Helisch, A , et al., "Angiogenesis and arteriogenesis—not yet for prescription", NEUE Diagnostische Und Therap. Verfahren, Z Kardiol 89, (2000), 239-244.

Hendel, R. C., et al., "Effect of Intracoronary Recombinant Human Vascular Endothelial Growth Factor on Myocardial Perfusion: Evidence for a Dose-Dependent Effect", Circulation, 101, (2000), pp. 118-121.

Henry, R. R., et al., "Insulin Action and Glucose Metabolism in Nondiabetic Control and NIDDM Subjects: Comparison Using Human Skeletal Muscle Cell Cultures", Diabetes, 44(8), Abstract downloaded from the Internet at: http://diabetes.diabetesjournals.org/cgi/content/abstract/44/8/936, 1 page, (1995), pp. 936-946.

Hoffman, "Hydrogels for Biomedical Applications", Advanced Drug Delivery Reviews, vol. 43, (2002), pp. 3-12.

Holland, N. B., et al., "Biomimetic Engineering of Non-Adhesive glycocalyx-like Surfaces Using Oligosaccharide Surfactant Polymers", Nature, 392, Abstract downloaded from the Internet at: http://www.nature.com, 1 page, (Apr. 1998), pp. 799-801.

Horan, R.L., et al., "In Vitro Degradation of Silk Fibroin", Biomaterials, vol. 26, (2004), 3385-3393.

Hovinen, J., et al., "Synthesis of 3'-functionalized oligonucleotides on a single solid support", Tetrahedron Letters, 34(50), Abstract downloaded from the Internet at: http://www.sciencedirect.com, 1 page, (Dec. 1993), pp. 8169-8172.

Huynh, T. V., et al., "Constructing and Screening cDNA Libraries in λgt10 and λgt11", Chapter 2 in DNA Cloning, vol. 1: A Practical Approach, ed. By D.M. Glover, (1985), pp. 49-78.

Indik, Z., et al., "Production of Recombinant Human Tropoelastin: Characterization and Demonstration of Immunologic and Chemotactic Activity", Arch. Biochem. Biophys., 280(1), Abstract downloaded from the Internet at: http://www.ncbi.nlm.nih.gov/entrez/query.fcgi?cmd=Retrieve&db=PubMed, 1 page, (Jul. 1990), pp. 80-86.

Iskandrian, A. S., et al., "Nuclear Cardiac Imaging: Principles and Applications", second edition, F.A. Davis Co., Philadelphia, cover page, title page and TOC, (1996), 5 pages total.

Isner, J. M., "Vascular Endothelial Growth Factor: Gene Therapy and Therapeutic Angiogenesis", Am. J. Cardiol., 82(10A), (Nov. 19, 1998), pp. 63S-64S.

Ito, Wulf D., et al., "Monocyte chemotactic protein-1 increases collateral and peripheral conductance after femoral artery occlusion", Max-Planck-Institute for Physiological and Clinical Research, Bad Nauheim, Germany, (Feb. 21, 1997), 829-837.

Johnson, et al., "The stabilization and encapsulation of human growth hormone nto biodegradable microspheres", Pharmaceutical Research, vol. 14, No. 6, (1997), 730-735.

Jonasson, P., et al., "Denatured states of human carbonic anhydrase II: an NMR study of hydrogen/deuterium exchange at tryptophan-indole-Hn sites", FEBS Letters, 445, (1999), pp. 361-365.

Kalltorp, Mia, et al., "Inflammatory cell recruitment, distribution, and chemiluminescence response at IgG precoated- and thiol functionalized gold surfaces", Swedish Biomaterials Consortium, Swedish Foundation for Strategic Research, (Apr. 9, 1999), 251-259.

Kaplan, D.L., et al., "Spiderless Spider Webs", Nature Biotechnology, vol. 20, (2002), 239-240.

Kawai, et al., "Accelerated tissue regeneration through incorporation of basic fibroblast growth factor-impregnated gelatin microspheres into artificial dermis", Biomaterials, 21(5), (Mar. 2002), 489-499.

Kawasuji, M., et al., "Therapeutic Angiogenesis with Intramyocardial Administration of Basic Fibroblast Growth Factor", Ann Thorac Surg, 69, Abstract downloaded from the Internet at: http://ats.ctsnetjournals.org/cgi/content/abstract/69/4/1155, 2 pages, (2000), pp. 1155-1161.

Kelly, E. B., "Advances in Mammalian and Stem Cell Cloning", Genetic Engineering News, vol. 23, No. 7, (Apr. 1, 2003), pp. 17-18 & 68.

Khademhosseini, et al., "Microscale Technologies for Tissue Engineering and Biology", PNAS, vol. 103, No. 8, (Feb. 21, 2006), pp. 2480-2487.

Kim, D., et al., "Glow Discharge Plasma Deposition (GDPD) Technique for the Local Controlled Delivery of Hirudin from Biomaterials", Pharmaceutical Research, 15(5), (1998), pp. 783-786.

Kim, Ung-Jin, et al., "Structure and Properties of Silk Hydrogels", Biomacromolecules, vol. 5(3), (2004), 786-792.

Kinart, et al., "Electrochemical Studies of 2-hydroxy-3-(3,4-dimethy1-9-oxo-9H-thioxanthen-2-yloxy)N,N,N-trimethy1-1-propanium chloride", J. Electroanal. Chem, 294, (1990), pp. 293-297.

Kipshidze, Nicholas, et al., "Therapeutic angiogenesis for critical limb ischemia to limit or avoid amputation", University of Wisconsin Medical School, The Journal of Invasive Cardiology, vol. 11, No. 1, (Jan. 1999), 25-28.

Klein, S., et al., "Fibroblast Growth Factors as Angiogenesis Factors: New Insights Into Their Mechanism of Action", Regulation of Angiogenesis, I.D. Goldberg and E.M. Rosen (eds.), 79, (1997), pp. 159-192.

Klugherz, Bruce D., et al., "Gene delivery from a DNA controlled-release stent in porcine coronary arteries", Nature Biotechnology, vol. 18, (Nov. 2000), 1181-1184.

Kohilas, K, et al., "Effect of prosthetic titanium wear debris on mitogen-induced monocyte and lymphoid activation", John Hopkins University, Dept. of Orthopaedic Surgery, (Apr. 1999), 95-103.

Kweon, H. Y., et al., "Preparation of semi-interpenetrating polymer networks composed of silk fibroin and poly(ethyleneglycol) macromer", Journal of Applied Polymer Science, John Wiley and Sons Inc., New York, NY, vol. 80, (Jan. 2001), 1848-1853.

Kwok, C., et al., "Design of Infection-Resistant Antibiotic-Releasing Polymers: I. Fabrication and Formulation", Journal of Controlled Release, 62, (1999), pp. 289-299.

Laboratory of Liposome Research, "Liposomes: General Properties", downloaded from the Internet on Feb. 9, 2006 at: http://wvvw.unizh.ch/onkwww/lipos.htm, 5 pages.

Laham, R. J., "Intrapericardial Delivery of Fibroblast Growth Factor-2 Induces Neovascularization in a Porcine Model of Chronic Myocardial Ischemia", J. Pharmacol Exper Therap, 292(2), (2000), pp. 795-802.

Leibovich, S. J., et al., "Macrophage-Induced Angiogenesis is Mediated by Tumour Necrosis Factor-α", Nature, vol. 329, (Oct. 15, 1987), pp. 630-632.

Leor, J., et al., "Bioengineered Cardiac Grafts-A New Approach to Repair the Infarcted Myocardium?", Circulation, 102[suppl III], (2000), pp. III-56-III-61.

Leor, J., et al., "Gene Transfer and Cell Transplant: An Experimental Approach to Repair a 'Broken Heart'", Cardiovascular Research, 35, (1997), pp. 431-441.

Leroux, J. C., et al., "An Investigation on the Role of Plasma and Serum Opsonins on the Internalization of Biodegradable poly(D,L-lactic acid) Nanoparticles by Human Monocytes", Life Sci., 57(7), Abstract downloaded from the Internet at: http://www.ncbi.nlm.nih.gov/entrez/query.fcgi?cmd=Retrieve&db=pubmed, 1 page, (1995), pp. 695-703.

Lewin, B., "Repressor is Controlled by a Small Molecule Inducer", Genes VII, Oxford University Press, 7th ed., (2000), pp. 277-280.

Li, et al., "Cell Therapy to Repair Broken Hearts", Can. J. Cardiol., vol. 14, No. 5, (May 1998), pp. 735-744.

Li, W. W., et al., "Lessons to be Learned from Clinical Trials of Angiogenesis Modulators in Ischemic Diseases", Angiogenesis in Health & Disease: Basic Mechanisms and Clinical Applications, Rubanyi, G. (ed), Marcel Dekker, Inc. New York, (2000), Chapter 33.

Li, J. , et al., "PR39, A Peptide Regulator of Angiogenesis", Nature Medicine, 6(1), (Jan. 2000), pp. 49-55.

Long, D. M., et al., "Self-Cleaving Catalytic RNA", FASEB Journal, 7, (1993), pp. 25-30.

Lopez, J. J., et al., "Angiogenic potential of perivascular delivered aFGF in a porcine model of chronic myocardial ischemia", The American Physiological Society, 0363-6135/98, (1998), H930-H936.

Lopez, J. J., et al., "VEGF Administration in Chronic Myocardial Ischemia in Pigs", Cardiovasc. Res., 40(2), Abstract downloaded from the Internet at: http://www.ncbi.nlm.nih.gov/entrez/query.fcgi?cmd=Retrieve&db=pubmed, 1 page, (1998), pp. 272-281.

Lutolf, M , et al., "Synthesis and Physicochemical Characterization of End-Linked Poly(ethylene glycol)-co-peptide Hydrogels Formed by Michael-Type Addition", Biomacromolecules, vol. 4, (2003), 713-722.

Mansour, S. , et al., "Disruption of the proto-oncogene int-2 in mouse embryo-derived stem cells: a general strategy for targeting mutations to non-selectable genes", Nature, 336, (1988), pp. 348-352.

Martin, S. L., et al., "Total Synthesis and Expression in *Escherichia coli* of a Gene Encoding Human Tropoelastin", Gene, (1995), Abstract, 1 page.

Mcdevitt T., et al., "In vitro Generation of Differentiated Cardiac Myofibers on Micropatterned Laminin Surfaces", J. Biomed Mater Res., 60, (2002), pp. 472-479.

Meinel, L., et al., "The Inflammatory Responses to Silk Films In Vitro and In Vivo", Biomaterials, vol. 26, (2005), 147-155.

Narmoneva, D. A., et al., "Self-assembling short oligopeptides and the promotion of angiogenesis", Biomaterials, 26, (2005), pp. 4837-4846.

Nazarov, R., et al., "Porous 3-D Scaffolds from Regenerated Silk Fibroin", Biomacromolecules, vol. 5(3), (2004), 718-726.

Nikolic, S. D., et al., "New Angiogenic Implant Therapy Improves Function of the Ischemic Left Venticle", Supplement to Circulation; Abstracts From Scientific Sessions 2000, 102(18), (Oct. 2000), pp. II-689, Abstract 3331.

Nikolic, Serjan D., et al., "Novel means to improve coronary blood flow", Clinical Science, Abstracts from Scientific Sessions, (2000), II-689.

Nitinol Technical Information, "NiTi Smart Sheets", downloaded from the Internet on Dec. 10, 2002 at: http://www.sma-inc.com/information.html, 1 page.

Nose, et al., "A novel cadherin cell adhesion molecule: its expression patterns associated with implantation and organogenesis of mouse embryos", Journal of Cell Biology, vol. 103 (No. 6, Pt. 2), The Rockefeller University Press, (Dec. 1986), 2649-2658.

Ozbas, B., et al., "Salt-Triggered Peptide Folding and Consequent Self-Assembly into Hydrogels with Tunable Modulus", Macromolecules, 37(19), (2004), pp. 7331-7337.

Palmiter, R., et al., "Germ-Line Transformation of Mice", Ann. Rev. Genet., 20, (1986), pp. 465-499.

Patrick, C. R., "Mixing and Solution Properties of Organofluorine Compounds", Preparation, Properties and Industrial Applications of Organofluorine Compounds, Chapter 10, R.E. Banks (ed.), 1st edition, Ellis-Horwood Ltd., Chichester:England, (1982), pp. 323-342.

Peattie, R. A., et al., "Stimulation of In Vivo Angiogenesis by Cytokine-Loaded Hyaluronic Acid Hydrogel Implants", Biomaterials, 25(14), Abstract downloaded from: www.sciencedirect.com, (Jun. 2004), 2 pages.

Penta, K., et al., "Del1 Induces Integrin Signaling and Angiogenesis by Ligation of αVβ3", J. Biolog. Chem., 274(16), (Apr. 1999), pp. 11101-11109.

Perin, E. C., et al., "Transendocardial, Autologous Bone Marrow Cell Transplantation for Severe, Chronic, Ischemic Heart Failure", Circulation, (2003), 1 page.

Pouzet, B., et al., "Is Skeletal Myoblast Transplantation Clinically Relevant in the Era of Angiotensin-Converting Enzyme Inhibitors?", Circulation, 104 [suppl 1], (Sep. 2001), pp. I-223-I-228.

Prather, et al., "Nuclear Transplantation in Early Pig Embryos", Biol. Reprod., 41, (1989), pp. 414-418.

Prosci Incorporated, "ILPIP (CT) Peptide", 1 page.

Quellec, P., et al., "Protein Encapsulation Within Polyethylene Glycol-coated Nanospheres. I. Physicochemical Characterization", J. Biomed. Mater. Res., 42(1), (1998), Abstract, 1 page.

Ramirez-Solis, R., et al., "Gene Targeting in Embryonic Stem Cells", Methods in Enzymology, 225, (1993), pp. 855-878.

Rowley, et al., "Alginate Hydrogels as Synthetic Extracelllular Matrix Materials", Biomaterials, 20(1), (1999), 45-53.

Sbaa-Ketata, E., et al., "Hyaluronan-Derived Oligosaccharides Enhance SDF-1-Dependent Chemotactic Effect on Peripheral Blood Hematopoietic CD34+Cells", Stem Cells, 20(6), Letter to the Editor downloaded from the Internet at: http://stemcells.alphamedpress.org/cgi/content/full/20/6/585, (2002), 585-587.

Segura, T, et al., "Crosslinked Hyaluronic Acid Hydrogels: A Strategy to Functionalize and Pattern", Biomaterials, vol. 26(4), (Feb. 2005), 359-371.

Segura, T., et al., "DNA delivery from hyaluronic acid-collagen hydrogels via a substrate-mediated approach", Biomaterials, vol. 26, (2005), 1575-1584.

Segura, T., et al., "Substrate-Mediated DNA Delivery: Role of the Cationic Polymer Structure and Extent of Modification", Journal of Controlled Release, 93, (2003), pp. 69-84.

Segura, T., et al., "Surface-Tethered DNA Complexes for Enhanced Gene Delivery", Bioconjugate Chem, 13(3), (2002), pp. 621-629.

Shibasaki, F., et al., "Suppression of Signalling Through Transcription Factor NF-AT by Interactions Between Calcineurin and BcI-2", Nature, 386(6626), Abstract downloaded from the Internet at: http://www.ncbi.nlm.nih.gov/entrez/query.fcgi?CMD=Text &DB=pubmed, 1 page, (1997).

Shin, H., et al., "Attachment, Proliferation, and Migration of Marrow Stromal Osteoblasts Cultured on Biomimetic Hydrogels Modified with an Osteopontin-Derived Peptide", Biomaterials, 25, (2004), pp. 895-906.

Shin, H., et al., "In vivo bone and soft tissue response to injectable, biodegradable oligo(poly(ethylene glycol) fumarate) hydrogels", Biomaterials 24, Elseview Science Ltd., (3201-3211), 2003.

Shu, Z , et al., "Disulfide-crosslinked hyaluronan-gelatin hydrogel films: a covalent mimic of the extracellular matrix for in vitro cell growth", Biomaterials, vol. 24(21), (Sep 2003), 3825-3834.

Shu, Zheng, et al., "In situ crosslinkable hyaluronan hydrogels for tissue engineering", Biomaterials, vol. 25, No. 7-8, (Mar. 2004), 1339-1348.

Simons, M., et al., "Clinical trials in coronary angiogenesis: Issues, problems, consensus, An expert panel summary", Angiogenesis Research Center, American Heart Association, Inc., (Sep. 12, 2000), 1-14.

Spenlehauer, G, et al., "In vitro and in vivo degradation of poly(D,L lactide/glycolide) type microspheres made by solvent evaporation method", Biomaterials, vol. 10, (Oct. 1989), 557-563.

Springer, M., et al., "Angiogenesis Monitored by Perfusion with a Space-Filling Microbead Suspension", Mol. Ther., 1(1), Abstract downloaded from the Internet at: http://www.ncbi.nlm.nih.gov/entrez/query.fcgi?cmd=Retrieve&db=PubMed, 1 page, (2000), pp. 82-87.

Staatz, WD, et al., "Identification of a tetrapeptide recognition sequence for the alpha 2 beta 1 integrin in collagen", Journal of Biological Chemistry, 1991, 266(12), pp. 7363-7367.

Storm, G., et al., "Surface Modification of Nanoparticles to Oppose Uptake by the Mononuclear Phagocyte System", Advanced Drug Delivery Reviews, 17(1), Abstract downloaded from the Internet at: http://www.sciencedirect.com, 1 page, (Oct. 1995), pp. 31-48.

Strauer, B. , et al., "Repair of Infarcted Myocardium by Autologous Intracoronary Mononuclear one Marrow Cell Transplantation in Humans", Circulation, 106, (2002), pp. 1913-1918.

Tybulewicz, V., et al., "Neonatal lethality and lymphopenia in mice with a homozygous disruption of the c-abl proto-oncogene", Cell, 65(7), Abstract downloaded from the Internet at: http://www.sciencedirect.com, 2 pages, (Jun. 1991), pp. 1153-1163.

Unger, E. F., et al., "Effects of a Single Intracoronary Injection of Basic Fibroblast Growth Factor in Stable angina Pectoris", Am. J. Cardiol., 85(12), Abstract downloaded from the Internet at: http://www.sciencedirect.com, 2 pages, (Jun. 2000), pp. 1414-1419.

Van Der Giessen, Willem J., et al., "Marked inflammatory sequelae to implantation of biodegradable and nonbiodegradable polymers in porcine coronary arteries", Dept. of Cardiology, Erasmus University Rotterdam, Circulation, vol. 94, No. 7, (Oct. 1, 1996), 1690-1697.

Van Luyn, M. J., et al., "Cardiac Tissue Engineering: Characteristics of In Unison Contracting Two- and Three-Dimensional Neonatal Rat Ventricle Cell (Co)-Cultures", Biomaterials, 23, (2002), pp. 4793-4801.

Vercruysse, K. P., et al., "Synthesis and in Vitro Degradation of New Polyvalent Hydrazide Cross-Linked Hydrogels of Hyaluronic Acid", Bioconjugate Chem, 8(5), Abstract downloaded from the Internet at: http://pubs.acs.org/cgi-bin/abstract.cgi/bcches/1997/8/i05/abs/bc9701095.html, 1 page, (1997), pp. 686-694.

Visscher, G.E. , et al., "Tissue response to biodegradable injectable microcapsules", Journal of Biomaterials Applications, vol. 2, (Jul. 1987), 118-119.

Vlodavsky, I., et al., "Extracellular Matrix-resident Basic Fibroblast Growth Factor: Implication for the Control of Angiogenesis", J. Cell Biochem, 45(2), Abstract downloaded from the Internet at: http://www.ncbi.nlm.nih.gov/entrez/query.fcgi?cmd=Retrieve &db=PubMed, 1 page, (Feb. 1991), pp. 167-176.

Wang, M., et al., "Mechanical Properties of Electrospun Silk Fibers", Macromolecules, vol. 37(18), (2004), 6856-6864.

Wasielewski, "Ischamische Erkrankungen, Gefassneubildung anregen", Deutsche Apotheker Zeitung, vol. 140, No. 3, Stuttgart (DE), (Jan. 20, 2000), 232-233.

Wilensky, R., et al., "Direct intraarterial wall injection of microparticles via a catheter: a potential durg delivery strategy following angioplasty", American Heart Journal, 122, (1991), p. 1136.

Witzenbichler, B., et al., "Vascular Endothelial Growth Factor-C (VEGF-C/VEGF-2) Promotes Angiogenesis in the Setting of Tissue Ischemia", Am Pathol., 153(2), (Aug. 1998), pp. 381-394.

Yager, P., et al., "Silk Protein Project", www.faculty.washington.edu/yagerp/silkprojecthome.html, (Aug. 23, 1997), 18 pages.

Yamamoto, N., et al., "Histologic evidence that basic fibroblast growth factor enhances the angiogenic effects of transmyocardial laser revascularization", Basic Research in Cardiology, vol. 95, No. 1, (Feb. 1, 2000), 55-63.

Yeo, L.Y., et al., "AC Electrospray Biomaterials Synthesis", Biomaterials, (2005), 7 pages.

Zheng, W., et al., "Mechanisms of coronary angiogenesis in response to stretch: role of VEGF and TGF-beta", Am J Physiol Heart Circ Physiol., 280(2), (Feb. 2001), pp. H909-H917.

Zimmermann, W., et al., "Engineered Heart Tissue for Regeneration of Diseased Hearts", Biomaterials, 25, (2004), pp. 1639-1647.

* cited by examiner

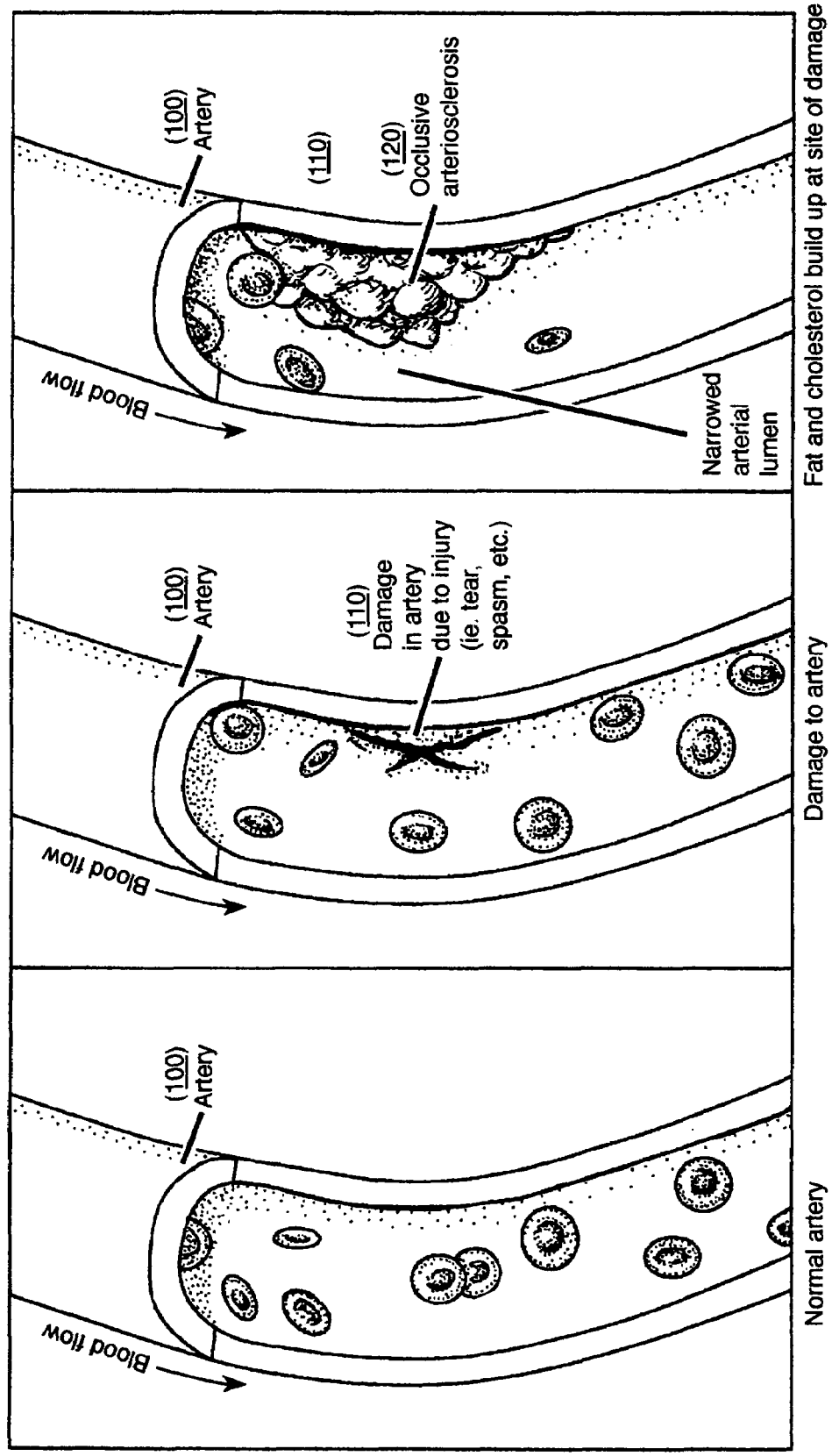

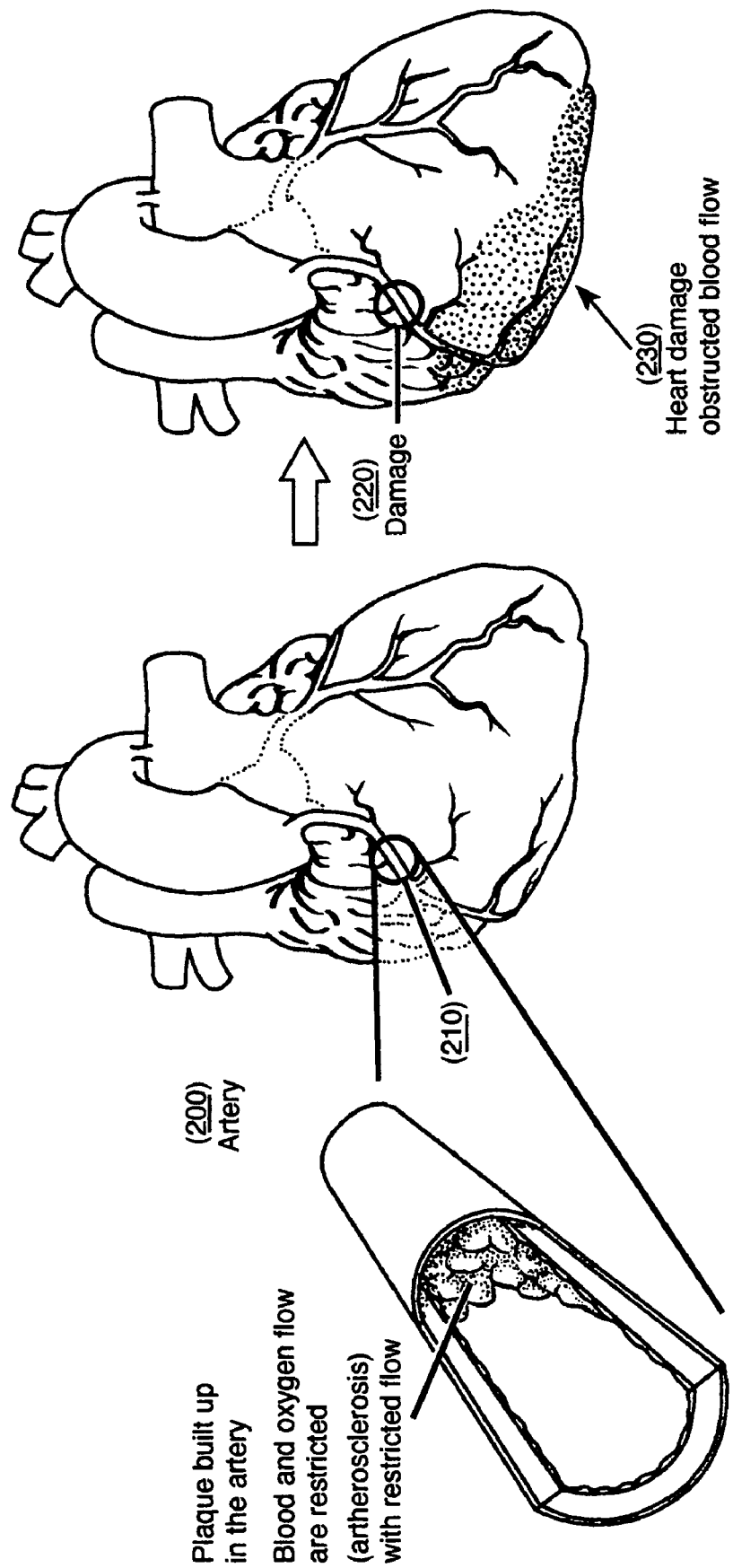

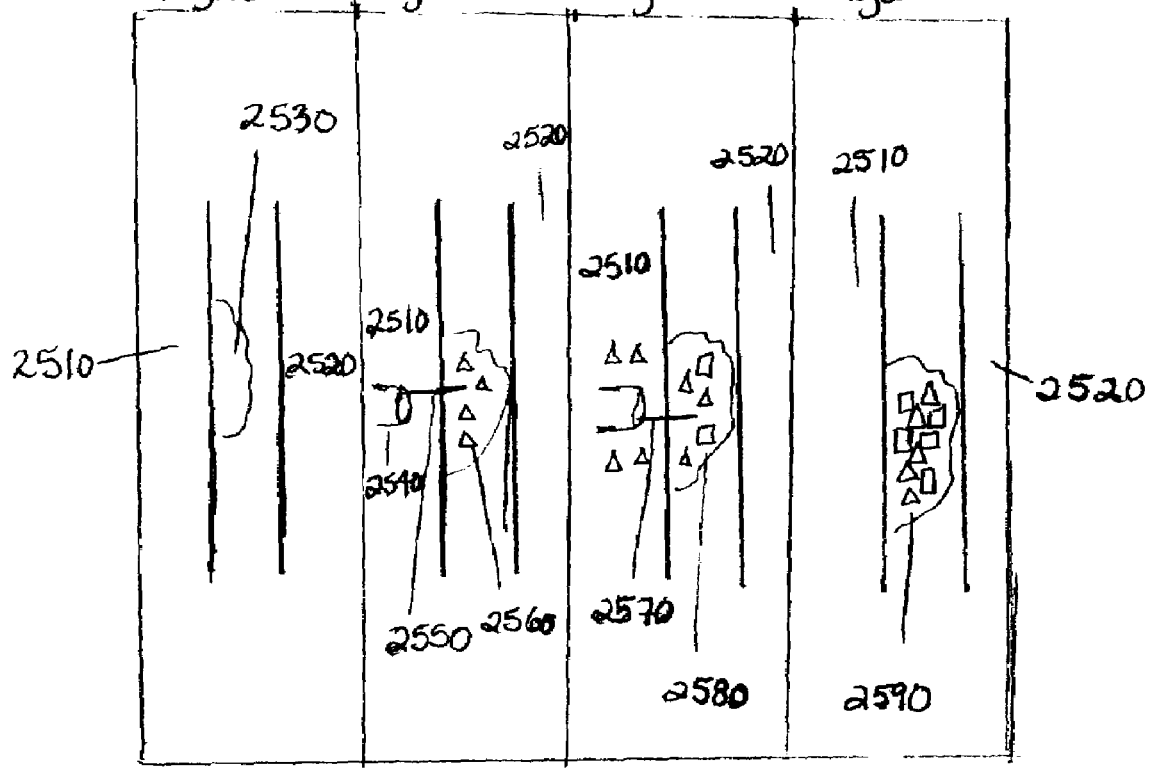

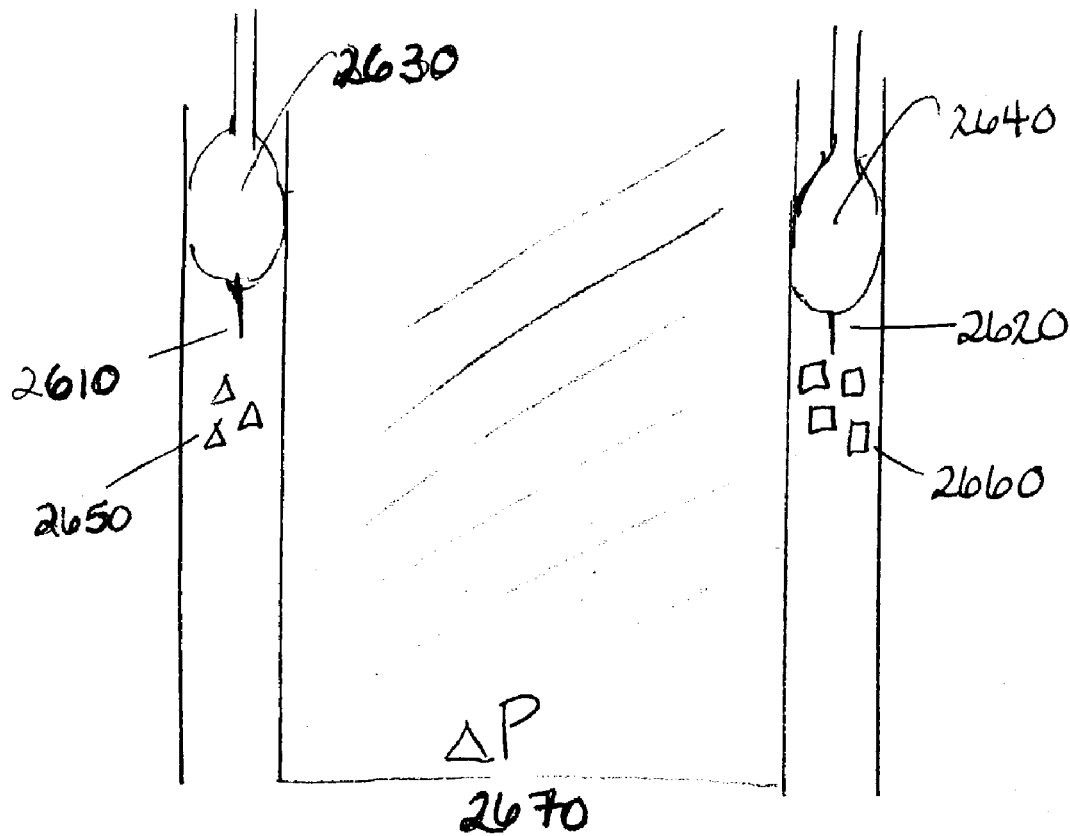

METHODS AND COMPOSITIONS TO TREAT MYOCARDIAL CONDITIONS

FIELD

The treatment of myocardial infarction, and more particularly, in one embodiment, to the reinforcement of the infarct regional wall of a heart chamber and/or the inhibition of the thinning of the infarct regional wall of a heart chamber.

BACKGROUND

Ischemic heart disease typically results from an imbalance between the myocardial blood flow and the metabolic demand of the myocardium. Progressive atherosclerosis with increasing occlusion of coronary arteries leads to a reduction in coronary blood flow. Blood flow can be further decreased by additional events such as changes in circulation that lead to hypoperfusion, vasospasm or thrombosis Myocardial infarction accounts for approximately 20% of all deaths. It is a major cause of sudden death in adults.

Myocardial Infarction (MI) is one form of heart disease that often results from the sudden lack of supply of oxygen and other nutrients. The lack of blood supply is a result of closure of the coronary artery that nourishes the particular part of the heart muscle. The cause of this event is generally caused by arteriosclerosis "hardening of the arteries" in coronary vessels.

Formerly, it was believed that an MI was caused from a slow procession of closure from for example 95% then to 100% but an MI can also be a result of minor blockages where, for example, there is a rupture of the cholesterol plaque resulting in blood clotting within the artery. Thus, the flow of blood is blocked and downstream cellular damage occurs. This damage can cause irregular rhythms that can be fatal, even though the remaining muscle is strong enough to pump a sufficient amount of blood. As a result of this insult to the heart tissue, scar tissue tends to naturally form.

Even though relatively effective systemic drugs exist to treat MI such as ACE-inhibitors and Beta-blockers, a significant portion of the population that experiences a major MI ultimately develop heart failure. An important component in the progression to heart failure is remodeling of the heart due to mechanical forces resulting in uneven stress and strain distribution in the left ventricle. Once an MI occurs remodeling of the heart begins. The principle components of the remodeling event include myocyte death, edema and inflammation, followed by fibroblast infiltration and collagen deposition, and finally scar formation. The principle component of the scar is collagen. Since mature myocytes of an adult are not regenerated the infarct region experiences significant thinning. Myocyte loss is the major etiologic factor of wall thinning and chamber dialation that may ultimately lead to progression of cardiac myopathy. Myocyte death can and does occur. In other areas, remote regions experience hypertrophy (thickening) resulting in an overall enlargement of the left ventricle. This is the end result of the remodeling cascade. These changes in the heart result in changes in the patient's lifestyle and their ability to walk and to exercise. These changes also correlate with physiological changes that result in increase in blood pressure and worsening systolic and diastolic performance.

FIG. 1A-1C illustrates blood flow by longitudinal cross sectioning of the artery. FIG. 1A illustrates a normal unobstructed artery. FIG. 1B illustrates artery damage due to a tear or spasm. This FIG. illustrates a minor insult to the interior wall. FIG. 1C illustrates an artery with plaque build-up that reduces the blood flow demonstrated by the blocked blood cell above the atherosclerotic mass. Fat and cholesterol build up at the site of damage. This mass can be detected by methods currently available such as an, ECG, SPECT, MRI, angiogram.

FIG. 2A-2B illustrate the progression of heart damage once the build-up of plaque induces an infarct to occur. The most common pathogenesis of this disease is occlusive intracoronary thrombus where a thrombus is covering an ulcerated stenotic plaque. This causes approximately 90% of transmural acute myocardial infarctions. Other possible triggers of an MI are vasospasms with or without coronary atherosclerosis and possible association with platelet aggregation. Another possible trigger is embolisms from left-sided mural thrombosis, vegetative ensocarditis or a paradoxic embolism from the right side of the heart through a patent foramen ovale. FIG. 2A illustrates a site where blockage and restricted blood flow can occur from any of the indicated causes. FIG. 2B illustrates the extensive damage to the left ventricle that can be a result of the lack of oxygen and nutrient flow carried by the blood to the inferior region left ventricle of the heart. This area will likely undergo remodeling and eventually a scar will form and a non-functional (an area that does not contract) area will exist.

Significant atherosclerotic build-up can reduce the arterial lumen and reduce blood flow. Build-up is capable of rupturing resulting in a total or partial occlusion of the artery. Complete coronary occlusion will lead to an acute MI. Thus the T-cells, platelets, fibrin and multiple other factors and cells are blocked from progression through the blood stream and the result is an inadequate vascular supply as seen. This leads to myocyte death. Myocyte death, in addition to fibrosis in the form of collagen deposition, can lead to a compromised left ventricle and overload on the remaining myocytes. This process is further complicated by compensation of the remaining myocytes that hypertrophy (enlarge). This can cause the left ventricle to enlarge and if the cycle continues can result in eventual heart failure.

The morphological appearance of the infracted heart tissue post M.I. can vary. A transmural infarct involves the entire thickness of the left ventricular wall from the endocardium to the epicardium. It may extend into the anterior free wall and the posterior free wall. This damage may include extensions into the right ventricular wall. A subendocardial infarct may have multiple focal regions and necrosis area may be confined to the inner one-third to one-half of the left ventricular wall. The evolutionary changes in a subendocardial infarct do not evolve the same as in a transmural MI.

Over time post-MI morphological changes occur. The gross morphological changes that occur over approximately a 7-week period are pallor of the myocardium that leads to some hyperemia then a yellowing starts to occur central to the damaged region. At approximately 15 days, the area is mostly yellow with soft vascular margins. This area eventually turns white from fibrosis. On a microscopic level, the initial examination reveals wavy myocardial fibers. Coagulation and necrosis with loss of cross striations occur followed by contraction bands, edema, hemorrhage, and neutrophilic infiltrate. Within 24-72 hours there is total loss of nuclei and striations and heavy neutrophilic infiltrate. Then macrophage and mononuclear infiltration begin resulting in a fibrovascular response. Once this fibrovascular response occurs then prominent granulation of the tissue follows. This ultimately leads to fibrosis and a scar is formed by about 7 weeks post MI.

FIG. 3A-3B illustrate the occlusion of an artery that may lead to an MI. FIG. 3A illustrates the cross-section of a normal coronary artery with unobstructed lumen 301. The normal arterial wall 302 is made up of an intima layer 303, a media layer 304, and an adventitia layer 305. Within the arterial lumen, the intima is in direct contact with the flow of blood. This region is mostly made up of endothelial cells. The media layer is mostly smooth muscle cells and extracellular matrix proteins. Finally, the aventitia layer is primarily made up of collagen, nerves, blood vessels and lymph vessels. FIG. 3B illustrates a coronary artery with atherosclerosis. In this example, this artery is about 50 percent occluded (only 50 percent of the arterial lumen is free of obstruction). Thus, the obstructed artery may lead to damage observed in a ventricle of an MI subject.

After an MI has occurred, three layers of tissue can be distinguished. The infarct region has (1) the region of significant necrosis/apoptosis tissue (2) the border zone that consists of a large concentration of apoptotic and necrotic tissue as well as viable tissue and (3) the unaffected region that consists of mainly viable tissue. In the border zone the cells exist in an oxygen-deprived state due to the damage from the MI.

FIG. 3C-3J illustrate the details of a post-MI remodeling of the ventricle. The progression of heart failure after an MI is a result of the remodeling of the heart after the infarct. The remodeling process causes infracted region of the heart to stretch and become thinner causing the left ventricular diameter to increase. As the heart continues to remodel, the stresses on the heart increase. FIG. 3C, on a cellular level, a normal myocardium is illustrated. FIG. 3C illustrates the cross striations 306 and central nuclei 307 of a healthy myocyte population.

FIG. 3D-3J depict the progression of the remodeling of the ventricle post MI. FIG. 3D illustrates an early acute MI. Here, there are prominent pink contraction bands that are indicated by reference number 308. FIG. 3E illustrates the increasing loss of striations and some contraction bands. The nuclei in this illustration are incurring karyolysis (A stage of cell death that involves fragmentation of a cell nucleus. The nucleus breaks down into small dark beads of damaged chromatin) 309. In addition, the neutrophils are infiltrating the damaged myocardial region. FIG. 3F illustrates an acute MI. The loss of nuclei and loss of cross striations are evident. There is extensive hemorrhaging on the infarct border 310. FIG. 3G illustrate the prominent necrosis and hemorrhaging 310, as well as the neutrophilic infiltrate 311. Subsequently, a yellowish center is formed within the damaged area with necrosis and inflammation surrounded by the hyperemic border. After 3-5 days post-MI, the necrosis and inflammation are extensive. There is a possibility of rupture at this point. FIG. 3H illustrates approximately one week after the MI with capillaries, fibroblasts and macrophages filled with haemosiderin (haemosiderin is a long-term reserve (storage form) of iron in tissues) 312. In two to three weeks granulation is the most prominent feature observed. FIG. 3I illustrates extensive collagen deposition 313 seen after a couple of weeks. Collagenous scarring occurs in subendocardial locations in remote myocardial infarct regions. FIG. 3J illustrates the myocytes 314 after several weeks of healing post MI. They are hypertrophied with large dark nuclei 315 and interstitial fibrosis 316. These enlarged cells contribute to the enlarged left ventricle.

A complication of an MI is an aneurysm that looks like a bulge in the left ventricular wall. The aneurysm is made up of non-functional tissue that is unable to contract. Therefore, the ejection and stroke volume of the heart are reduced. Additionally, parts of this mass can form a mural thrombus that can break off and embolize to the systemic circulation.

SUMMARY

Compositions and methods to treat myocardial infarction of the ventricle are described. In one embodiment, a composition is described that is capable of reinforcing the ventricular wall and may be capable of releasing an agent to recruit the natural cell population in order to stabilize the region. In another embodiment, a method is described to increase the compliance of a ventricle. A treatment agent is advanced through a delivery device to the infarct zone. In some embodiments, a delivery device is described to accurately deliver one or more treatment agents. In some embodiments, the treatment agent is delivered via a multiple of small volumes to the region. These delivery methods may use imaging of the ventricular wall to guide the deposition of the treatment agent to the site of the infarct zone such as deposition of the gel-forming agents. In other embodiments, treatment agents may induce angiogenesis.

In another embodiment, a method includes the retention of and/or recruitment of fibroblast cells to the infarct zone. In other embodiments, a method includes an early time post-MI recruitment and subsequent retention of fibroblast cells in the infarct zone. Therapeutic agents are delivered to the infarct zone such as growth factors and pro-fibroblastic agents to recruit surrounding fibroblasts to the area. These agents may be delivered by microparticles harboring these therapeutic agents or direct delivery of the therapeutic agents to the infarct region. The naturally occurring fibroblasts that infiltrate the infarct region may be stimulated to proliferate in addition to recruiting new fibroblasts to the region. In other embodiments, these fibroblasts may be encouraged to convert from a non-contractile cell to a muscular cell by delivering growth factors to the infarct region such as transforming growth factors-$\beta1$. This retention of fibroblasts in the infarct zone is suitable for reinforcing the region and preventing the thinning process of the ventricular wall.

Other embodiments directed to the prevention of thinning of the infarct region of the ventricle wall are included. Treatment agents that are capable of cross-linking the existing collagen in the infarct region are described. The cross-linked collagen would form a structurally reinforcing wall in the infarct region to bulk-up the infarct zone and reduce the effects of thinning.

In another embodiment, a method includes multi-component treatments of the infarct zone. One multi-component method includes the formation of a scaffold to facilitate the attachment of fibroblasts and to deliver growth factors and other treatment agents. In addition, the in-growth of new capillaries is encouraged by the sustained release of angiogenic factors by the microparticles that form the scaffold. The treatment agents may be released for up to two months period. This technique would offer maximum benefit for the regeneration of viable tissue.

In another embodiment, a different multi-component treatment of the infarct zone introduces a scaffold system that provides a matrix to facilitate cell growth and inhibit the remodeling event post-MI. In addition the treatment includes a perfluorinated compound that enhances the re-oxygenation of the tissue In another embodiment, the blood that rapidly infiltrates the infarct region may be clotted. The clotting of the blood by various agents, for example fibrin glue, would result in a mass. This clot would also provide reinforcement of the wall and prevention of the thinning process. The intervention of the thinning process by clotting must occur within four hours of the MI but would provide early structural reinforcement of the infarct zone.

In another embodiment, a solution is delivered to a site in a ventricle. The solution contains an agent(s) capable of precipitating at a region for reinforcement of that region. Another solution contains one or more agents that are delivered to a region in a ventricle and remain in that region while the supporting solution dissipates into surrounding tissue.

In one embodiment, the treatments proposed may occur at any time after an infarction. In another embodiment, the treatments proposed may occur within seven weeks of an MI event (or prior to myocyte replacement). In another embodiment, the treatments proposed may occur within two weeks of an MI event.

In a further embodiment, a kit is disclosed. One example of such a kit is a kit including an injectable composition having the property of forming a gel once introduced to the treatment area. The gel may be formed due to one or more environmental changes or alternatively a response to one or more internal components.

BRIEF DESCRIPTION OF THE DRAWINGS

The methods and compositions are illustrated by way of example, and not limitation, in the figure of the accompanying drawings in which:

FIG. 1A illustrates a longitudinally sectioned healthy artery and blood flow therein.

FIG. 1B illustrates a longitudinally sectioned damaged artery due to a tear or a spasm.

FIG. 1C illustrates a longitudinally sectioned occluded artery due to fat and cholesterol build up.

FIG. 2A illustrates plaque build up in an artery that may result restriction of blood and oxygen flow to the heart FIG. 2B illustrates the damage to the heart as a result of the plague build-up in an artery that lead to an MI.

FIG. 3I illustrates an example of the myocardium a couple of weeks after a myocardial infarction. A lot of collagen has been deposited at the site of damage.

Table 1 illustrates a few examples of biocompatible perfluorinated compounds.

Figure 6:
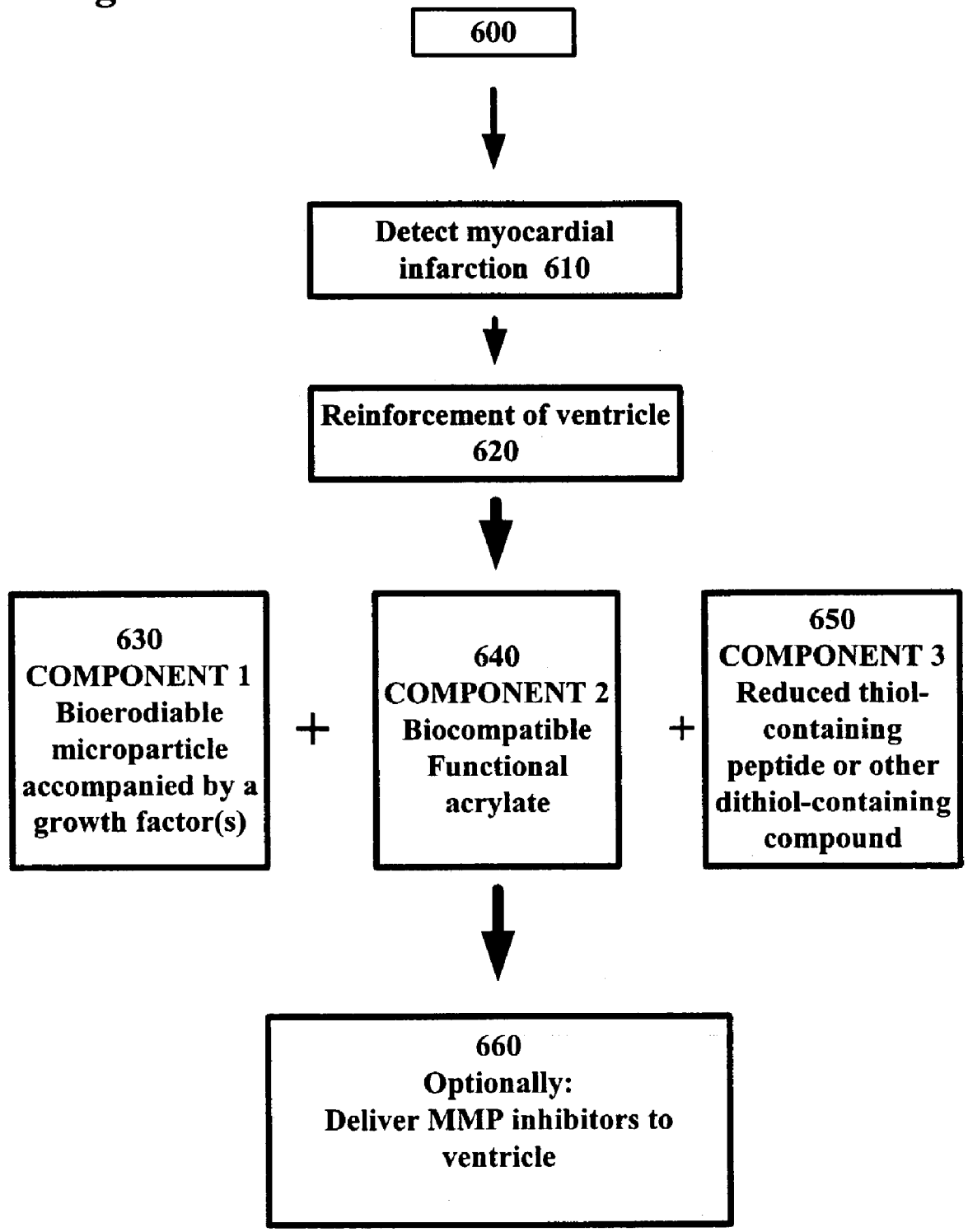
FIG. 6 illustrates a multi-component method for structurally reinforcing an infarct region.
Figure 7:
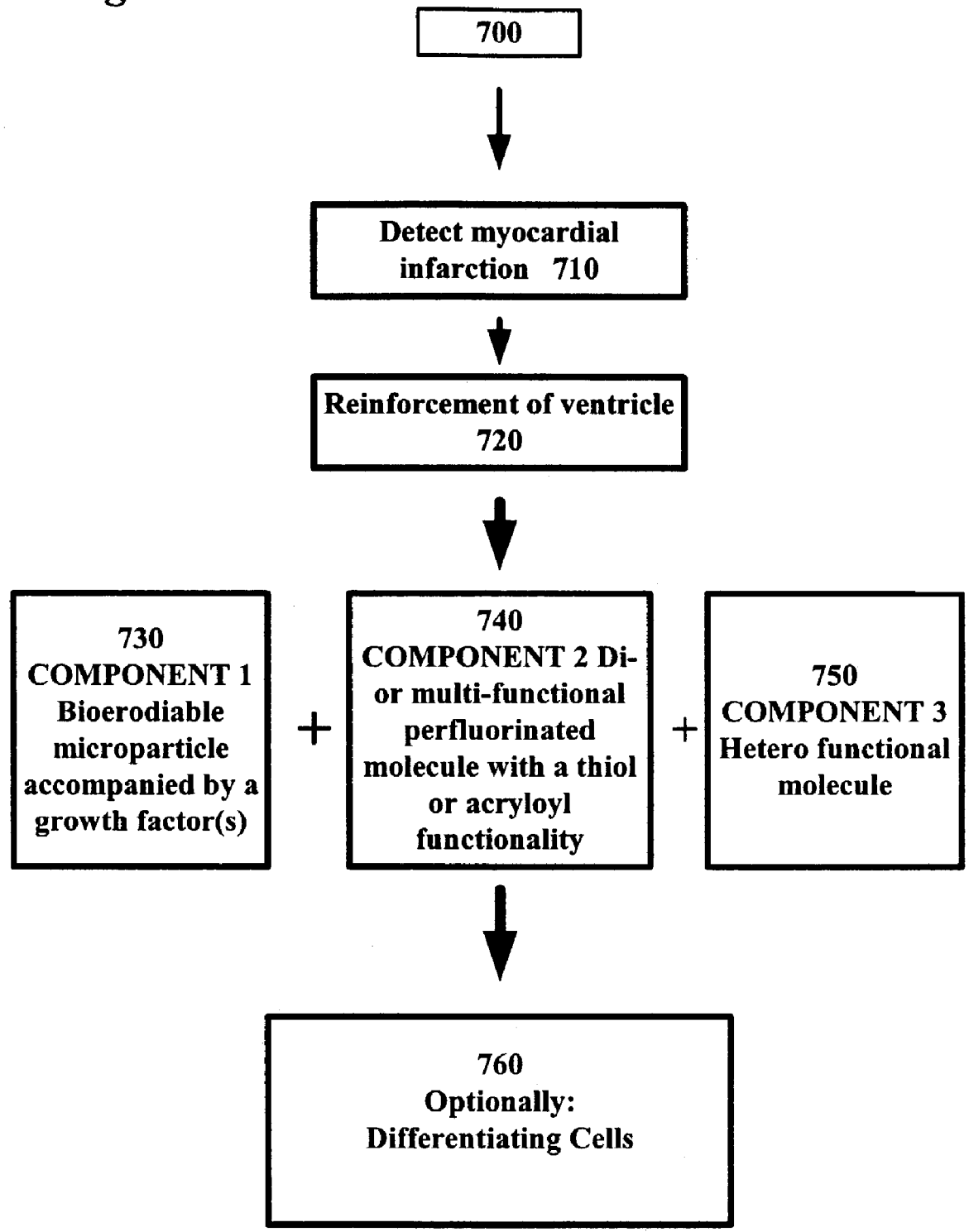
FIG. 7 illustrates a multi-component method for structurally reinforcing an infarct region and/or facilitating oxygenation of an infarct region.

FIG. 9A-F illustrates introduction and action of the multi-component method for structural reinforcement to an infarct region for example FIG. 6 and/or FIG. 7.

Figure 8:
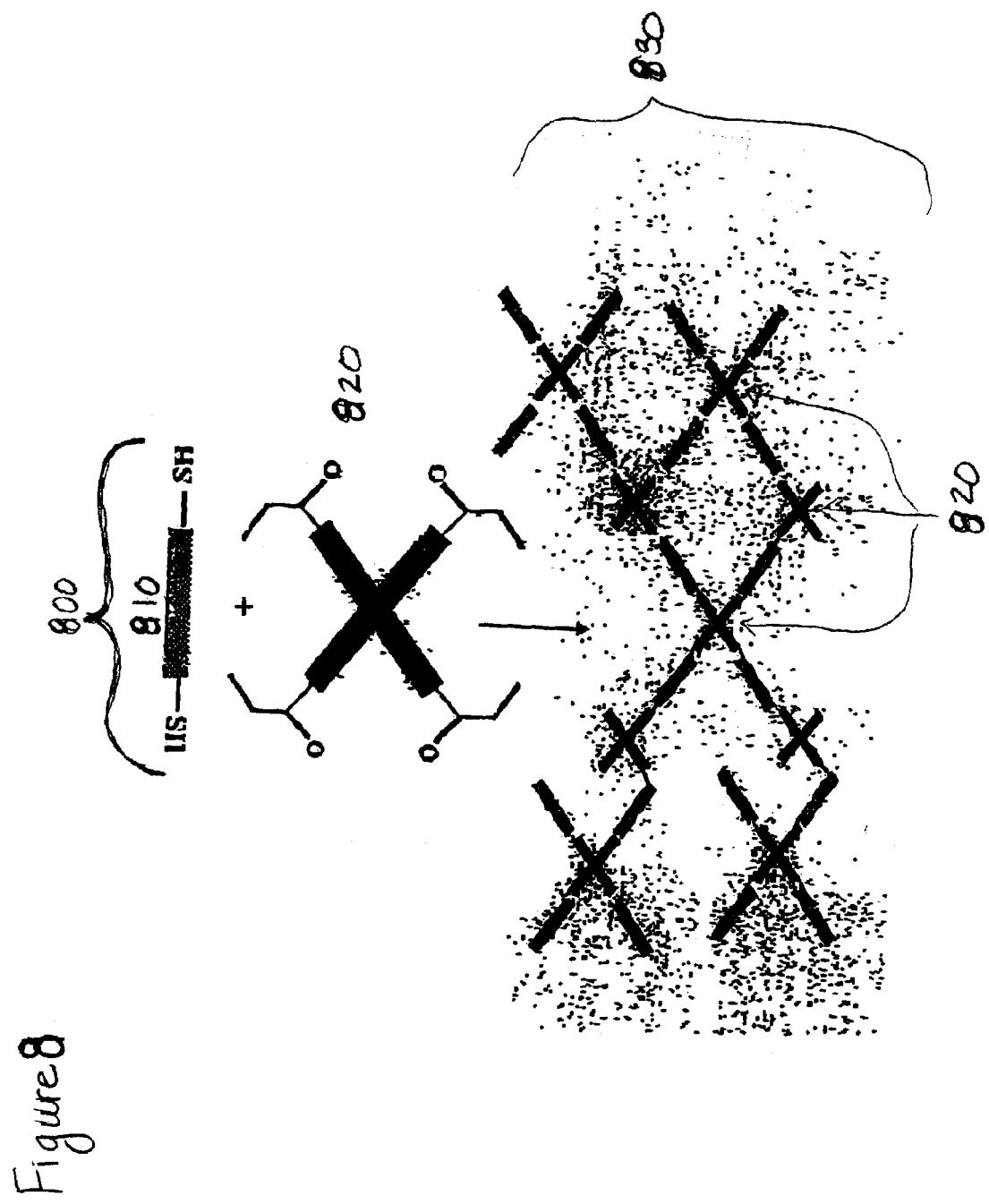
FIG. 8 illustrates a general structure of the first and of the second component of FIG. 7.
Figure 10:
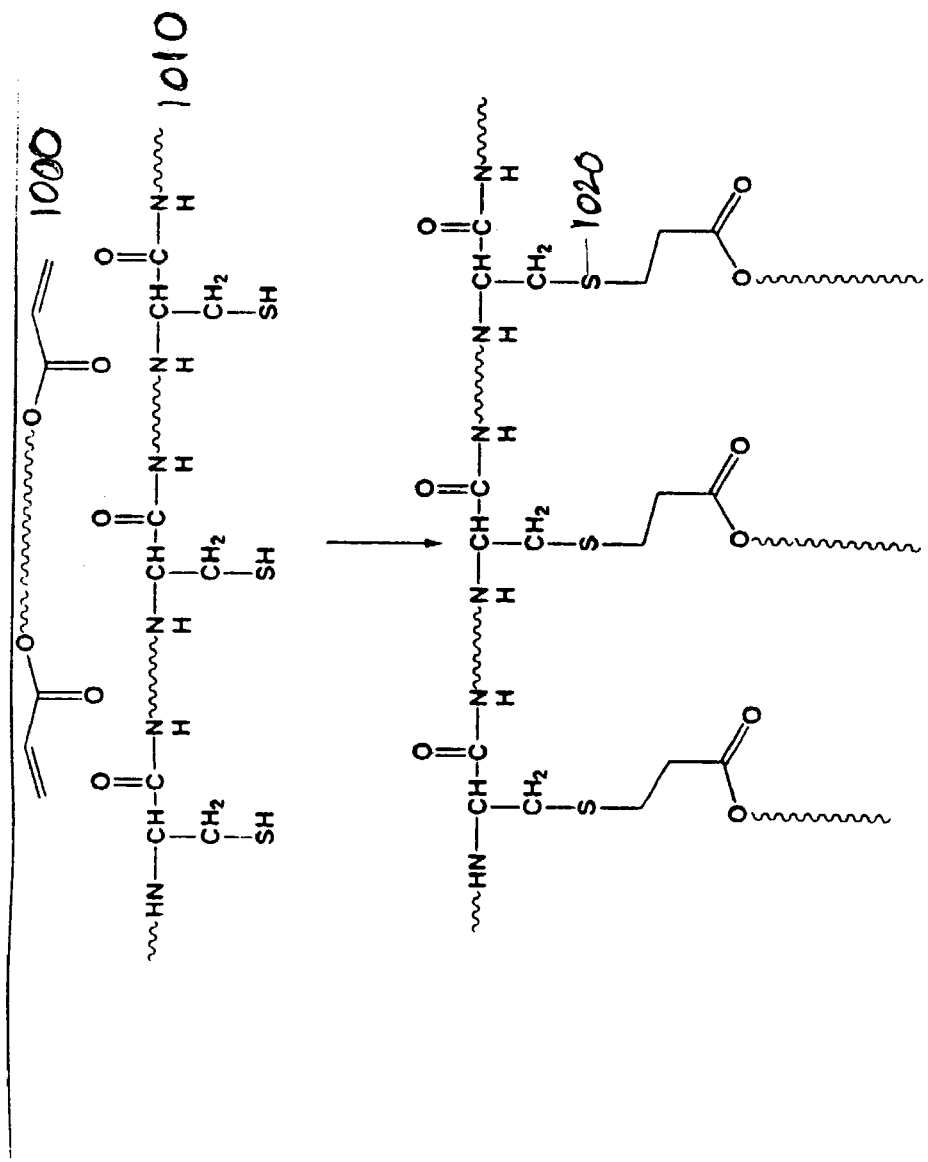

FIG. 10 illustrates an ester bond formed by at least two of the components of embodiments illustrated in FIG. 7 and FIG. 8.

FIG. 11A-11F illustrates introduction of structural reinforcement in the form of swellable microparticles to an infarct zone.

Figure 12:
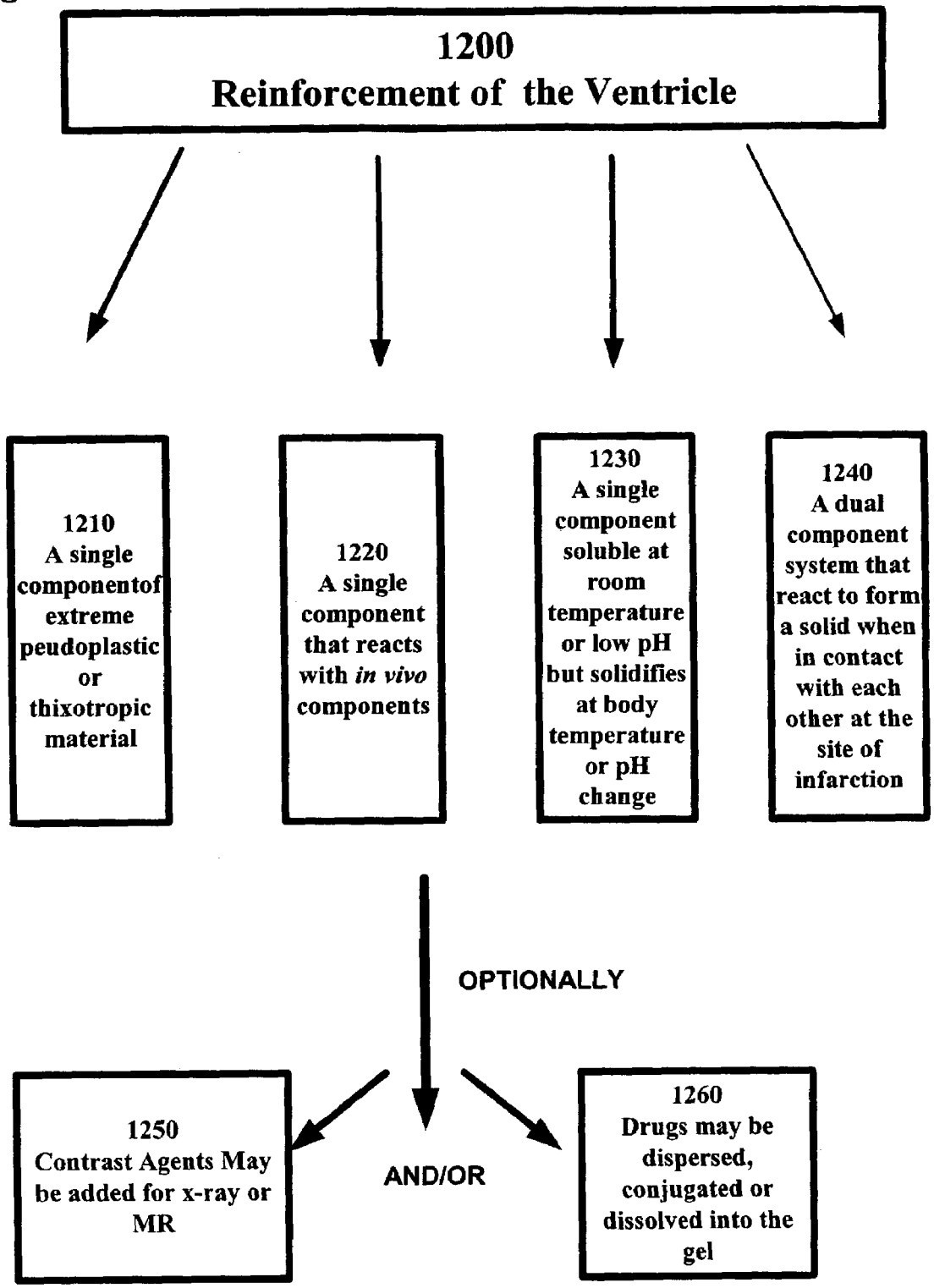

FIG. 12 illustrates a flowchart of the several possible structural reinforcing agents that may be introduced to an infarct region.

Figure 13:
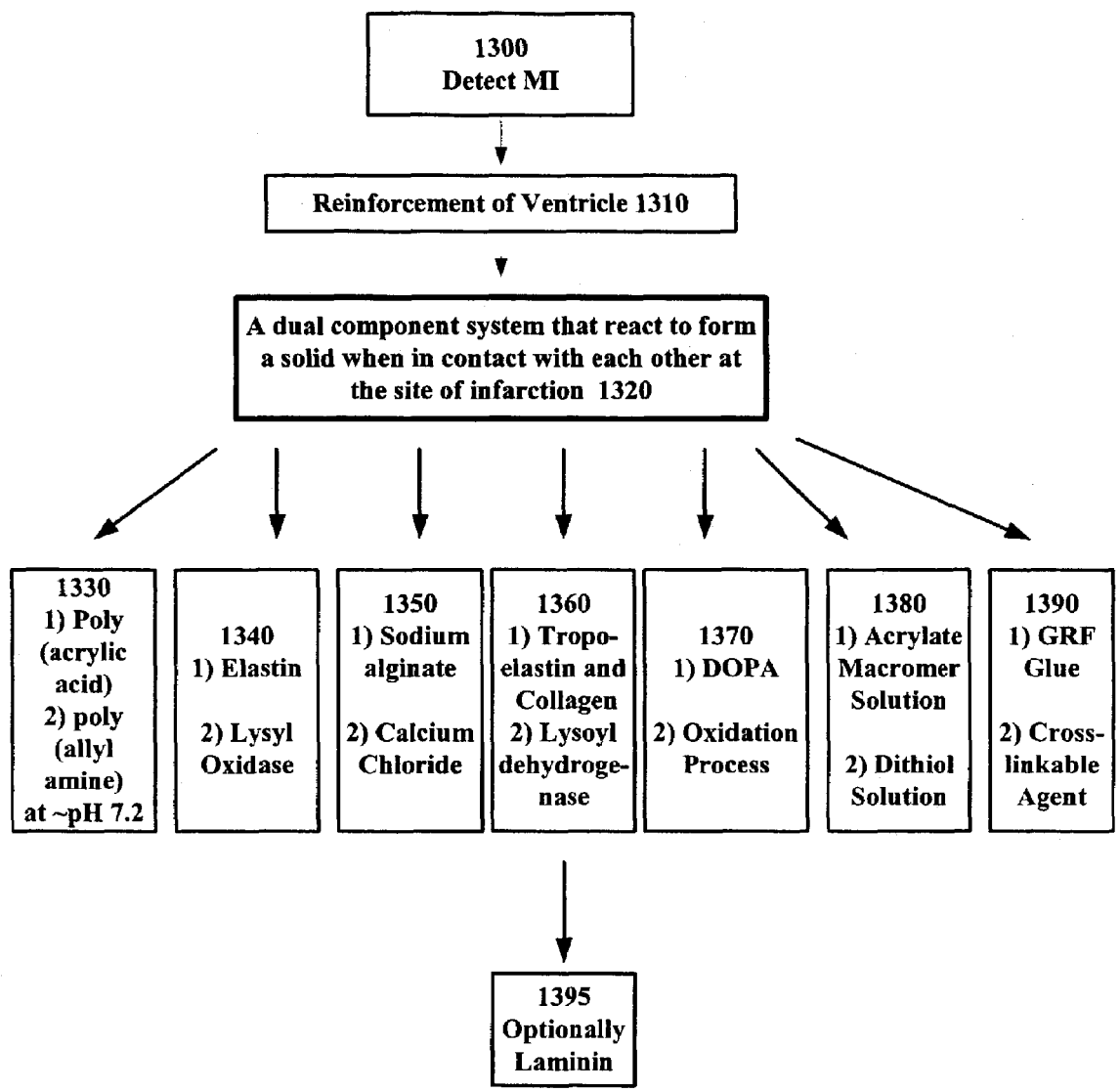

FIG. 13 illustrates an expansion of FIG. 12 1240 disclosing possible dual component systems.

Figure 14:
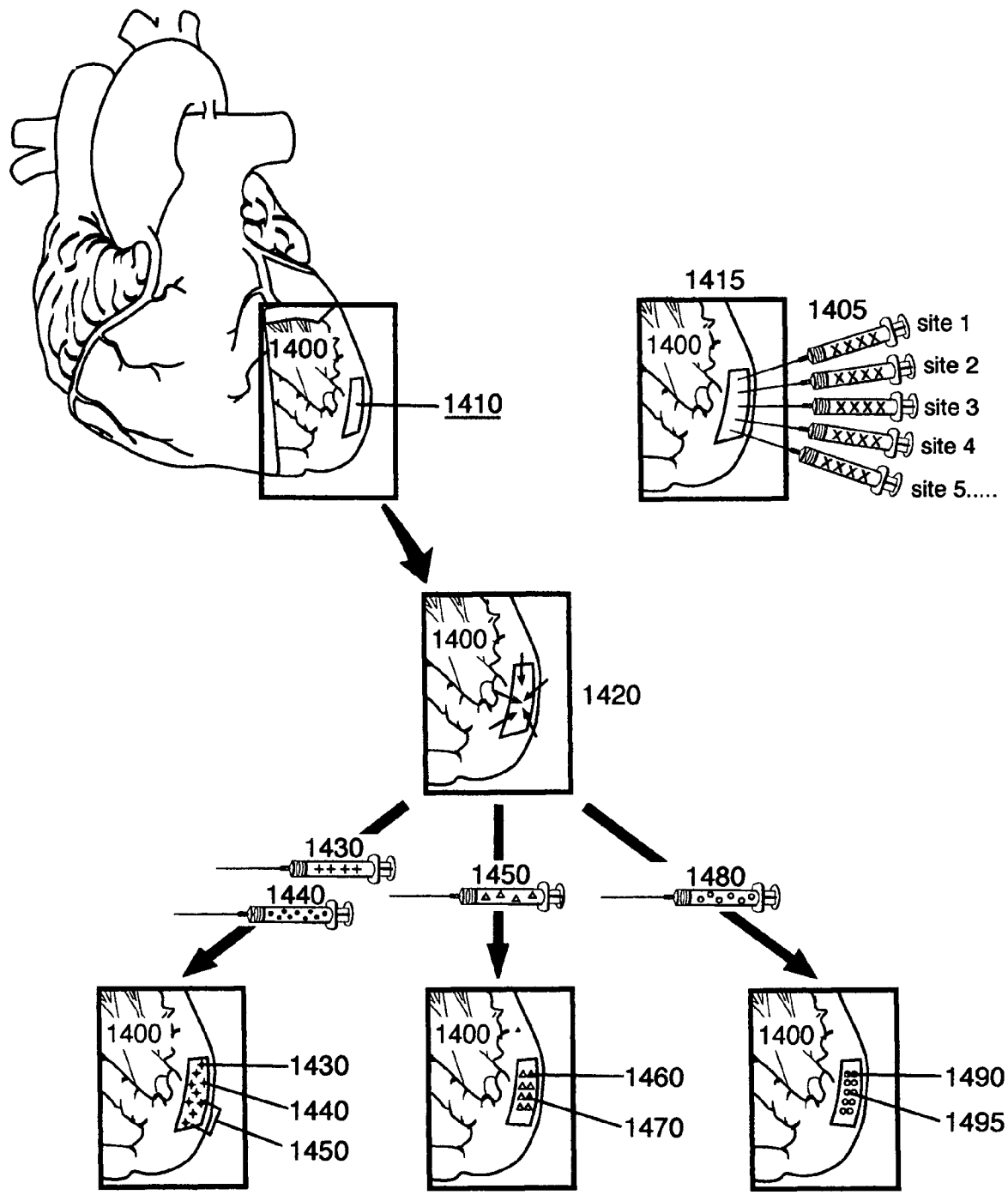

FIG. 14 illustrates introduction and action of the methods illustrated in the flowchart of FIG. 13 in an infarct region.

Figure 15:
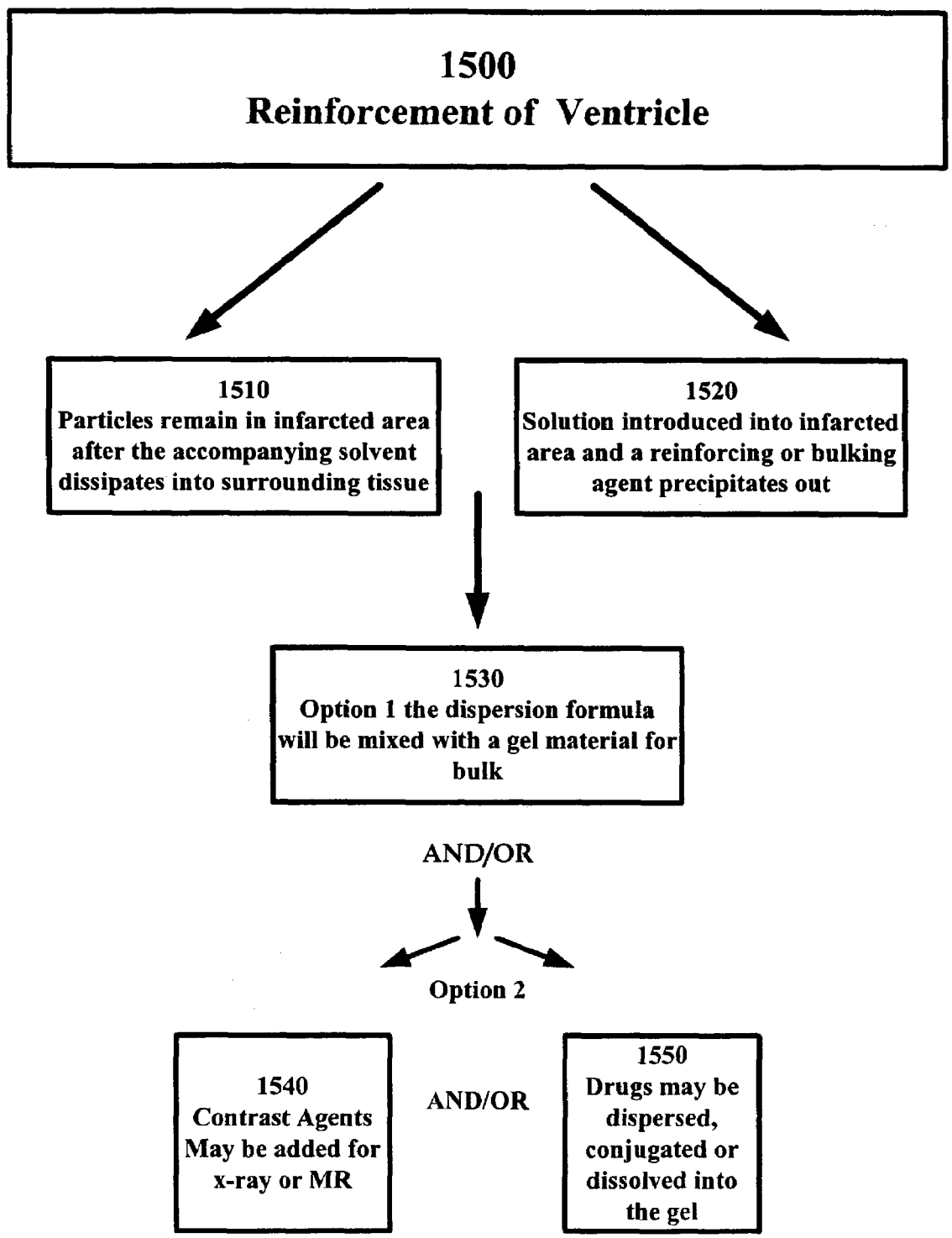

FIG. 15 illustrates two possible methods to structurally reinforce an infarct zone by bulking up a region.

Figure 16:
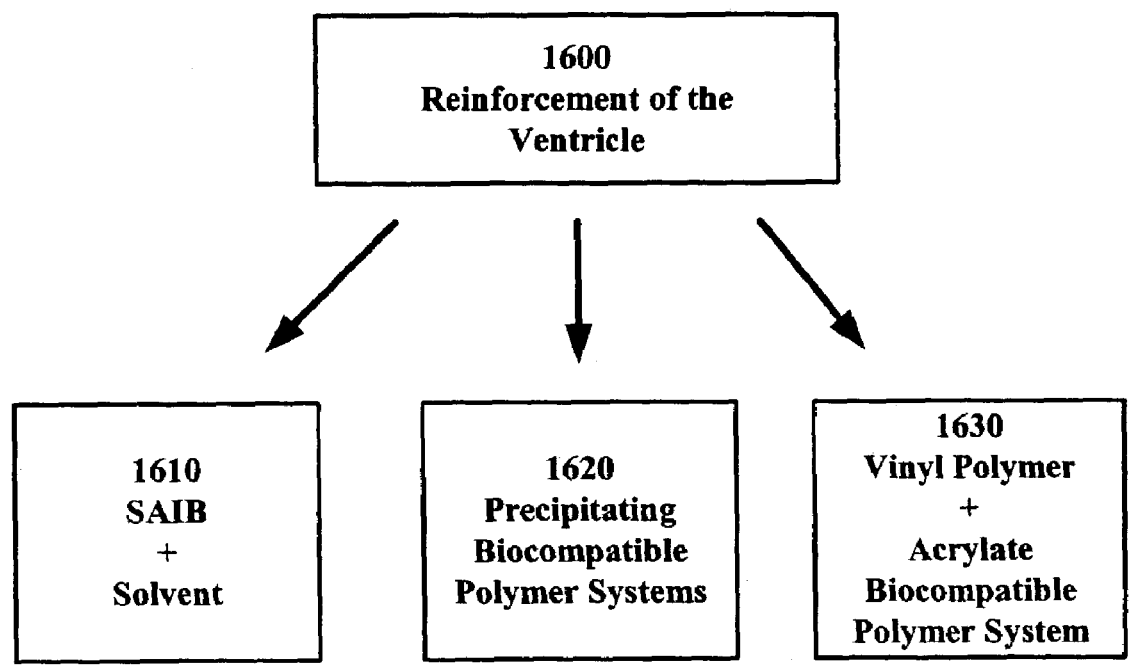

FIG. 16 illustrates examples of bulking agents that may structurally reinforce an infarct region.

Figure 17:
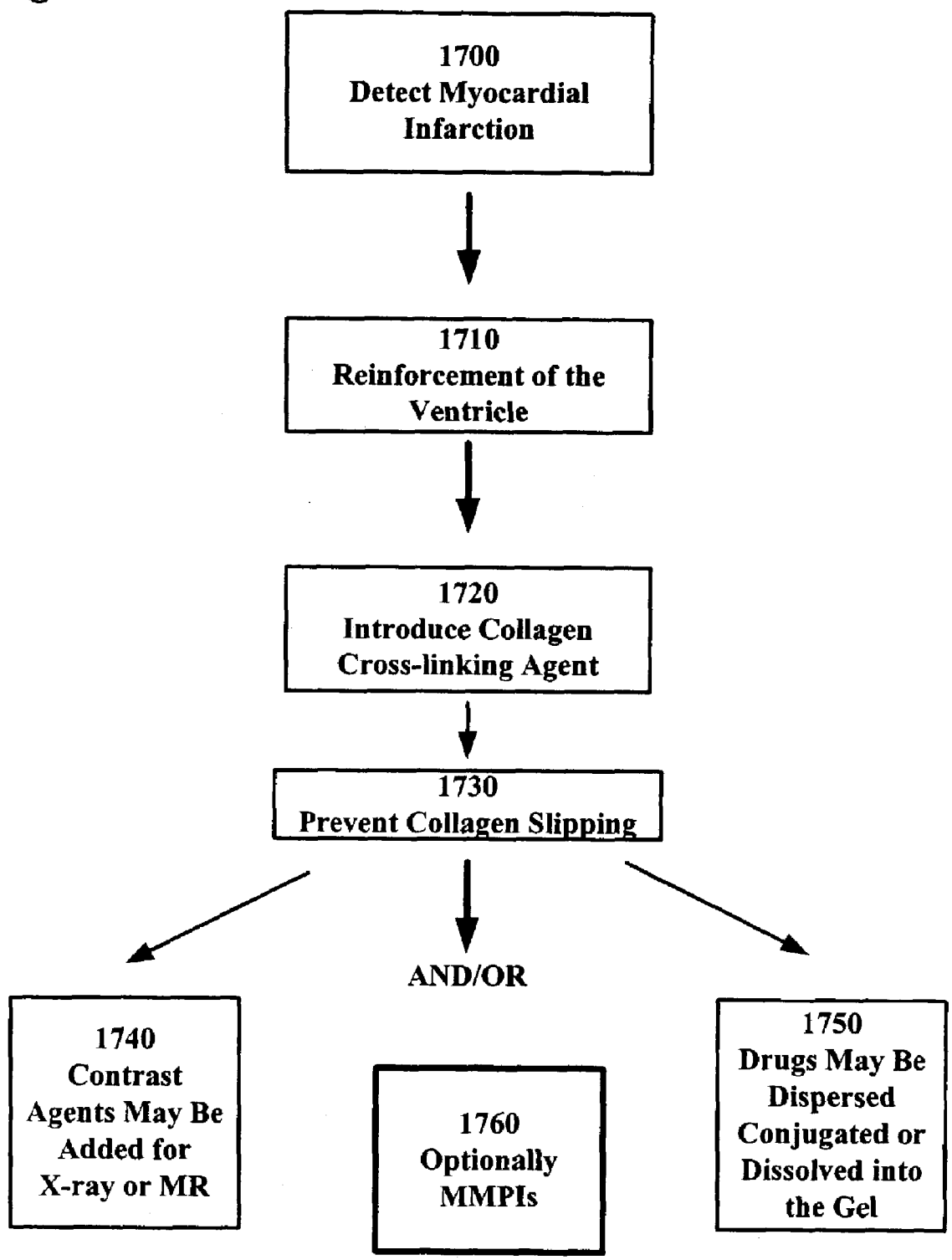

FIG. 17 illustrates stabilizing the collagen in an infarct zone by cross-linking.

Figure 18:
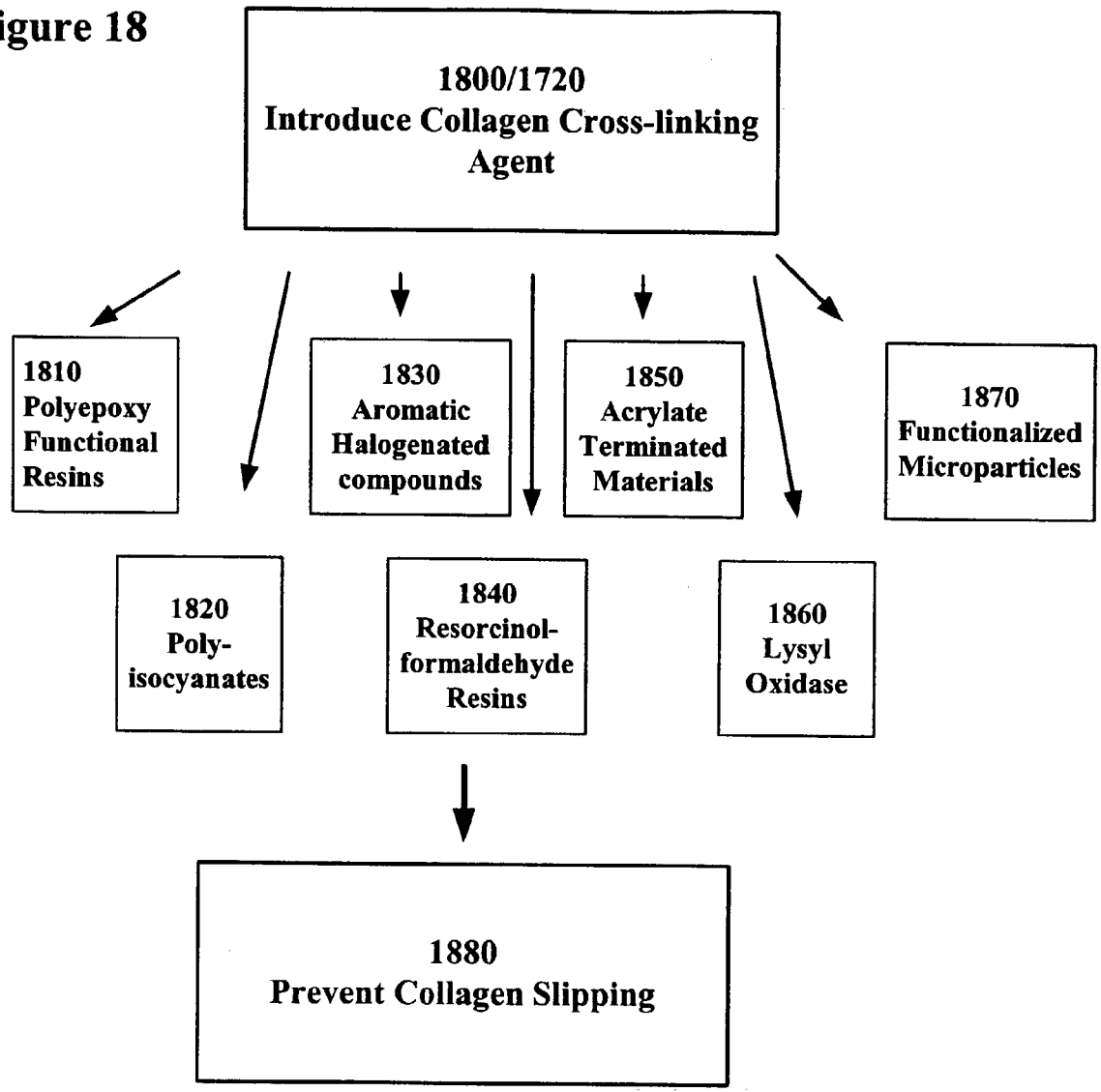

FIG. 18 illustrates various agents that may cross-link the collagen in an infarct region.

Figure 19:
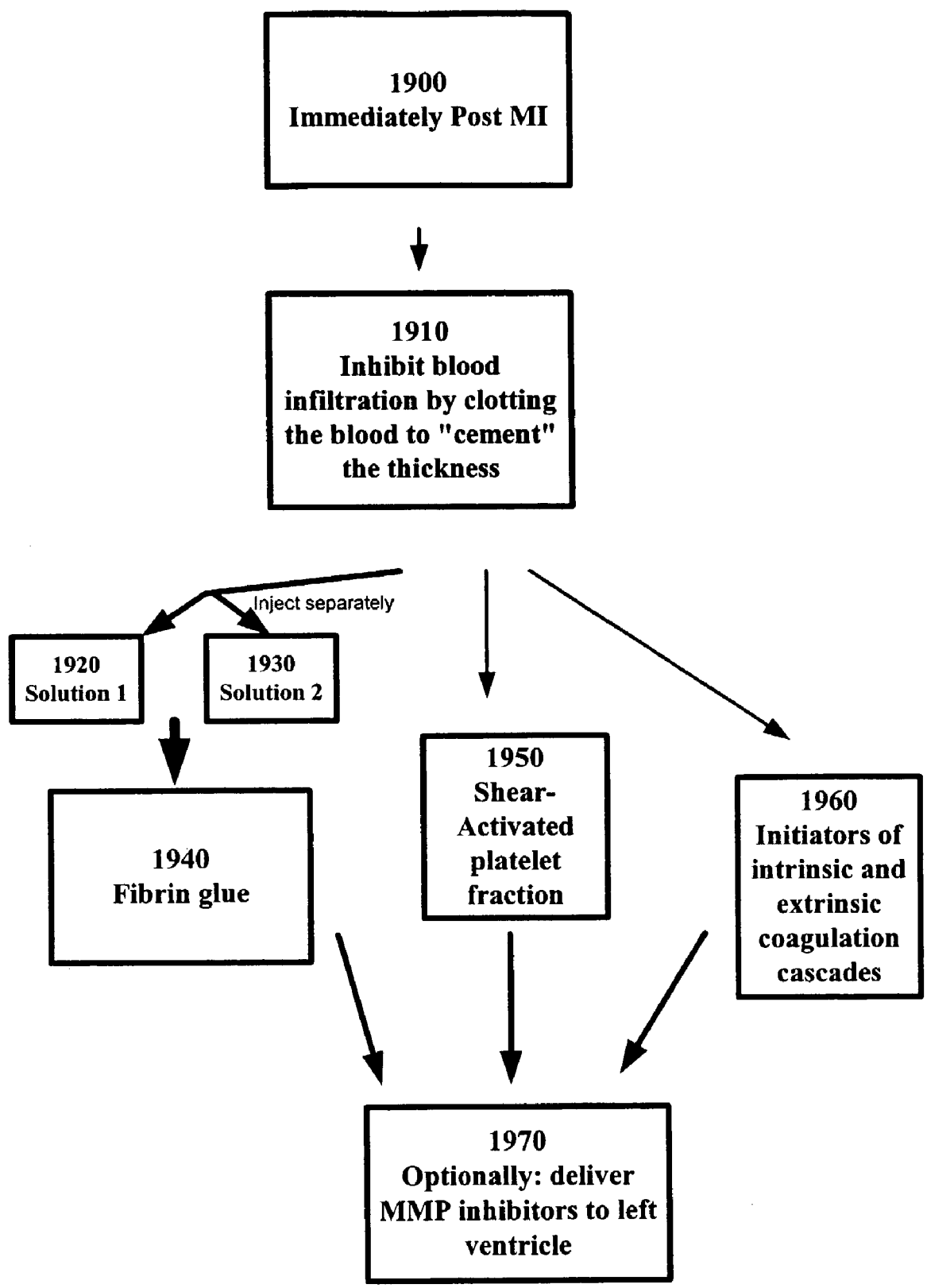

FIG. 19 illustrates various embodiments to clot the blood in an infarct region post MI.

Figure 20:
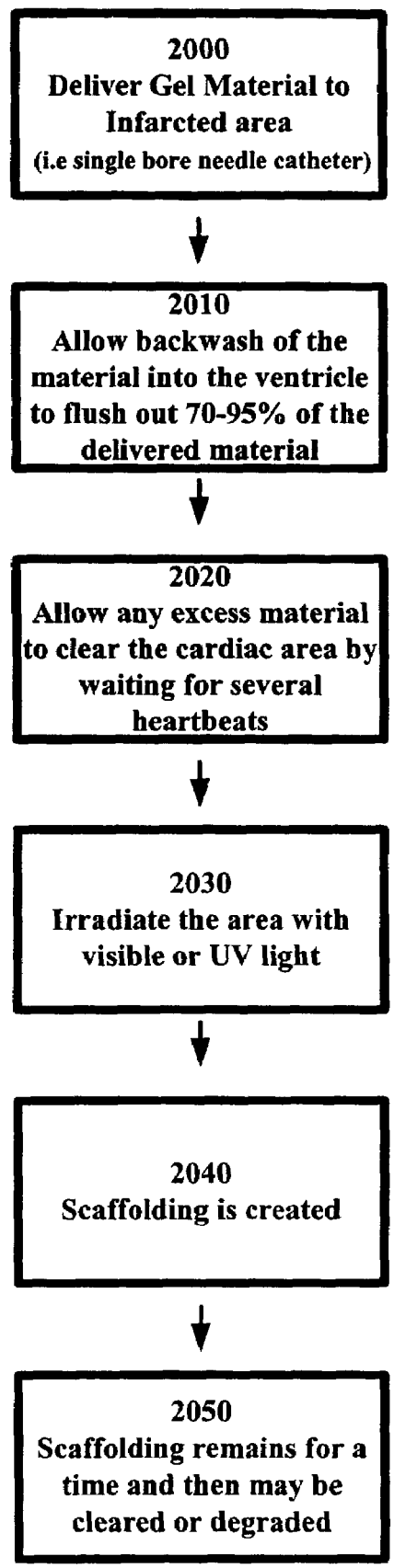

FIG. 20 illustrates various methods to reinforce an infarct region using light sensitive components.

FIG. 21A-21E illustrates a cross-sectional view of introduction of an embodiment using a photo-polymerizable component of FIG. 20 to an infarct region.

Figure 22A:
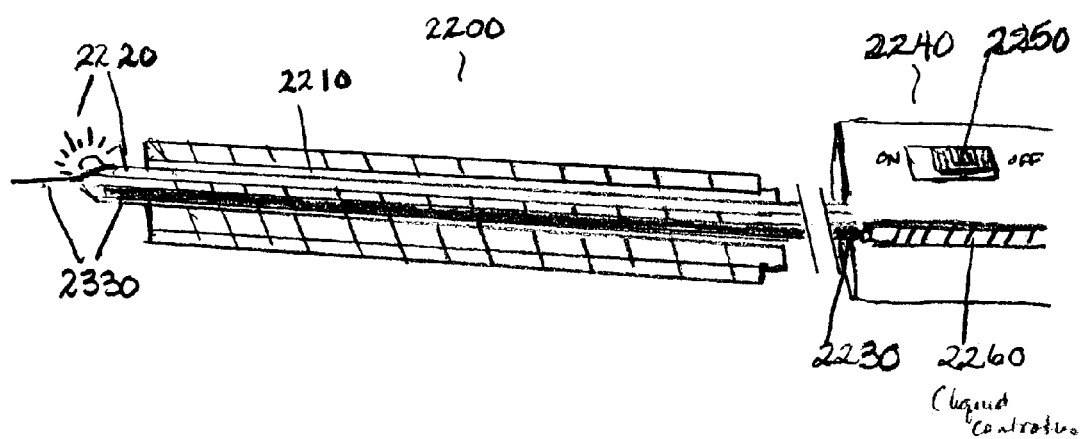

FIG. 22A illustrates a longitudinal view of a catheter device that has a light source and at least one component lumen.

Figure 22B:
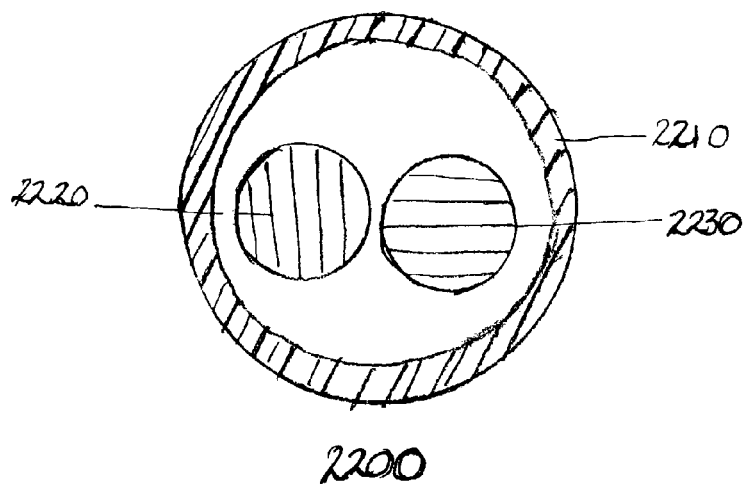

FIG. 22B illustrates a cross-sectional view of a catheter device that has a light source and at least one component lumen.

Figure 23:
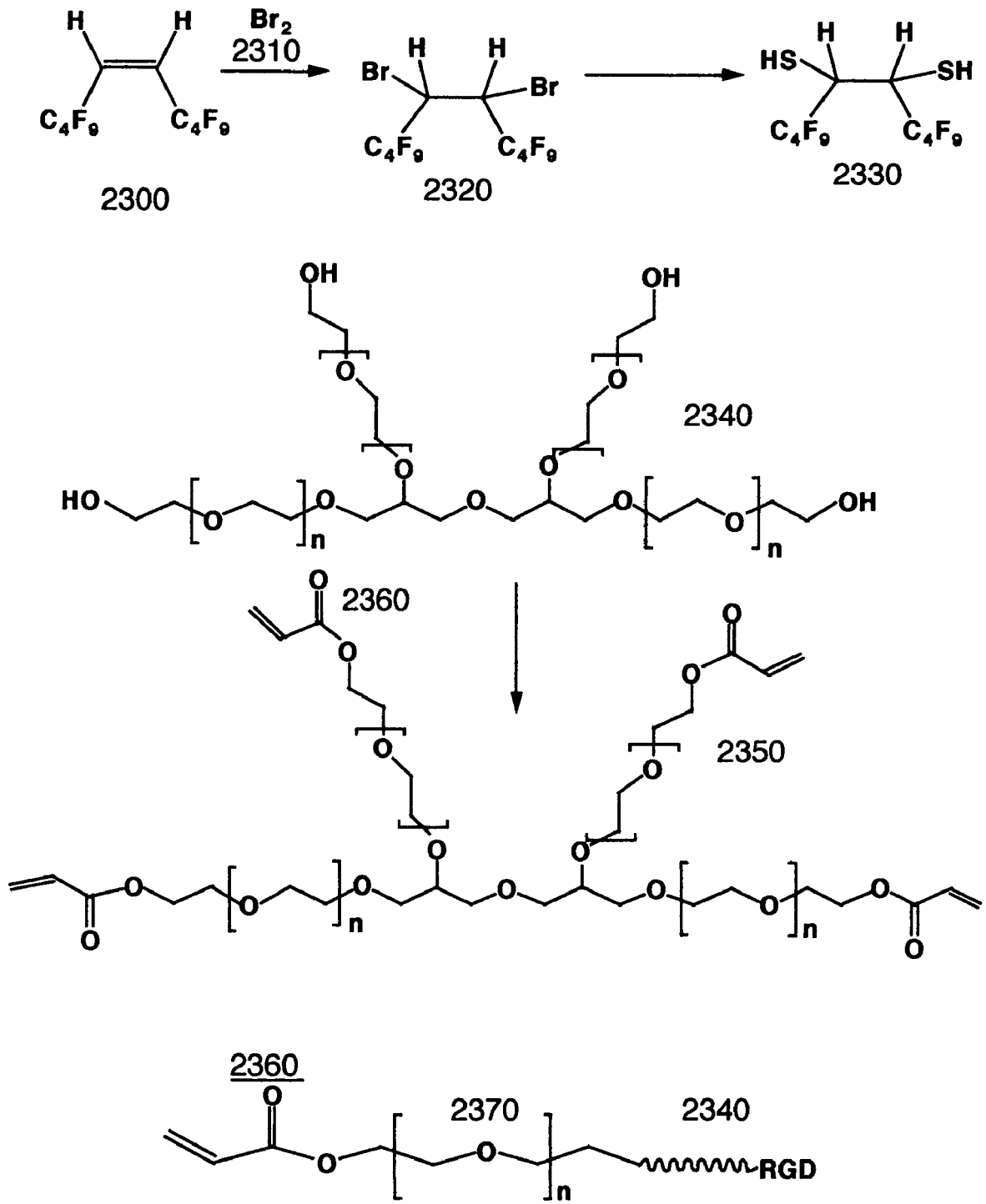
Figure 24A:
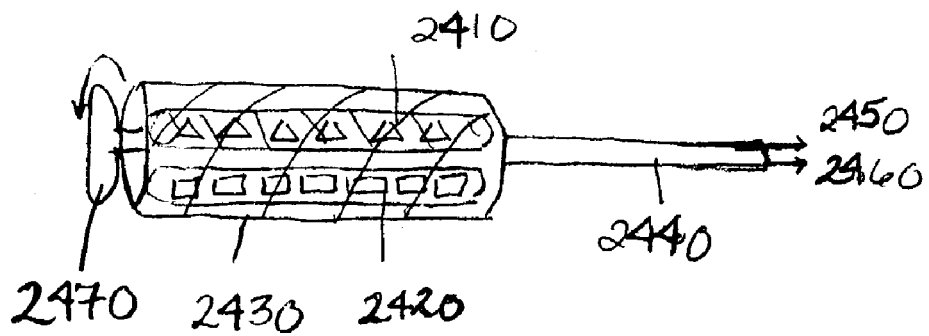

FIG. 23 illustrates one example of a multi-component method to reinforce the infarct region and/or re-oxygenate the infarct region FIG. 24A illustrates a longitudinal view of a catheter device that has two delivery ports and a control mechanism to deliver one component prior the second component.

Figure 24B:
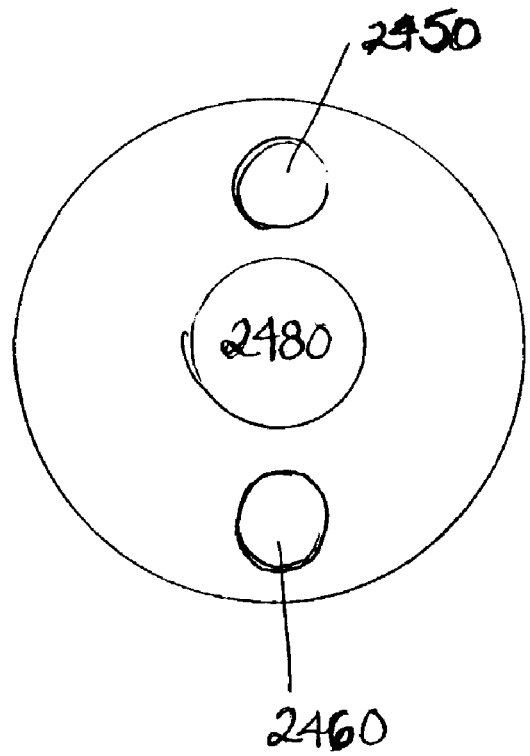

FIG. 24B illustrates a front view of the distal end of a catheter device with two delivery ports.

Figure 24C:
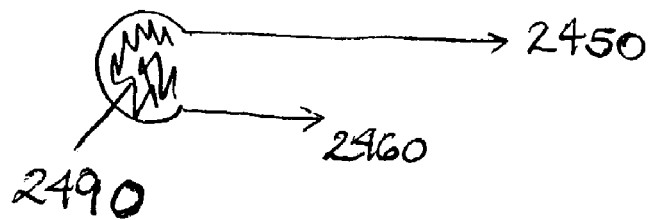

FIG. 24C illustrates the distal end of a catheter device where one delivery port may be extended while the second port may be confined to the housing of the catheter.

FIG. 25A-25D illustrates the introduction of two separate components into an infarct region of the ventricle and formation of a structurally reinforcing composition at the infarct region using a catheter with retractable dual delivery ports.

FIG. 26 illustrates the introduction of one component through a vein and the second through an artery using the catheter with retractable dual delivery ports.

DEFINITIONS

"a container" A receptacle, such as a carton, can, vial, tube, bottle, or jar, in which material is held or carried.

"cardiomyocyte-like"—a cell(s) capable of converting to a cardiomyocyte(s) or a cell or components capable of functioning like a cardiomyocyte.

"polymer-forming"—any agent or agents capable of forming a gelatinous material either alone or in combination.

"delivery device"—an apparatus or system capable of depositing a solution, powder, concentrate, a single reagent and/or multiple reagents.

"pro-fibroblastic" agent—one or more compounds capable of retaining, inducing proliferation of and/or recruiting fibroblasts cells.

"compliance"—The ability of a blood vessel or a cardiac chamber to change its volume in response to changes in pressure has important physiological implications. In physical terms, the relationship between a change in volume (D V) and a change in pressure (D P) is termed compliance (C), where C=DeltaV/Delta P.Compliance, therefore, is related to the ease by which a given change in pressure causes a change in volume. In biological tissues, the relationship between DV and DP is not linear. Compliance is the slope of the line relating volume and pressure that decreases at higher volumes and pressures. Another way to view this is that the "stiffness" of the chamber or vessel wall increases at higher volumes and pressures. Changes in compliance have important physiological effects in cardiac chambers and blood vessels.

DETAILED DESCRIPTION

In the following section, several embodiments of, for example, processes, compositions, devices and methods are described in order to thoroughly detail various embodiments. It will be obvious though, to one skilled in the art that practicing the various embodiments does not require the employment of all or even some of the specific details outlined herein. In some cases, well known methods or components have not been included in the description in order to prevent unnecessarily masking various embodiments.

Methods and compositions to treat a ventricle after a myocardial infarction (MI) are disclosed. In one embodiment, the infarct region or the area of the ventricle containing the infarct injury may be treated alone or in combination with other treatments. One benefit to such treatment is that the region of injury may be targeted with little or no affect on the outlying healthy heart tissue. In addition, another benefit of such treatment is that the treatment may prevent the loss of functionality of a region of injury due to the normal remodeling and scar forming procedure to mend an infarct region. Another benefit may be that the treatment may increase the compliance of the ventricle. Still another benefit is the reduction in thinning of a ventricular wall of an infarct zone. In the following description, structural reinforcement of the infarct region of the ventricle is described. Since most myocardial infarctions occur in the left ventricle most descriptions will be directed towards left ventricle repair. But, it is appreciated that treatment of the right ventricle may be achieved in a similar manner.

If the remodeling of the infarct region could be modified prior to scar formation and ultimate thinning of the ventricular wall, functional tissue may be rescued. The inhibition of scar formation and guided regeneration of viable cells would lead to increased wall strength and decreased collagen deposition, instead of thinning and hypertrophied myocytes. Further, decreasing the probability of wall thinning and fortifying the influx of structural components such as fibroblasts might be beneficial and preferred over the current treatment of an MI, namely continual exposure to systemic drugs to treat the symptoms and not the disease. Another benefit may be that any one of the treatments herein may result in an increase in compliance of the ventricle. Thus, any one or more combinations of these treatments may provide a potential for healing the infarct region and prevention of further complications.

In other embodiments, a kit (e.g., a pre-manufactured package) is disclosed. A suitable kit includes at least one agent and a lumen to house the agent. The agent has a property that may increase the modulus (tensile strength, "stiffness") of elasticity of the infarct region, increase compliance of the ventricle and/or prevent or reduce thinning caused by remodeling. The kit may be suitable, in one example, in the methods described.

Mapping of the Heart

In each of the methods described herein, it is appreciated that specific areas of the heart may be targeted for application of any of the incorporated methods, thus there are techniques previously described that may be used for targeting the infarct region. One example of targeting a specific region such as an infarct zone uses a technique known as mapping the heart (U.S. Pat. No. 6,447,504). The data are acquired by using one or more catheters that are advanced into the heart. These catheters usually have electrical and location sensors in their distal tips. Some of the catheters have multiple electrodes on a three-dimensional structure and others have multiple electrodes distributed over a surface area. One example of the later catheter may be a sensor electrode distributed on a series of circumferences of the distal end portion, lying in planes spaced from each other. These techniques provide methods to characterize the condition of the heart in some situations using electrical potentials in the heart tissue as well as using electromechanical mapping, ultrasonic mapping to map the viable and the non-viable regions of the heart for example the left ventricle and the infarct zone. In addition, the ultrasound waves may be used to determine the thickness of the heart tissue in the vicinity of the probe for example, sensing the characteristic of the heart tissue by analyzing the ultrasound signals to determine the depth of the channels. Another method known as viability mapping (for example Spect, MRI, PET) may also be used. Viability mapping may be used to identify areas of the heart that are ischemic but still viable as well as area that have lost their viability due to infarction. These maps are based on electrophysiological data that indicate the flow of activation signals through the heart tissue. In addition, the data may be biomedical and/or mechanical data for example, variations in the thickness of the heart wall between systolic and diastolic stages of the heart cycle. The data that is used to analyze the heart by mapping may also be a combination of electrophysiological and biomedical data in order to more accurately locate and target the infarct region. In absence of viability mapping devices, it is appreciated that the location of the infarction may be also assessed through LV angiography or echo, where location of the akinetic or hypokinetic region may be identified.

Delivery Systems

Any one or more catheters may be used to deliver the any one or multiple components of the embodiments to the infarct region area. Several catheters have been designed in order to precisely deliver agents to a damaged region within the heart for example an infarct region. Several of these catheters have been described (U.S. Pat. Nos. 6,102,926, 6,120,520, 6,251,104, 6,309,370; 6,432,119; 6,485,481). The delivery device may include an apparatus for intracardiac drug administration, including a sensor for positioning within the heart, a delivery device to administer the desired agent and amount at the site of the position sensor. The apparatus may include, for example, a catheter body capable of traversing a blood vessel and a dilatable balloon assembly coupled to the catheter body comprising a balloon having a proximal wall. A needle may be disposed within the catheter body and includes a lumen having dimensions suitable for a needle to be advanced there through. The needle body includes an end coupled to the proximal wall of the balloon. The apparatus also includes an imaging body disposed within the catheter body and including a lumen having a dimension suitable for a portion of an imaging device to be advanced there through. The apparatus may further include a portion of an imaging device disposed within the imaging body adapted to generate imaging signal of the infarct region within the ventricle. The apparatus may be suitable for accurately introducing a treatment agent at a desired treatment site.

In another embodiment a needle catheter used to deliver the agent to the ventricle for example, the infarct region, may be configured to include a feedback sensor for mapping the penetration depth and location of the needle insertion. The use of a feedback sensor provides the advantage of accurately targeting the injection location. Depending on the type of agent administered, the target location for delivering the agent may vary. For example, one agent may require multiple small injections within an infarct region where no two injections penetrate the same site.

In other embodiments, the catheter assembly may include a maneuverable instrument. This catheter assembly includes a flexible assembly. The catheter assembly, may be deflectable and includes a first catheter, a second catheter, and a third catheter. The second catheter fits coaxially within the first catheter. At least one of the first catheter and the second catheter include a deflectable portion to allow deflection of that catheter from a first position to a second position, and the other of the first catheter and second catheter includes a portion which is preshaped (e.g. an angled portion formed by two segments of the angled portion). The third catheter has a sheath and a medical instrument positioned within the sheath. The third catheter fits coaxially within the second catheter. In another embodiment, a stabilizer, such as a donut shaped balloon, is coupled to a distal portion of the third catheter. Each catheter is free to move longitudinally and radially relative to the other catheters. The catheter assembly may be used but not limited to the local delivery of bioagents, such as cells used for cell therapy, one or more growth factors for fibroblast retention, or vectors containing genes for gene therapy, to the left ventricle. In one embodiment, the catheter assembly described may be used in delivering cell therapy for heart failure or to treat one or more portions of the heart that are ischemic. The catheter assembly uses coaxially telescoping catheters at least one or more being deflectable, to position a medical instrument at different target locations within a body organ such as the left ventricle. The catheter assembly may be flexible enough to bend according to the contours of the body organ. The catheter assembly may be flexible in that the catheter assembly may achieve a set angle according to what the medical procedure requires. The catheter assembly will not only allow some flexibility in angle changes, the catheter assembly moves in a three coordinate system allowing an operator greater control over the catheter assembly's movement portion of the second catheter, allowing for the distal tip of the third catheter to be selectively and controllably placed at a multitude of positions. It will be appreciated that the deflectable portion may alternatively be on the second catheter and the preshaped portion may be on the first catheter.

In a further embodiment, an apparatus is disclosed. In one embodiment, the apparatus includes a first annular member having a first lumen disposed about a length of the first annular member, and a second annular member coupled to the first annular member having a second lumen disposed about a length of the second annular member, wherein collectively the first annular member and the second annular member have a diameter suitable for placement at a treatment site within a mammalian body. Representatively, distal ends of the first annular member and the second annular member are positioned with respect to one another to allow a combining of treatment agents introduced through each of the first annular member and the second annular member to allow a combining of treatment agents at the treatment site. Such an apparatus is particularly suitable for delivering a multi-component gel material (e.g., individual components through respective annular members that forms a bioerodable gel within an infarct region of a ventricle).

In the embodiments described herein, a substance delivery device and a method for delivering a substance are disclosed. The delivery device and method described are particularly suitable, but not limited to, local drug delivery in which a treatment agent composition (possibly including multiple-treatment agents and/or a sustained-release composition) is introduced via needle delivery to a treatment site within a mammalian host. A kit of a treatment agent composition is also described. One suitable application for a delivery device is that of a catheter device, including a needle delivery system. Suitable therapies include, but are not limited to, delivery of drugs for the treatment of arterial restenosis, therapeutic angiogenesis, or cancer treatment drugs/agents.

In other embodiments, larger doses of treatment agent may be considered for example about 2 mls to about 250 mls that may require any one or more of the delivery devices such as intra-venous retro infusion, intra-arterial infusion and needle catheter systems (Invigor) as well as subxyphoid approaches.

Various apparati (devices) and methods described herein can be used as a stand-alone injection needle/catheter during a surgical procedure such as an open heart surgery (e.g., Coronary Bypass Graft (CABG)) procedure in which areas of the heart may be treated with, for example, growth factors, for affecting therapeutic angiogenesis, or incorporated into a catheter-based system to access locations that are commonly used in percutaneous translumena.1 coronary artery (PTCA) procedures. The apparati (devices) and methods may similarly be used in other surgical procedures such as cancer-related procedures (e.g., brain, abdomen, or colon cancer procedures or surgeries). Additionally, various apparati (devices) and methods described herein can be used in conjunction with various catheter-related or endoscopy procedures that generally require minimal invasiveness to deliver a specific drug or growth factor into tissue. Examples of such procedures include, but are not limited to, orthoscopic surgery for joints (e.g., knee), laparoscopic surgery for the abdomen, and thoroscopic procedures related to chest injuries or treatments.

One concern of introducing any treatment agent composition, whether adjacent a blood vessel to affect therapeutic angiogenesis, adjacent to a tumor to inhibit tumor growth, or to induce or stimulate collagen growth in orthroscopic procedures, is that the composition remain (at least partially) at the treatment site for a desired treatment duration (or a portion of the treatment duration). In this manner, an accurate dosage may be placed at a treatment site with reduced concern that the treatment agent will disperse, perhaps with serious consequences. In one embodiment, a composition and technique for retaining a treatment agent at a treatment site (injection site) is described. In one embodiment, a treatment agent and a bioerodiable gel or non-bioerodiable gel or particle may be introduced at a treat site (e.g., an injection site). The gel or particle(s) may be introduced prior to, after, or simultaneously with the treatment agent. In one preferred embodiment, the gel or particle(s) acts to retain the treatment agent at the treatment site by, representatively, sealing the treatment site or sealing the treatment agent at the treatment site. The use of a gel or particle(s) with a treatment agent can reduce the amount of treatment agent backflow from the injection site as well as reduce the load requirement of the treatment agent at the treatment site. For example, a bioerodable product such as a gel or particle may decrease the local pressure thereby further resulting in backflow reduction. A non-bioerodable product may also decrease the local pressure to reduce the backflow in a more permanent fashion and at the same time may also lead to an increase in compliance.

Using the above-mentioned techniques, an imaging modality may be added such as a contrast-assisted fluorescent scope that permits a cardiologist to observe the placement of the catheter tip or other instrument within the heart chamber. The contrast-assisted fluoroscopy utilizes a contrast agent that may be injected into heart chamber and then the area viewed under examination by a scope, thus the topography of the region is more easily observed and may be more easily treated (U.S. Pat. Nos. 6,385,476 and 6,368,285). Suitable imaging techniques include, but are not limited to, ultrasonic imaging, optical imaging, and magnetic resonance imaging for example Echo, ECG, SPECT, MRI, Angiogram. Therefore, mapping of the heart is one technique that may be used in combination with the techniques proposed in the following embodiments. In one embodiment, an echo angiograph may be performed to confirm the occurrence and the location of the infarct region. In another embodiment, a Cat Scan may be performed to confirm an MI has occurred and the location of the infarct region. In another embodiment an EKG may be performed to identify the occurrence and location of an infarct.

In another embodiment, a method may include introducing a treatment agent in a sustained release composition. The preferred period for sustained release of one or more agents is for a period of one to twelve weeks, preferably two to eight weeks. Methods for local delivery of sustained release agents include but are not limited to percutaneous devices for example intraventricular (coronary) or intravascular (coronary and periferal) devices.

A. Fibroblast Retention and Recruiting Agents

1. Agents

Figure 3A:
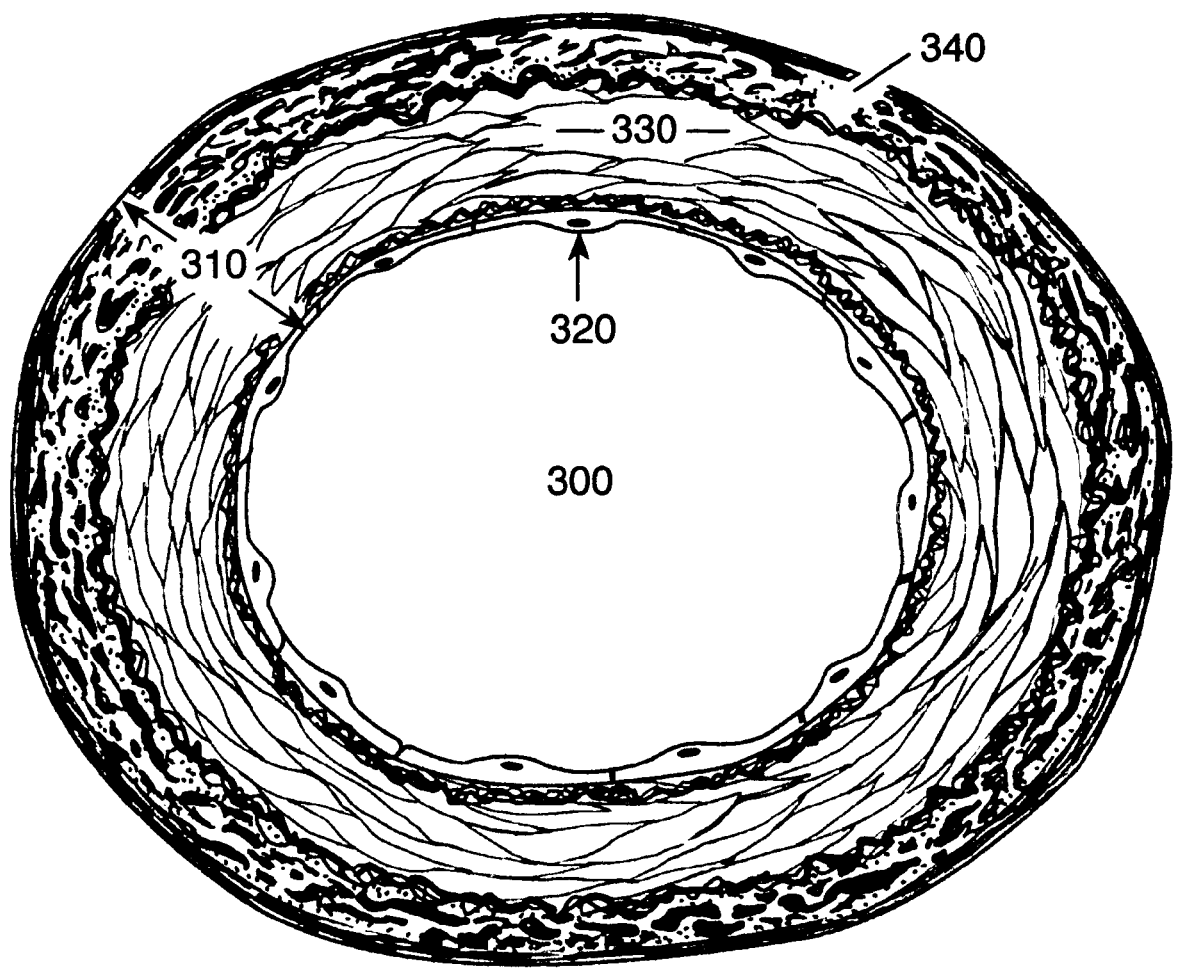
FIG. 3A illustrates a normal artery.
Figure 3B:
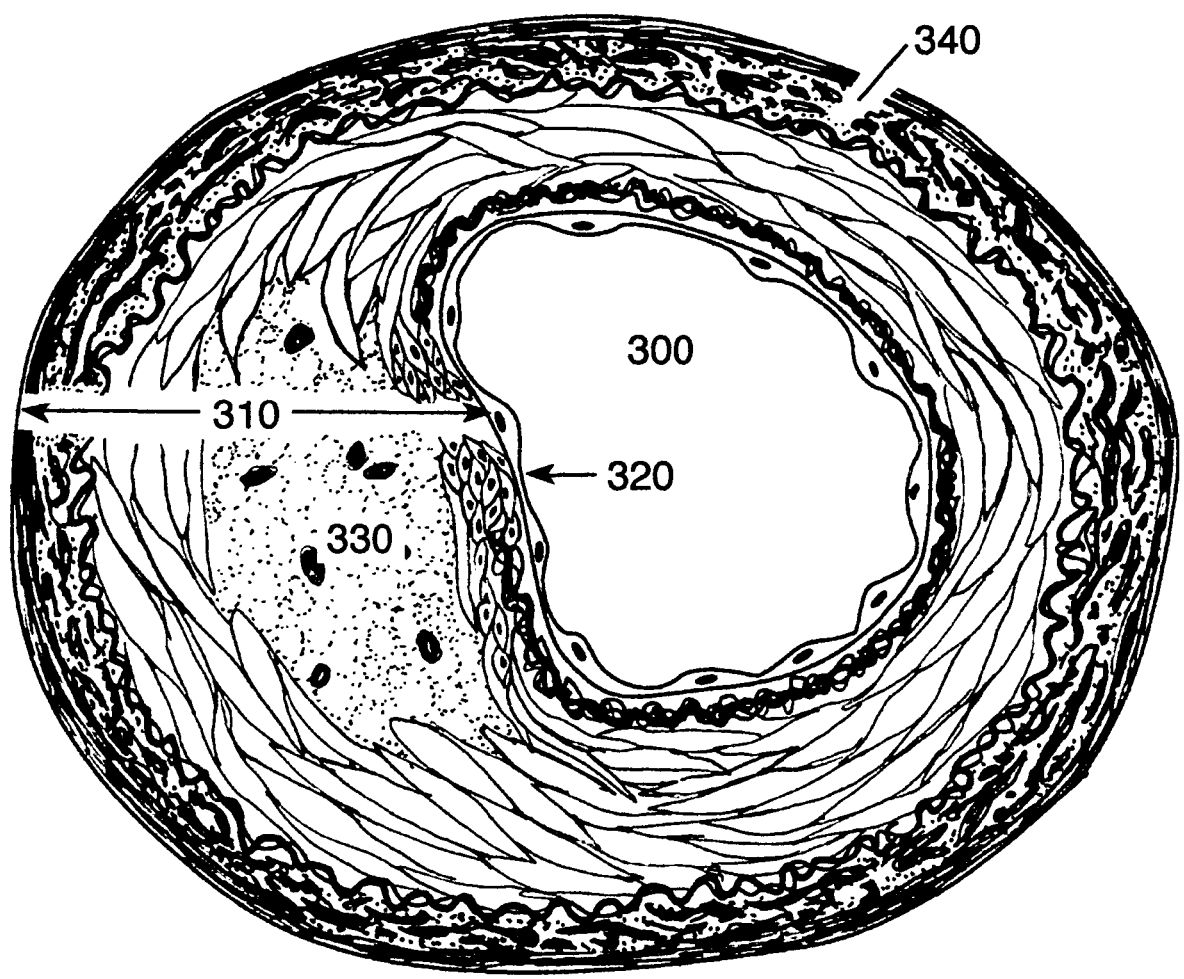
FIG. 3B illustrates an artery with arteriosclerosis (50 percent blockage) that may lead to an MI.
Figure 3C:
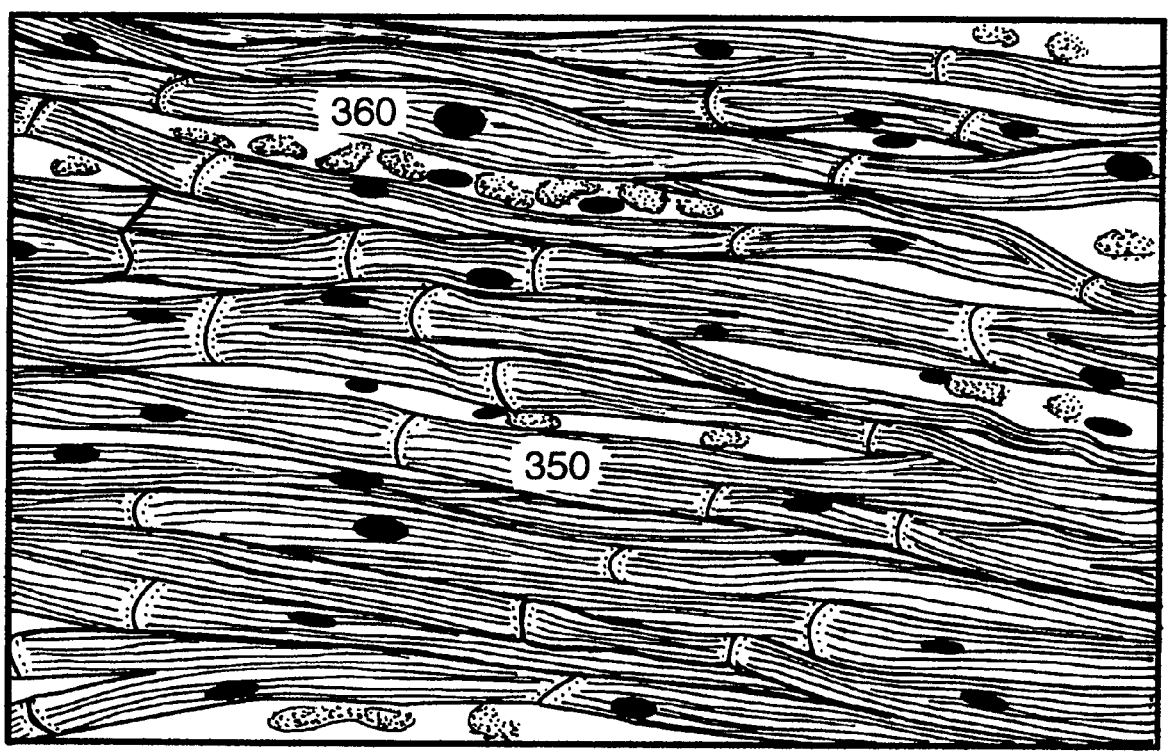
FIG. 3C illustrates normal myocardium.
Figure 3D:
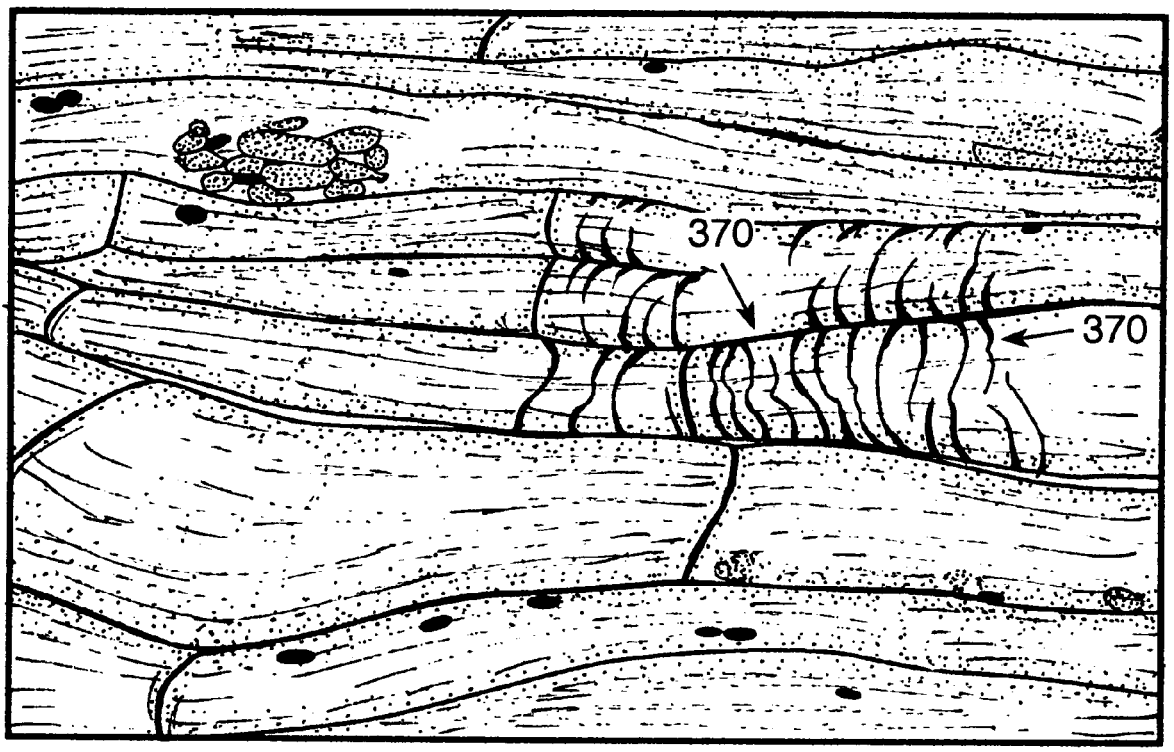
FIG. 3D illustrates an example of myocardium of an early acute myocardial infarction.
Figure 3E:
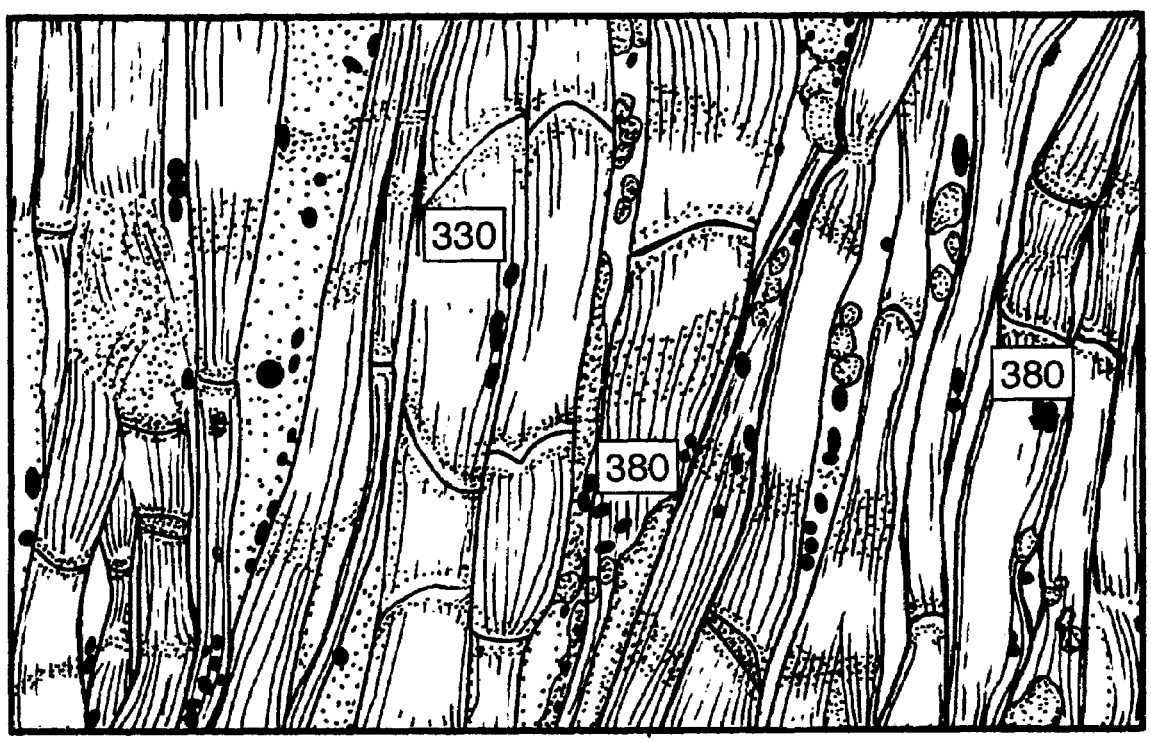
FIG. 3E illustrates an example of myocardium of an early myocardial infarction whereby a myocardium demonstrates increasing loss of cross striations.
Figure 3F:
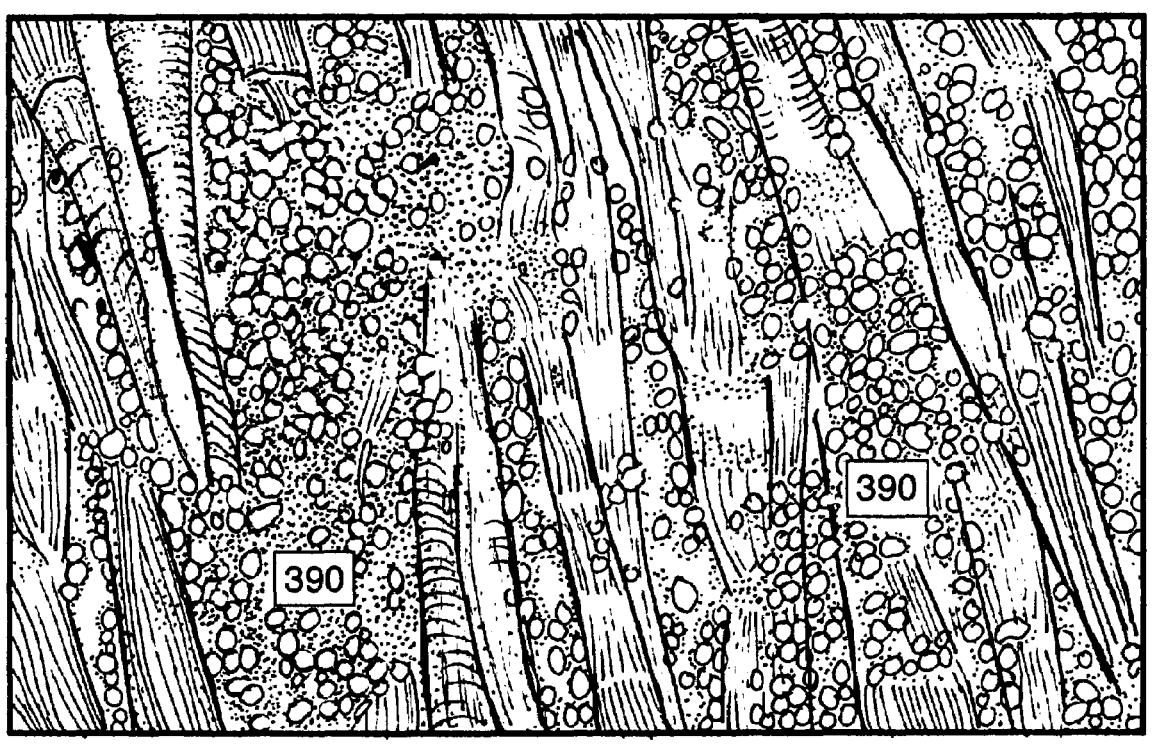
FIG. 3F illustrates an example of myocardium of an acute myocardial infarction and the loss of striations and the nuclei.
Figure 3G:
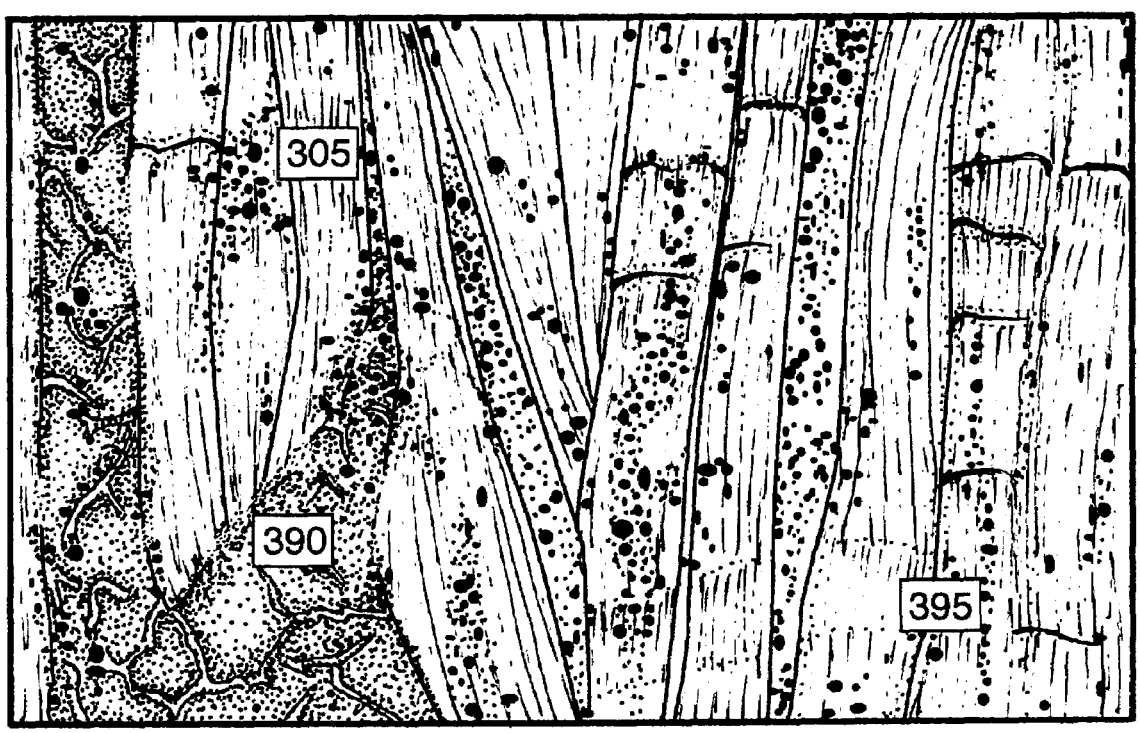
FIG. 3G illustrates an example of myocardium of an acute myocardial infarction resulting in neutrophilic infiltration and necrosis.
Figure 3H:
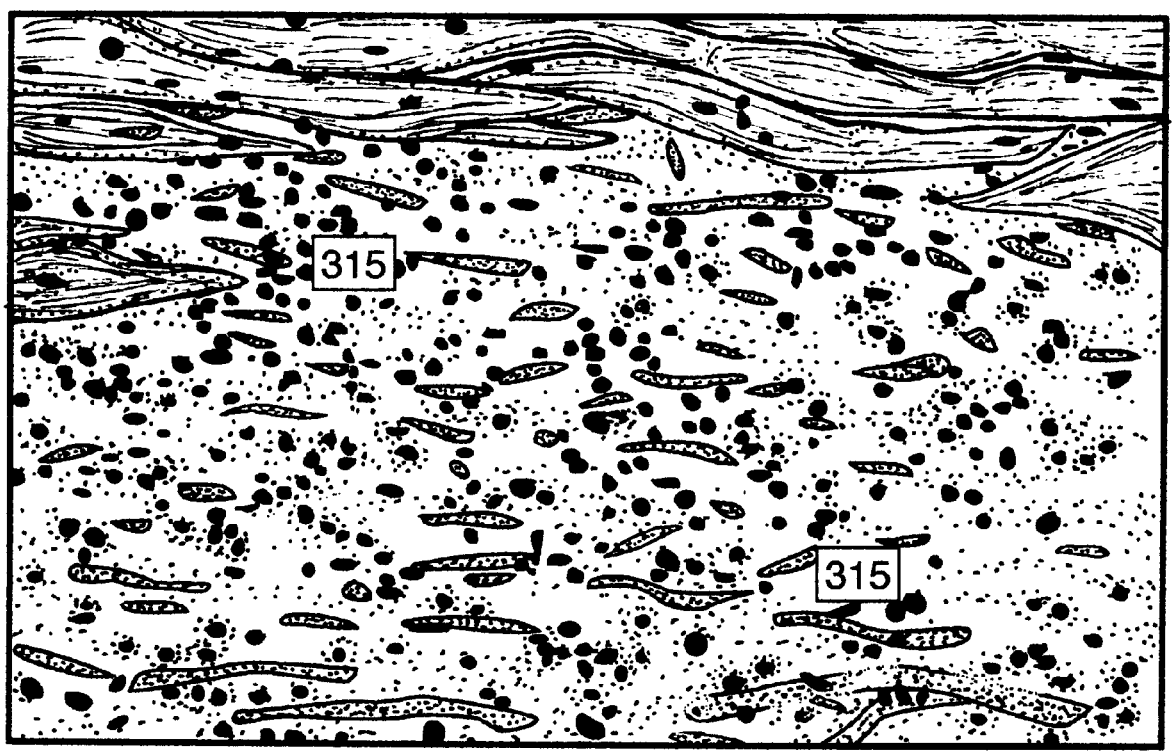
FIG. 3H illustrates an example of the myocardium of an acute myocardial infarction approximately one week after a myocardial infarction occurred. The capillaries, fibroblasts and macrophages fill with hemosidem.
Figure 31:
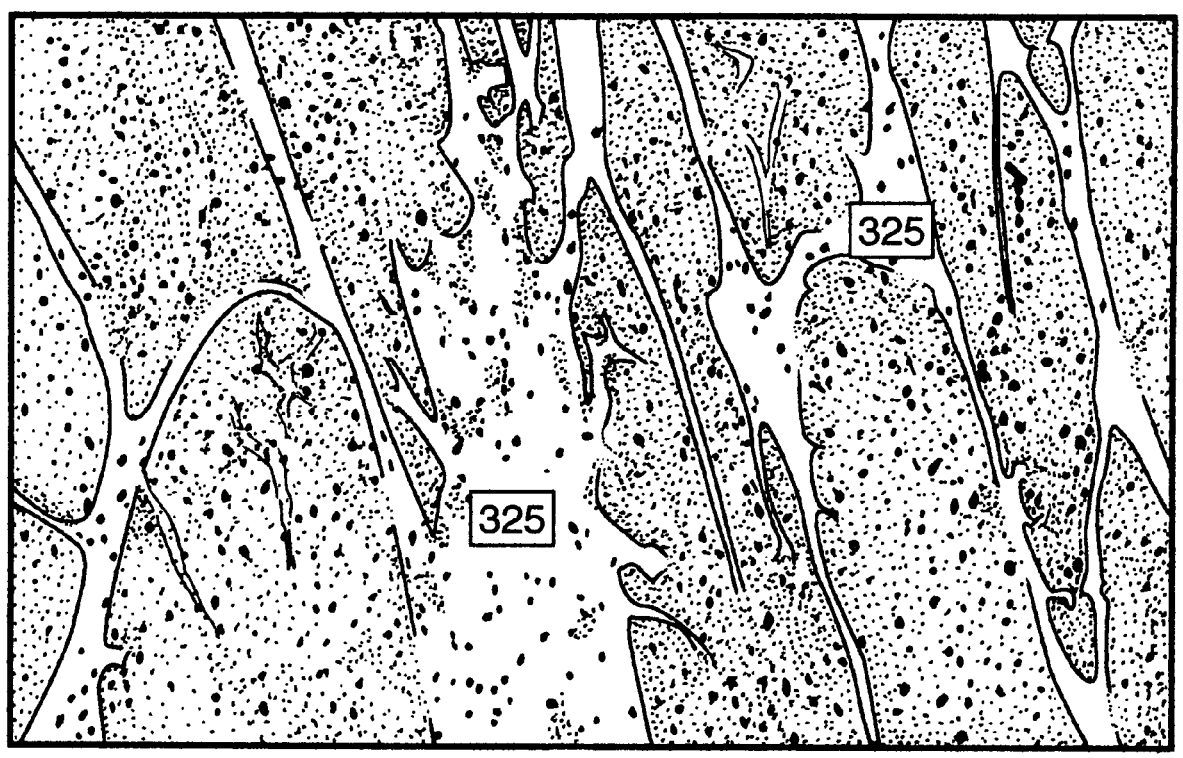
Figure 3J:
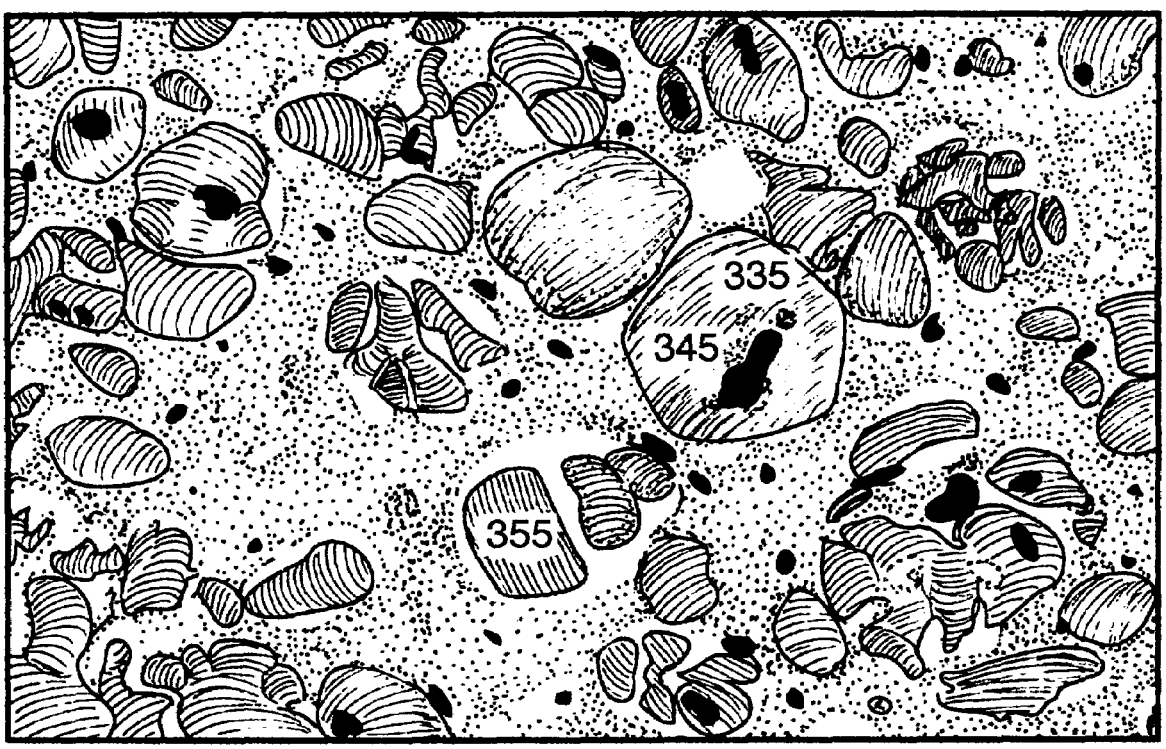
FIG. 3J illustrates myocardium several weeks after a myocardial infarction. Many surviving myocytes appear hypertrophic and their nuclei are dark in color. Interstitial fibrosis is also observed.
Figure 4:
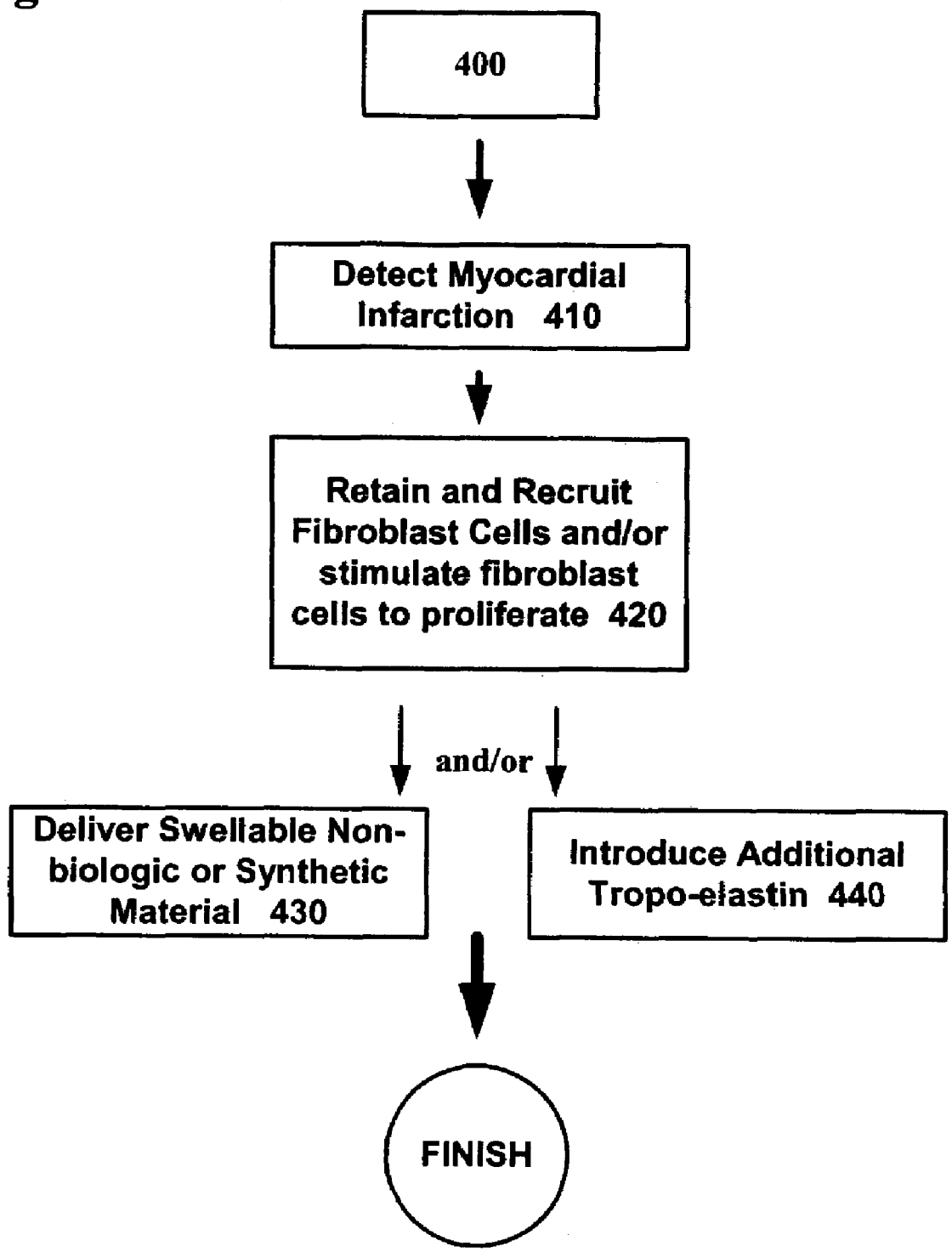
FIG. 4 illustrates various ways to restructure remodeling of the infarct region via retention and recruitment of fibroblasts and delivering a swellable reinforcing material and/or introduce additional tropoelastin to the infarct region.

FIG. 4 describes one embodiment of a method to treat an infarct region of a left ventricle. This is an illustrative diagram only and any of the treatments may be used in parallel (eg. at the same time) or sequentially or in any treatment combination. According to the method illustrated in FIG. 4, a myocardial infarction may be detected by an imaging process for example magnetic resonance imaging, optical imaging or ultrasonic imaging for example Echo ECG, spect, MRI, angiogram 410. Next, the area of the left ventricle is reinforced 410 by retention or recruitment of surrounding fibroblasts cells 420. In FIG. 4 one option to encourage the fibroblast occupancy of the infarct zone includes the use of swellable material 430 delivered to the infarct zone. Another method, summarized in FIG. 4 440 to encourage the occupancy of fibroblasts to the infarct zone includes the delivery of tropo-elastin to the site. It has been demonstrated that injections of fibroblasts into a scar region may improve the structural integrity of a terminally injured heart in a rabbit model see (Hutcheson et al "Comparison of benefits on myocardial performance of cellular cardiomyoplasty with skeletal myoblasts and fibroblasts" Cell Transplant 2000 9(3) 359-68). Since the fibroblasts naturally infiltrate the scar during the healing process, it would be beneficial to attract these cells in larger numbers, or to induce their proliferation in the infarct region such that fibroblasts are encouraged to remain in the region for a prolonged period or permanently remain in the region. In addition, a further benefit of retaining fibroblasts in an infarct region may be to convert the fibroblast phenotype such as influencing the conversion from non-contractile cell to a muscular cell. The conversion is promoted in the presence of growth factors for example TGF-β1 (transforming growth factor beta 1). Therefore, the infarct region may be treated with agents that encourage fibroblast retention and recruitment. Suitable treatment agents that may modify or recruit fibroblasts include but are not limited to, Angiotensin II, fibroblast growth factor (FGF basic and acidic), insulin growth factor (IGF), TGF-β in any of its isoforms, vascular endothelial growth factor (VEGF) in any of its isoforms, tumor necrosis factor-alpha (TGF-α), platelet-derived growth factor-BB (PDGF-BB), angiogenin, angiopoietin-1, Del-1, follistatin, granulocyte colony-stimulating factor (G-CSF), pleiotrophin (PTN), proliferin, transforming growth factor-alpha (TGF-α), vascular permeability factor (VPF), and LIH (leukemia inhibitory factor) genes that encode these proteins, transfected cells carrying the genes of these proteins, small molecules and pro-proteins that also contain these recruiting properties.

In one embodiment, basic fibroblast growth factor may be introduced to the infarct region by at least one of the methods described. In one embodiment, any of the described agents may be introduced in one or more doses in a volume of about 1 µl to 1 ml. In another embodiment, any of the described agents may be introduced in one or more doses in a volume of about 1 µl to 300 µl. In another embodiment, any of the described agents may be introduced in one or more doses in a volume of about 1 µl to 100 µl. In a preferred embodiment, the any of the described agents may be introduced in one or more doses in a volume of about 1 µl to 50 µl.

In alternate embodiments, the treatment volume may be larger (eg. intravenous pressure perfusion (IV) route). These volumes may range from about 2 mls to about 250 mls. Alternatively, these volumes may range from about 2 mls to about 100 mls. In other embodiments, these volumes may range from about 2 mls to about 30 mls.

2. Sequence of Treatment

Figure 5:
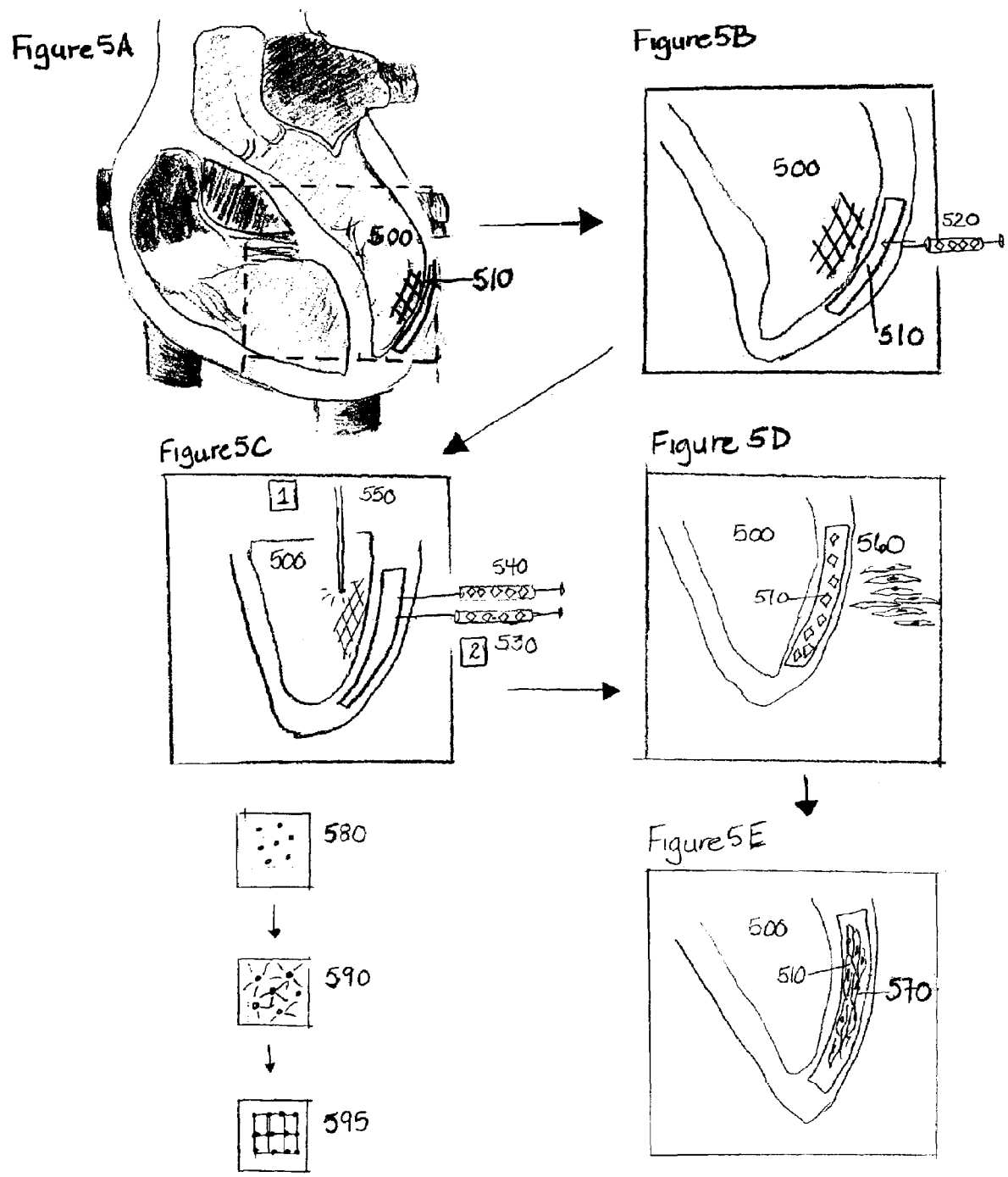
FIG. 5A-5E illustrates the introduction of a pro-fibroblastic agent to an infarct zone and the formation of structural scaffolding

FIG. 4 illustrates a flow chart of a process for treating MI by retaining and recruiting fibroblasts. FIG. 5A-5E illustrates the introduction and action of fibroblast retention and recruitment. Detection of acute myocardial necrosis may be performed using an ECG (electocardiogram) or by a more modem technology. For example, one technology such as [99m]Technetium-pyrophosphate or $^{111}$In-antimyosin antibody imaging has recently been approved by the Food and Drug Administration. With both these two tracers, results are obtained only 24-48 hours after acute infarction and therefore, the clinical utility of these techniques have been limited. There is another new agent called $^{99m}$Tc-glucurate that produces results within an hour after acute myocardial infarction (Iskandrian, A S, Verani M S, Nuclear Cardiac Imaging: Principles and Applications, Philadelphia, F. A. Davis 1996). Once the MI is detected the exact location of the infarct may be identified using a magnetic resonance imaging then the ventricle infarct region may be treated by reinforcement 501. An agent 520 (for example tropoelastin) is introduced to the infarct region 510. One way the agent may be introduced to the area is percutaneously, with the use of a catheter. A distal end of the catheter is advanced to the infarct zone 530, 540, or 550 and the agent 520 is released. Then the fibroblasts 560 are recruited to the site or retained 570. FIG. 5E illustrates the fibroblast reinforcement of the infarct area.

3. Description of Several Possible Treatment Agent(s) and Deliveries a. Tropoelastin. FIG. 5A-5E describes the combination of promoting fibroblast retention and migration into the infarct region with the addition of for example tropoelastin 520. Elastin is a highly pliable extracellular protein. In vivo, it is usually in a cross-linked insoluble state. A linear uncross-linked soluble precursor is available that is referred to as tropoelastin. Tropoelastin 520 can be made by recombinant methods and is commercially available. Tropoelastin is an approximately 70-kDa protein consisting of alternating hydrophobic regions, responsible for elasticity, and cross-linking domains. Additionally, it ends with a hydrophilic carboxy-terminal sequence containing its only two cysteine-residues. Tropoelastin is a protein that is prominent in the skin of an infant and as one matures less and less of this protein is made. Tropoelastin is sometimes used as an important marker of some heart conditions such as MI since it is released into the bloodstream following heart injury. The production of recombinant tropoelastin in bacterial systems has greatly simplified the availability of tropoelastin. In addition, it provides a valuable means for obtaining human tropoelastin. Purification from human aortas was greatly simplified compared with tissue extraction methods but relatively low yields were obtained. The purification from the aortas posed the potential for degradation of the polypeptide. Recently, human tropoelastin cDNA has also been expressed in bacteria as a fusion with influenza NS1 protein (Indik, Z., Abrams, W. R., Kucich, U., Gibson, C. W., Mecham, R. P. and Rosenbloom, J. (1990) Production of recombinant human tropoelastin: characterization and demonstration of immunologic and chemotactic activity *Arch. Biochem. Biophys*. 280, 80-86). This isoform of tropoelastin, containing exon 26A and the signal peptide, was the first form of human tropoelastin to be obtained for study. In view of tropoelastin's extreme amino acid usage, a synthetic human tropoelastin gene has been constructed containing codons designed to optimize expression in *E. coli* (Martin, S. L., Vrhovski, B. and Weiss, A. S. (1995) Total synthesis and expression in *Escherichia coli* of a gene encoding human tropoelastin *Gene* 154, 159-166). This synthetic gene is expressed at high levels in soluble form both as a fusion with glutathione S-transferase and directly, as the mature polypeptide. Alternatively, a simplified purification scheme using alcohol solubilization and eliminating the need for cyanogen bromide(CNBr) treatment resulted in significantly higher yields. Therefore, purified or genetically engineered tropoelastin is available. Recombinant forms of tropoelastin have proved to be viable alternatives to tissue-derived tropoelastin. Recombinant tropoelastin reacts with elastin antibodies, is a chemotactic agent, demonstrates coacervation ability and has the some similar characteristics to naturally occurring tropoelastin (i.e. circular dichroism).

In one embodiment, any of the described agents may be introduced in one or more doses in a volume of about 1 μl to 1 μl. In another embodiment, any of the described agents may be introduced in one or more doses in a volume of about 1 μl to 300 μl. In another embodiment, any of the described agents may be introduced in one or more doses in a volume of about 1 μl to 100 μl. In a preferred embodiment, any of the described agents may be introduced in one or more doses in a volume of about 1 μl to about 50 μl.

b. Microparticles and Growth Factors Delivery. One embodiment of a composition suitable for the described method includes the use of a bioerodiable microparticle harboring one or more of the aforementioned growth factors. The bioerodible microparticle may consist of a bioerodible polymer such as poly (lactide-co-glycolide). The composition of the bioerodible polymer is controlled to release the growth factor over a period of 1-2 weeks. It was previously demonstrated that biodegradable microparticles for example, poly (lactide-co-glycolide) were capable of controlled release of an oligonucleotide. These microparticles were prepared by the multiple emulsion-solvent evaporation technique. In order to increase the uptake of the oligonucleotide into the microparticles it was accompanied by polyethylenimine (PEI). The PEI also tended to make the microparticles more porous thus facilitating the delivery of the oligonucleotide out of the particles. See (De Rosa et al. Biodegradable microparticles for the controlled delivery of oligonucleotides," Int. J Pharm 2002 August 21;242 (1-2):225 In one preferred embodiment of a composition, the bioerodible microparticle may be a PLGA polymer 50:50 with carboxylic acid end groups. PLGA is a base polymer often used for controlled release of drugs and medical implant materials (i.e. anti-cancer drugs such as anti-prostate cancer agents). Two common delivery forms for controlled release include a microcapsule and a microparticle (e.g. a microsphere). The polymer and the agent are combined and usually heated to form the microparticle prior to delivery to the site of interest (Mitsui Chemicals, Inc). As the microparticles erode 560 a porous network of the microparticle composition is formed 570 in the infarct region resulting in a matrix with a controlled pore size 580. As the porous network is formed at least one angiogenic and/or pro-fibroblastic factor may be released encouraging the in-growth of new capillaries. One embodiment, the bioerodible polymer harbors the growth factor TGF-β1. In one embodiment, the PLGA polymer 50:50 with carboxylic acid end groups harbors TGF-β1 for slow release. It is preferred that each microparticle may release at least 20 percent of its contents and more preferably around 90 percent of its contents. In one embodiment, the microparticle harboring at least one angiogenic and/or pro-fibroblastic agent will degrade slowly over time releasing the factor or release the factor immediately upon contact with the infarct area in order to rapidly recruit fibroblasts to the site. In another embodiment, the microparticles may be a combination of controlled-release microparticles and immediate release microparticles. A preferred rate of deposition of the delivered factor will vary depending on the condition of the subject undergoing treatment.

Another embodiment of a composition suitable for the described method includes the use of non-bioerodible microparticles that may harbor one or more of the aforementioned growth factors. The growth factors may be released from the microparticle by controlled-release or rapid release. The microparticles may be placed directly in the infarct region. By directly placing the particles in the infarct they may also provide bulk for the region for reinforcement. The non-bioerodible microparticle may consist of a non- bioerodible polymer such as an acrylic based microsphere for example a tris acryl microsphere (provided by Biosphere Medical). In one embodiment, non-bioerodiable microparticles may be used alone or in combination with an agent to increase compliance of a ventricle. In another embodiment, non-bioerodiable microparticles may be used alone or in combination with an agent to recruit fibroblasts and/or stimulate fibroblast proliferation. In addition, non-bioerodiable microparticles may be used to increase compliance and recruit fibroblasts to an infarct region of a ventricle.

In one embodiment, the treatment agent compositions suitable for reinforcement of the infarct zone are rendered resistant to phagocytosis by inhibiting opsonin protein absorption to the composition of the particles. In this regard, treatment agent compositions including sustained release carriers include particles having an average diameter up to about 10 microns are considered. In other situations, the particle size may range from about 1 mm to about 200 mm. The larger size particles may be considered in certain cases to avoid macrophage frustration and to avoid chronic inflammation in the treatment site. When needed, the particle size of up to 200 mm may be considered and may be introduced via an intraventricular catheter or retrograde venous catheter for any of the embodiments herein to avoid chronic inflammation due to macrophage influx into the treatment site.

One method of inhibiting opsonization and subsequent rapid phagocytosis of treatment agents is to form a composition comprising a treatment agent disposed with a carrier for example a sustained release carrier and to coat the carrier with an opsonin inhibitor. One suitable opsonin-inhibitor includes polyethylene glycol (PEG) that creates a brush-like steric barrier to opsonization. PEG may alternatively be blended into the polymer constituting the carrier, or incorporated into the molecular architecture of the polymer constituting the carrier, as a copolymer, to render the carrier resistant to phagocytosis. Examples of preparing the opsonin-inhibited microparticles include the following.

For the encapsulation polymers, a blend of a polyalkylene glycol such as polyethylene glycol (PEG), polypropylene 1,2-glycol or polypropylene 1,3-glycol is co-dissolved with an encapsulating polymer in a common organic solvent during the carrier forming process. The percentage of PEG in the PEG/encapsulating polymer blend is between five percent and 60 percent by weight. Other hydrophilic polymers such as polyvinyl pyrolidone, polyvinyl alcohol, or polyoxyethylene-polyoxypropylene copolymers can be used in place of polyalkylene glycols, although polyalkylene glycols and more specifically, polyethylene glycol is generally preferred.

Alternatively, a diblock or triblock copolymer of an encapsulating polymer such as poly (L-lactide), poly (D,L-lactide), or poly (lactide-co-glycolide) with a polyalkylene glycol may be prepared. Diblocks can be prepared by: (i) reacting the encapsulating polymer with a monomethoxy polyakylene glycol such as PEG with one protected hydroxyl group and one group capable of reacting with the encapsulating polymer, (ii) by polymerizing the encapsulating polymer on to the monomethoxy polyalkylene glycol such as PEG with one protected group and one group capable of reacting with the encapsulating polymer; or (iii) by reacting the encapsulating polymer with a polyalkylene glycol such as PEG with amino functional termination. Triblocks can be prepared as described above using branched polyalkylene glycols with protection of groups that are not to react. Opsonization resistant carriers (microparticles/nanoparticles) can also be prepared-using the techniques described above to form sustained-release carriers (microparticles/nanoparticles) with these copolymers.

A second way to inhibit opsonization is the biomimetic approach. For example, the external region of cell membrane, known as the "glycocalyx", is dominated by glycoslylated molecules that prevent non-specific adhesion of other molecules and cells. Surfactant polymers consisting of a flexible poly (vinyl amine) backbone randomly-dextran and alkanoyl (hexanoyl or lauroyl) side chains which constrain the polymer backbone to lie parallel to the substrate. Hydrated dextran side chains protrude into the aqueous phase, creating a glycocalyx-like monolayer coating that suppresses plasma protein deposition on the foreign body surface. To mimic glycocalyx, glycocalyx-like molecules can be coated on the carriers (e.g., nanoparticles or microparticles) or blended into a polymer constituting the carrier to render the treatment agent resistant to phagocytosis. An alternate biomimetic approach is to coat the carrier with, or blend in phosphorylcholine, a synthetic mimetic of phosphatidylcholine, into the polymer constituting the carrier.

For catheter delivery, a carrier comprising a treatment agent (e.g., the composition in the form of a nanoparticle or microparticle) may be suspended in a fluid for delivery through the needle, at a concentration of about one percent to about 20 percent weight by volume. In one embodiment, the loading of the treatment agent in a carrier is about 0.5 percent to about 30 percent by weight of the composition. Co-encapsulated with protein or small molecule treatment agents could be stabilizers that prolong the biological half-life of the treatment agent in the carrier upon injection into tissue. Stabilizers may also be added to impart stability to the treatment agent during encapsulation. Hydrophilic polymers such as PEG or biomimetic brush-like dextran structures or phosphorylcholine are either coated on the surface or the carrier, grafted on the surface of the carrier, blended into the polymer constituting the carrier, or incorporated into the molecular architecture of the polymer constituting the carrier, so the carrier is resistant to phagocytosis upon injection into the target tissue location.

Any one or more catheters may be used to deliver the any one or multiple components of the embodiments to the infarct region area. Several catheters have been designed in order to precisely deliver agents to a damaged region within the heart for example an infarct region. Several of these catheters have been described (U.S. Pat. Nos. 6,309,370; 6,432,119; 6,485,481). The delivery device may include an apparatus for intracardiac drug administration, including a sensor for positioning within the heart, a delivery device to administer the desired agent and amount at the site of the position sensor.

Angiogenesis

After an MI the infarct tissue as well as the border zone and the remote zone begin to remodel. The scar tissue forms in the infarct region as the granulation is replaced with collagen, causing the scar to thin out and stretch. The perfusion in this region is typically 10% of the healthy zone, decreasing the number of active capillaries. Increasing the number of capillaries may lead to an increase in compliance of the ventricle due to filling up with blood. Other benefits of increasing blood flow to the infracted region is to provide a route for circulating stem cells to seed and proliferate in the infarct region. Angiogenesis may also lead to increased oxygenation for the surviving cellular islets within the infarct region, or to prime the infract region for subsequent cell transplantation for myocardial regeneration. In the border zone, surviving cells would also benefit from an increase in blood supply through an angiogenesis process. In the remote zone, where cardiac cells tend to hypertrophy and become surrounded with some interstitial fibrosis, the ability of cells to receive oxygen and therefore function to full capacity are also compromised; thus, angiogenesis would be beneficial in these regions as well. In one embodiment, angiogenesis will be stimulated in any region of the heart—infarct, border or remote is through delivery of angiogenesis-stimulating factors. Examples of these factors include but are not limited to isoforms of VEGF (eg VEGF121), FGF (eg b-FGF), Del 1, HIF 1-alpha (hypoxia inducing factor), PR39, MCP-1 (monocyte chemotractant protein), Nicotine, PDGF (platelet derived growth factor), IGF (Insulin Growth Factor), TGF alpha (Transforming Growth Factor), HGF (Hepatocyte growth factor), estrogens, Follistatin, Proliferin, Prostaglandin E1, E2, TNF-alpha (tumor necrosis factor), Il-8 (Interleukin 8), Hemotopoietic growth factors, erythropoietin, G-CSF (granulocyte colony-stimulating factors), PD-ECGF (platelet-derived endothelial growth factor), Angogenin. In other embodiments, these factors may be in provided in a sustained release formulation as independent factor or in combination with other factors or appropriate gene vectors with any of the gel or microparticle components described in this application.

c. Microparticles and Angiogenic and Pro-fibroblastic Agents. The microparticles may be prepared as microparticles harboring an angiogenic and/or pro-fibroblastic agent. On the other hand, the microparticles may be prepared and then the angiogenic and/or pro-fibroblastic agent introduced into the microparticle for example by diffusion prior to introduction to the infarct region. In the later example, the microparticles might also be coated with the factor and upon introduction to the infarct region the factor immediately recruits fibroblasts to the area. Additionally, the microparticle-factor composition might consist of any combination of the above-mentioned treatments. In other embodiments, it may be necessary to add at least one pharmaceutically acceptable inhibitor to the microparticles that prevents decomposition of the angiogenic or pro-fibroblastic agent.

d. Microparticle Components. FIG. 4 describes a method to structurally reinforce the infarct region. This method may be combined with any of the methods describing introducing angiogenic and/or fibroblast-recruiting agents, for example growth factors, to the infarct region to retain and/or promote fibroblast migration to this zone. Microparticles capable of taking up fluid will be introduced to the infarct region. Examples of these microparticles include swellable non-biological or a synthetic biological particles. The microparticles are introduced to the infarct zone and become trapped in the tissue. The microparticles tend to immediately start to swell. The swollen microparticles remain lodged in the tissue and provide reinforcement to the ventricular wall and add thickness to the thinning infarct region.

The dimensions of the infarct zone may determine the size range of the microparticles and the number of microparticles introduced to the infarct region. This will insure that the optimum post-hydrated microparticle mass is achieved. An embodiment relates to microparticles that are about 200 microns or less in diameter. In another embodiment the microparticles may be about 20 microns or less in diameter. In a preferred embodiment, the particle size may be about 5-10 microns in diameter. Particles of about 20 microns or less may also include an opsonization inhibitor (previously discussed). The swellable microparticles may be a range of sizes introduced to the infarct region. In one embodiment, the swellable non-biological material may be a hydrogel microsphere material. These microparticles are available commercially (A.P. Pharma or BioSphere Medical). These microparticles are resistant to non-specific absorption and are bio-stable.

In other embodiments, hydrogels may be used as a treatment for a myocardial infarction. Examples of hydrogel materials are high molecular weight polyacrylamide or high-molecular weight polyvinylpyrrolidone (PVP). Typically the monomer is supplied in these products containing di-functional monomers such as di-vinyl benzene, ethylene glycol dimethylacrylate or bis-acrylamide acetate resulting in the formation of a cross-linked network resistant to dissolution in an aqueous environment or to stimulate controlled magnitude angiogenic response. These components may e used to generate microspheres. Alternatively the di-functional polymers may be used to synthesize a hydrogel microsphere.

In one embodiment of the invention the first component of a biosynthetic polymeric gel may be (acrylamidomethyl) cellulose acetate propionate and the second component may be a dithiol functional polyethylene glycol polymer (such as sold by Shearwater Polymers). In another embodiment, the first component of a biosynthetic polymeric gel may be (acrylamidomethyl) cellulose acetate proprionate and the second component may be a reduced peptide sequence. In a further embodiment, the reduced peptide sequence could be biologically derived such as the amino acid sequence, glycine-cysteine-tyrosine-lysine-asparagine-arginine-aspartic acid-cysteine-glycine. A dual bore needle system may deliver both components separately one at a time or simultaneously to an infarct zone. The thiol-group(s) of the thiol-containing component may undergo nucleophillic addition to the acrylamide functional group of the first component. This forms the elastomeric structurally reinforcing gel.

In other embodiments, the delivery of a nonbiologic or synthetic gel may be combined with angiogenic and/ or fibroblast recruiting agents utilizing microparticles capable of releasing the agents at a rate optimal for fibroblast retention and migration in the infarct region.

In one embodiment, tropoelastin suspended in a solution, such as saline, is introduced to the infarct region for structural reinforcement of the ventricular wall. Another embodiment includes the introduction of tropoelastin suspended in saline in the presence of copper ions. Another embodiment includes the introduction of tropoelastin in the presence of a converting enzyme. Another embodiment includes the introduction of tropoelastin in the presence of lysyl oxidase. Once introduced to the infarct zone, the solution forms elastin by cross-linking via a lysine residue oxidation. The cross-linked elastin remains in the infarct region to fortify the tissue and enhance the modulus (wall strength/elongation=modulus) of elasticity.

4. Methods for Introduction and Action

FIG. 5A-5E illustrates the introduction and action of pro-fibroblastic agents to the infarct region to recruit fibroblast cell growth. The pro-fibroblastic agent may be introduced to the site 500 by a minimally invasive procedure 510. The solution may be injected in the infarct zone during an open chest procedure 520. The introduction of the pro-fibroblastic agent(s) includes one of the following procedures: sub-xiphoid and percutaneously 530. The mode of introduction of the pro-fibroblastic agent(s) by a percutaneous injection includes one of the following consisting of an intraventricular (coronary) catheter, a transvascular needle catheter, IC infusion and retrograde venous perfusion. One percutaneous route for a catheter is via a femoral artery traversing through and then across the aortic arch into the left ventricle. Imaging techniques can guide the catheter to the infarct region. The infarct region for example may be distinguished from healthy tissue using MRI techniques. A catheter having imported the MRI data may then be guided directly to the infarct region. Once the agent 540 is distributed through out the infarct region 510, the fibroblasts 560 may be attracted to the area by chemotactic responses. The fibroblast cells that infiltrate the area may proliferate in the area. Once the fibroblasts proliferate they form a reinforcing mass to the region and strengthen the damaged site 510. The fibroblast in this aspect of the present invention may act as a structurally reinforcing agent in the infarct zone 570. These cells add bulk to the area and replace the degraded myocytes that normally lead to a thinning of the infarct regional wall. In turn, the viable fibroblast cells release factors that may recruit other cells into the area for further reinforcement of the infarct zone.

In one embodiment, any of the described agents may be introduced in one or more doses in a volume of about 1 µl to 1 µl. In another embodiment, any of the described agents may be introduced in one or more doses in a volume of about 1 µl to 300 µl. In another embodiment, any of the described agents may be introduced in one or more doses in a volume of about 1 µl to about 100 µl. In a preferred embodiment, the any of the described agents may be introduced in one or more doses in a volume of about 1 µl to about 50 µl. If an agent is introduced via an IV or an IC route the volumes may range from about 1 ml to about 500 ml.

Any one or more catheters may be used to deliver the any one or multiple components of the embodiments to the infarct region area. Several catheters have been designed in order to precisely deliver agents to a damaged region within the heart for example an infarct region. Several of these catheters have been described (U.S. Pat. Nos. 6,309,370; 6,432,119; 6,485, 481). The delivery device may include an apparatus for intracardiac drug administration, including a sensor for positioning within the heart, a delivery device to administer the desired agent and amount at the site of the position sensor.

B. Multiple Component Systems for Infarct Reconstruction

Component One.

To prevent heart failure, it has been proposed that cardiomyocytes can be directly introduced into the infarct region to restore cardiac function cells of various origins, including embryonic and adult stem cells. The viability of tissue engineering for a myocardial infarct zone requires that oxygen and nutrient supplies are readily available, as well as a mode for removal of waste products from cell metabolism. The cells in these areas also need a supporting structure for adherence. The bioerodible gel with angiogenic and/or fibroblast recruiting agents previously discussed provides this later supporting structure. In the literature, it is known that the introduction of scaffolding with a bore size of less than 10 microns leads to a tightly fibrotic encapsulated scaffold with poor capillary ingrowth. On the other hand as demonstrated in FIGS. 6 and 9, if the scaffolding pore diameter is around 20 microns, cellular encapsulation of the scaffold system is well perfused with capillary in-growth leading to fibrotic poor cellular rich region. One embodiment includes scaffolding that is introduced to the infarct zone 610, 910 and acts as a mechanical reinforcement. The force is distributed more evenly 990 at the infarct region and ventricular remodeling is prevented.

In one embodiment, separate components are included to provide a network such as described above. One example is described in FIG. 6. A multi-component composition includes the first component including the previously illustrated bioerodible matrix or scaffolding 630, 990. In this particular composition, the matrix (first component) provides a porous scaffolding to enhance capillary in-growth. The microparticles of the first component may be approximately 20 microns. In another embodiment, the first component of the composition may be introduced in a minimally invasive procedure 960 such as percutaneously. A distal end of the catheter is advanced to the infarct zone 910 and the bioerodible microparticles 920 are released. In a further embodiment, the first component of the composition may be introduced via an intra-ventricular needle device 930 to the infarct region. In a further embodiment, an intra-ventricular needle device including introducing multiple injections to the infarct region may introduce the first component of the composition. The first component may serve in one aspect as a domain to promote cell growth. In addition, porosity may be controlled that leads to capillary in-growth. The first component 920 may be a bioerodible microparticle with growth factor and angiogenic potential. The factor or other agent may release over a 1-2 week period. One embodiment may be that the first component includes PLGA 50:50 (previously described) with carboxylic acid end groups. An example of capillary in-growth to the domain provided by the first component may be facilitated by the release of angiogenic factors 980. One embodiment includes microparticles containing angiogenic factors 980 that release rapidly after introduction to the infarct region. This tends to result in a rapid angiogenic response.

Biomaterials have been employed to conduct and accelerate otherwise naturally occurring phenomena, such as tissue regeneration in wound healing in an otherwise healthy subject; to induce cellular responses that might not normally be present, such as healing in a diseased subject or the generation of a new vascular bed to receive a subsequent cell transplant; and to block natural phenomena, such as the immune rejection of cell transplants from other species or the transmission of growth factor signals that stimulate scar formation in certain situations.

Figure 9A:
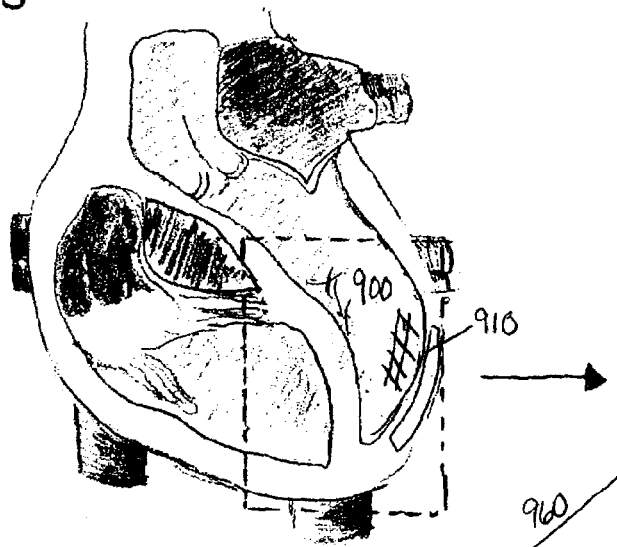
Figure 9B:
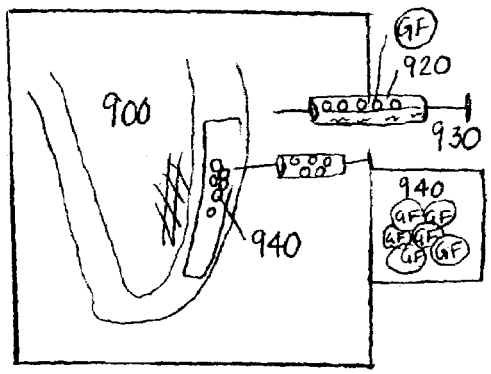
Figure 9C:
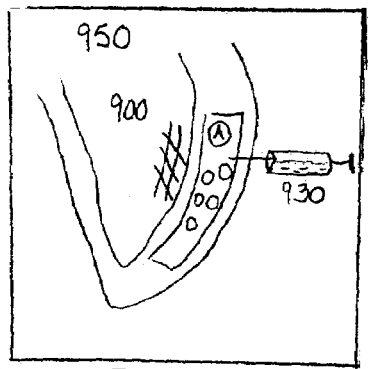
Figure 9D:
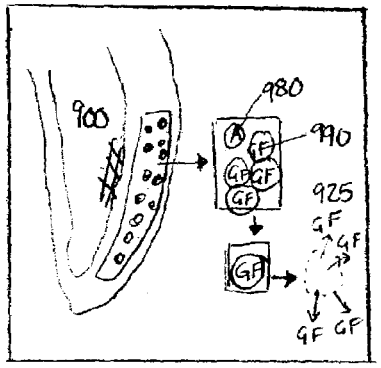
Figure 9E:
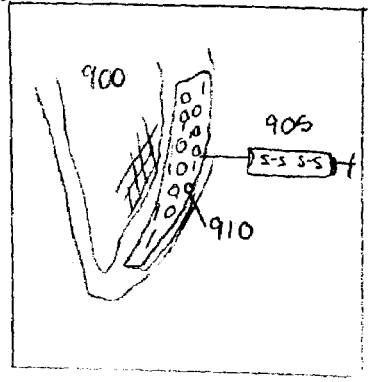
Figure 9F:
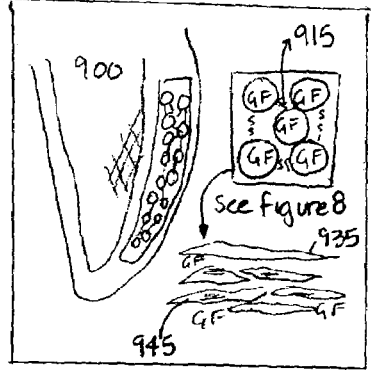

2. Component 2. A second component 640 of the multi component composition according to the method may be an acrylate agent that is biocompatible. A second component serves in one aspect to disperse the first component in order to form a more uniform scaffold over the entire infarct zone and may include border zone as well. It may be an oligomeric di- (or multi-) functional acrylate agent 930 based on a component that is biocompatible. An embodiment of the two-component composition may include a second component 930 comprising the following group di-acryloyl polyethylene glycol, tetra-acryloyl polyethylene glycol (PEG) or (acrylamidomethyl) cellulose acetate proprionate. In order to dissolve the acrylamide functional cellulose component ethanol or a biocompatible is required. The second component 930 disperses the microparticles. 970/990 acting as a suspending media. It is known that PEG-coated microparticles 990 are less inflammatory and are seen not to elicit a fibrotic response. Thus, it in one aspect may serve as an anti-opsonization agent. Thus, they serve as a camouflage from the immune system for introduction of the microparticles to the infarct region. One embodiment includes the injection of both the growth factor containing microparticles and the scaffold-forming matrix (acryloyl functional macromer) using a dual bore needle. FIG. 9D illustrates the final formation of the scaffold gel 915. The introduction of the two solutions simultaneously creates the near instantaneous (around 10 seconds) formation of the gel with a microparticle network imbedded within the scaffolding gel 915. As the microparticles 925 decompose, growth factors are released promoting the capillary formation within the matrix. In addition, cells begin to grow in the infarct area 935. These cells release proteases that may result in the decomposition of the scaffolding ultimately creating additional area for cellular in-growth. In addition, the cells secrete their own extracellular matrix, the polymer degrades and the resulting tissue may eventually become a completely natural environment. The decomposition products may be cleared from the area by the renal system since capillary re-growth may occur.

3. Component 3. Another component of a multi component composition and method is illustrated in 650 and 905. A third component includes one of the following: thiol-containing peptide or a di- or multi-functional biocompatible such as dithio-PEG. An example of a thiol-containing peptide 905 may be polycysteine oligomers. An example of this is a protected form of a polycysteine oligomer, Poly-S-CBZ-L-cysteine or Poly-S-benzyl-L-cysteine (Sigma Chemical P0263 and P7639 respectively). These agents can be de-protected using standard organic chemistry protocols (Berger et. al. "Poly-L-cysteine" J. Am. Chem. Soc 78, 4483 (1956). The preparation of these thiol-containing agents is well known (Zervas, L. et.al. "On Cysteine and Cystine Peptides" J. Am. Chem. Soc. 85:9 1337-1341, (1963)). Additional agents that may function as the third component of a multi-component composition may be a naturally occurring peptides. In one embodiment, the third component of the multi-component scaffolding may be one of the following consisting of Poly-S-CBZ-L-cysteine and Poly-S-benzyl-L-cysteine. In another embodiment of a multi-component composition, the third component of the multi-component scaffolding may be a naturally occurring peptide. In a further embodiment of a multi-component composition the third component of a multi-component scaffolding may be the naturally occurring peptide glycine-cysteine-tyrosine-lysine-asparagine-arginine-aspartic acid-cysteine-glycine peptide sequence. The third component preferably contains at least two thiol groups. FIG. 9A-9F illustrates the introduction of the three components to the infarct region to treat an MI. One embodiment may be the introduction of the first component and the second component 920/930 through a dual bore needle and then the introduction of a thiol-containing third component 905 through a second needle. FIG.9D illustrates a schematic of the final structure 915 that subsequently recruits fibroblast growth 935 and capillary 945 in-growth into the infarct region. The thiol-containing component 905 may be used to decrease the rate of decomposition of the scaffold and control release of the fibroblast recruiting components of the microparticles.

Any one or more catheters may be used to deliver the any one or multiple components of the embodiments to the infarct region area. Several catheters have been designed in order to precisely deliver agents to a damaged region within the heart for example an infarct region. Several of these catheters have been described (U.S. Pat. Nos. 6,309,370; 6,432,119; 6,485, 481). The delivery device may include an apparatus for intracardiac drug administration, including a sensor for positioning within the heart, a delivery device to administer the desired agent and amount at the site of the position sensor.

Multi Component System for Infarct Reconstruction and Infarct Reoxygenation

The progression of heart failure after an MI is a result of the remodeling of the heart after infarct. In the remodeling processes the heart becomes thinner and the diameter increases in response to a decrease in heart output, in an effort to maintain a continual cardiac output. This process of thinning results in an increase in the radius of the heart and the stresses on the heart increase.

It has been shown that perfluorocarbon compounds have a high affinity for gases, for example carbon dioxide and oxygen. The ability of perfluorocarbons to transport oxygen is approximately eighteen times greater than blood plasma in a comparable volume of each component. In addition, it was shown that the half-life for oxygenation/deoxygenation is approximately three and one half times faster for many perfluorated compounds as compared to hemoglobin. Thus, perfluoro compounds may be used in tissues to aid in the reoxygenation of an affected region such as an infarct region. A few examples that demonstrate biocompatibility in a subject are identified in Table 1.

FIG. 7 illustrates the multi-component system in a flowchart. The myocardial infarction is located 720. Then, the components are delivered to the region via a minimally invasive procedure by methods previously described and/or by catheter delivery. It was previously disclosed that the addition of a thiol functionality FIG. 6 component 3 in the presence of an electron deficient double bond, such as an acryloyl functionality FIG. 6 component 2, can undergo a Michael addition. Under basic conditions the thiol functionality becomes hypernucleophillic and rapidly (<<10 seconds) forms a bond with the acryloyl functionality (see FIG. 10). As illustrated in FIG. 6, a gel may be formed to prevent infarct expansion and/or bulking thus preventing a remodeling of the heart that may lead to heart failure. FIG. 7 730 illustrates the first component that includes a bioerodiable gel and 740 illustrates the gel accompanied by a perfluorinated compound as the second component to enhance oxygenation of the tissue. The gel is formed by a three-component system. The first component includes a biocompatible polymer as previously described with a multifunctional spacer group 730. The second component 840 includes a difunctional or multifunctional perfluorinated molecule 810. The third component 750 includes a hetero-functional molecule with a reactive functionality on one side of the spacer group, and a cell binding peptide sequence, such as the peptide sequences previously described, on the terminal end. One example of a peptide sequence includes the RGD sequence. FIG. 8 illustrates in schematic form the reaction of the thiol component 800 and the acryloyl functional group 820 to form one compound 830 of the three-component system of FIG. 7. This three-component system may be introduced to the infarct region by similar minimally invasive methods as described for the methods of FIG. 6 that may be guided by mapping the heart prior to administration of an agent. Examples of this three-component system are discussed in the example section.

In one embodiment, any of the described agents may be introduced in one or more doses in a volume of about 1 µl to 1 ml. In another embodiment, any of the described agents may be introduced in one or more doses in a volume of about 1 µl to 300 µl. In another embodiment, any of the described agents may be introduced in one or more doses in a volume of about 1 µl to 100 µl. In a preferred embodiment, the any of the described agents may be introduced in one or more doses in a volume of about 1 µl to 50 µl. IV, and IC routes may be required which would involve larger treatment volumes (for example about 2 mls to about 250 mls).

FIG. 10 illustrates the ester bond formed between the second component (1000) and the third component (1010) of a multi-component composition of FIG. 6. This bond (1020) is necessary for delaying the degradation of the scaffolding and release of the active agents within the microparticles. This bond tends to resist degradation for approximately 2 months.

Swellable Agent Systems for Reinforcement

Figure 11A:
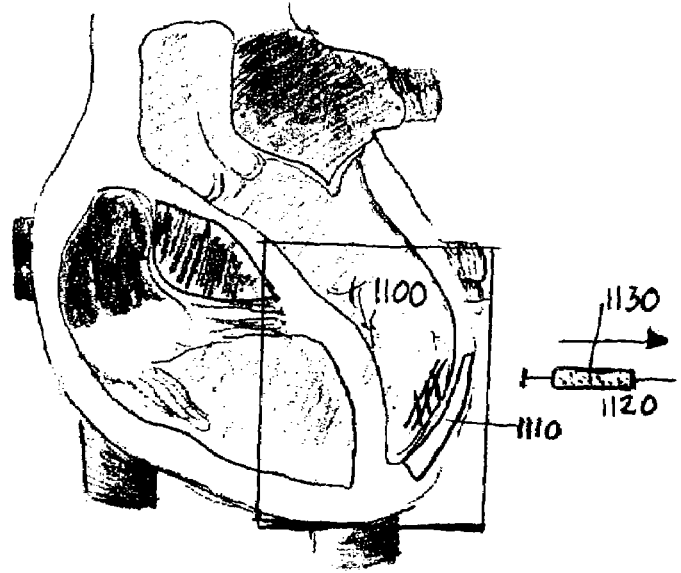
Figure 11B:
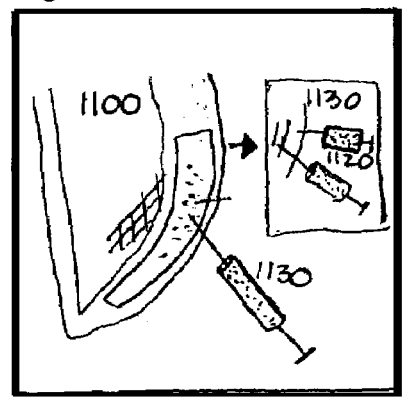
Figure 11C:
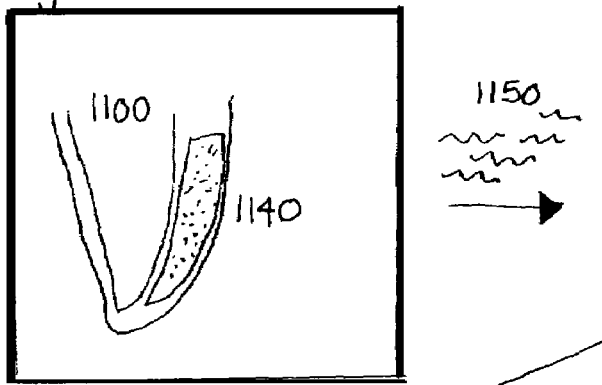
Figure 11D:
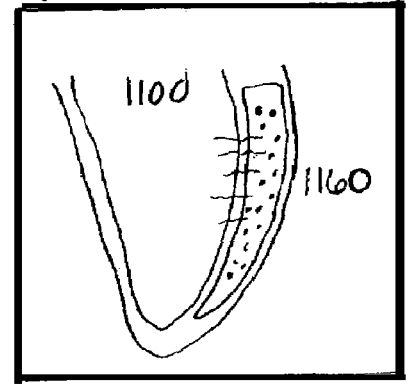

FIG. 11A-11F illustrates the introduction of a swellable non-biologic material to structurally reinforce and/or bulk the infarct region. FIG. 11A illustrates the introduction of microparticles 1130 to an infarct region 1110. Microparticles 1130 are shown accumulated in a mass at the site of the left ventricle 1100 within the infarct zone. One method for introduction of the microparticles 1120 is percutaneously with the use of a catheter 1130. A distal end of the catheter is advanced to the infarct region 1110 and the microparticles 1130 are released. The microparticles become lodged in the infarct tissue 1140. FIG. 11B illustrates microparticles 1130 acquiring the necessary surrounding fluid 1150 to swell 1160/1170. One embodiment includes the use of microparticle beads capable of fluid uptake in the infarct region to structurally reinforce the region. The particles will range in size from approximately 5 to approximately 10 microns. The microparticles will be less than 10 microns so that the completely swollen particle becomes lodged in the site (1180) but is not too large to become an obstruction in the area. In addition, the swollen microparticles provide mechanical strength and thickness to the damaged area by replacing the dead and degraded myocardial cells.

Figure 11E:
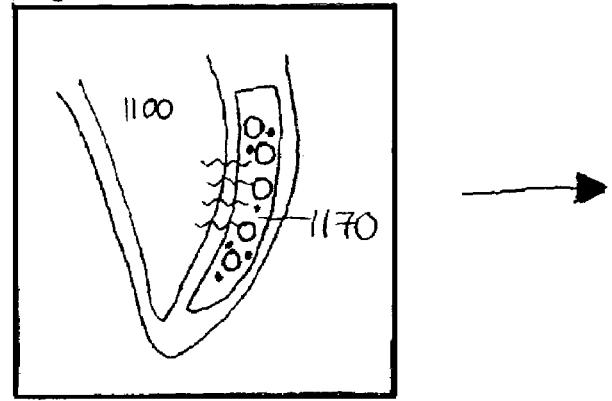
Figure 11F:
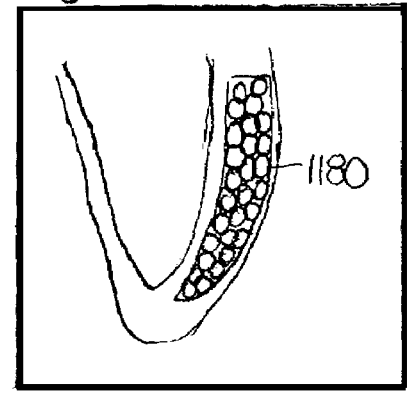

1. Agents. a. Hydrogels spheres. Examples include hydrogel spheres composed of cross-linked polyacrylamide or cross-linked PVP. The monomeric form of these products will contain di-functional monomers such as di-vinyl benzene, ethylene glycol dimethylacrylate or bis acrylamido acetic acid. These agents form a cross-linked network that is resistant to dissolution in aqueous systems.

b. Commercial Products. Several commercial products are available that may be used such as microparticles obtained from A.P. Pharma or Biosphere Medical. These microparticles resist non-specific protein absorption and have biostable backbone linkages. These microparticles are not bioerodable or bioabsorbable. FIG. 11E illustrates the microparticles dispersed in the infarct region taking up the surrounding fluid and swelling until they become lodged in the region (FIG. 11F).

Structural Reinforcement Compositions and Materials

FIG. 12 illustrates several possible methods to reinforce the ventricular wall of the infarct region of an MI subject. Restraining the infarct zone by suturing an epicardial polymer mesh was previously demonstrated (Kelley et al., Circ., 1999; 135-142). Due to the nature of this technique suturing the mesh directly into the tissue was necessary. This may cause further damage. This procedure requires invasive surgery. In addition, the polymer mesh does not degrade over time and this may also be a problem. By injecting a reinforcing agent directly into the affected area by minimally invasive procedures, this avoids the intrusive suturing protocol. The solution may be injected in the infarct zone during an open chest procedure. In one embodiment, the introduction of the reinforcing solution comprises the following procedures consisting of sub-xiphoid and percutaneously. In another embodiment, the mode of introduction of the reinforcing solution by a percutaneous injection comprises one of the following consisting of an intraventricular catheter, a transvascular needle catheter and retrograde venous perfusion.

1. Single Component Systems. FIG. 12 1210/1220/1230 illustrate the identification and reinforcement of the MI region prior to intervention by a reinforcing agent. FIG. 12 1210 describes the use of a single component injected into the infarct region. This example constitutes a single pseudoplastic or thixotropic material capable of forming a gel-like reinforcement to the infarct region wall. Several examples of these materials exist. In one embodiment, the structural reinforcing agent includes one of the following consisting of hyaluronic acid, bovine collagen, high-molecular weight ultra-pure polyacrylamide and polyvinyl pyrrolidone.

In one specific embodiment of the present invention, the single component for structural reinforcement comprises bovine collagen dispersed with PMMA (polymethyl methylacrylate) beads. These beads may be manufactured under the trade name of ARTECOLL (Rofil Medical International, Breda, The Netherlands). PMMA is one of several cross-linked or highly insoluble microparticles. PMMA was discovered in the early 1900's and was used initially in dental prosthesis. Recently, it has been used in bone replacement of the jaw and hip. In addition, it has been used for artificial eye lenses, pacemakers and dentures. ARTECOLL™ has principally been used in filling folds and wrinkles of the face, augmenting lips, adjusting an irregular nose.

Possibly one of the most important features of the insoluble microparticles is the surface of the microparticles must be smooth to induce collagen deposition. A rough surface promotes macrophage activity while discouraging collagen deposition. The methods incorporate the use of smooth surface particles. The components may act as a substrate for endogenous collagen deposition. As the reinforcing gel degrades, the highly stable and smooth microparticles may be exposed to the fibroblast cell population occupying the site. This triggers the production of collagen to replace the decomposing gel. Therefore, the infarct zone may be reinforced by the collagen replacement of the temporary gel. In one embodiment, the dispersing material includes one of the following group of microparticle materials consisting of PMMA (polymethyl methylacrylate), P(MMA-co BMA) (polymethyl methylacrylate-co butyl methylacrylate), carbon microparticles (Durasphere), polystyrene, cross-linked acrylic hydrogels and PLGA. In another embodiment, the cross-linked acrylic hydrogel may include the following HEMA (2-hydroxyethyl methacrylate), AA (acrylic acid), AMPS (acrylamido-methyl-propane sulfonate), acrylamide, N, N, di-methyl acrylamide, diacetone acrylamide, styrene sulfonate, and di- or tri-functional monomers. The di or tri-functional monomers may be EGDMA (ethylene glycol dimethacrylate) and DVB (di-vinyl benzene). In addition, the use of highly crystalline (and hydrolysis resistant) PLGA microparticles may outlast the carrier gel and also provide a useful substrate for collagen deposition.

Another single solution introduced to the infarct zone may be hyaluronic acid dissolved in sodium salt in water. This is a manufactured gel sold as a dermal augmentation gel (RESTYLANE™). Hyaluronic acid hydrogel has also been used in the past for control of delivery of therapeutic agents in wound sites (Luo, Y. et al. Cross-linked hyaluronic acid hydrogel films: new biomaterials for drug delivery" Journal of Controlled Release (2000) 69:169-184). Other possible single introduced components include bovine collagen (ZYDERM™ or ZYPLAST™), another dermal augmentation gel developed by Collagen Corp. The high molecular weight, ultrapure polyacrylamide in water may be FORMACRYL™ or BIOFORM™ other dermal augmentation gels. The bovine collagen may be dispersed by the PMMA product ARTECOLL™. ARTECOLL™ is best known for its success as a biocompatible dermal augmentation gel for reconstruction. RESOPLAST™ (Rofil Medical International, Breda, The Netherlands) may also be used as a single component gel.

FIG. 12 1220 illustrates another method to reinforce the infarct zone of the ventricle using a single component system. This example utilizes the introduction of a single component that forms a gel after reacting with an endogenous component. One such component may be tropoelastin (detailed previously). Elastin is the insoluble, elastic protein of high tensile strength found in connective tissue of the large arteries, trachea, bronchi and ligaments. Rarely seen endogenously as tropoelastin (the uncross-linked form), it rapidly cross-links to lysine residues in a process of oxidative deamination by the enzyme lysyl oxidase when introduced in vivo. As stated previously, tropoelastin is available commercially as a recombinant bacterial product. When heated in water tropoelastin forms a coacervate and this may be injected into the infarct region where lysyl oxidase induces lysine cross-linking by the oxidative deamination process. In one embodiment, tropoelastin may be introduced to the infarct region. In another embodiment, tropoelastin may be introduced to the infarct region after the introduction of the highly insoluble microparticles described above. Another reactive single-component may be cyanoacrylate adhesive. This is a widely used plastics binding agent. In one embodiment the cyanoacrylate may be octyl cyanoacrylate. The octyl cyanoacrylate may be the manufactured product called Dermabond™ (Johnson and Johnson). This product was recently approved for use as a tissue adhesive for wound closure. Octyl cyanoacrylate may be introduced to the infarct region as a liquid. Once it contacts the infarct region, it solidifies due to its exposure to moisture. In another embodiment, the octyl cyanoacrylate may be introduced to the infarct region after the introduction of the highly insoluble, stable microparticles described above.

In another embodiment, a reactive single component includes a component that is temperature sensitive. This is illustrated in FIG. 12 1230. One example of this type of component is a component that may be a liquid at room temperature and once exposed to a temperature approximately equal to body temperature the component gels. A more specific component includes introducing block co-polymers of silk protein-like sub units and elastin-like sub units. An example of the block co-polymer synthetic protein may be ProLastin (PPTI, Protein Polymer Technologies). These components gel due to non-covalent interactions (hydrogen bonding and crystallization of silk-like subunits) at elevated temperatures for example approximately equal to body temperature. With these components, no lysine residues are present, so cross-linking due to endogenous lysyl oxidase does not occur. The formation of the gel via a change in temperature may be adjusted using additives. These additives include but are not limited to sodium chloride, Diglyme (Diethylene Glycol Dimethyl Ether; 2-Methoxyethyl Ether; Bis (2-Methoxy Ethyl Ether), and ethanol.

Many thermal reversible materials may be used for reinforcement of the myocardial tissue. Generally, thermal reversible components at temperatures of approximately 37 degrees Celsius and below are liquid or soft gel. When the temperature shifts to 37 degrees Celcius or above, the thermal reversible components tend to harden. In one embodiment, the temperature sensitive structurally reinforcing component may be Triblock poly (lactide-co-glycolide)-polyethylene glycol copolymer. This is commercially available (REGEL™ Macromed, Utah). In another embodiment, the temperature sensitive structurally reinforcing component may include the following consisting of poly (N-isopropylacrylamide) and copolymers of polyacrylic acid and poly (N-isopropylacrylamide). Another temperature sensitive structurally reinforcing component commercially available is PLURONICS™ (aqueous solutions of PEO-PPO-PEO (poly(ethylene oxide)-poly (propylene oxide)-poly(ethylene oxide) tri-block copolymers BASF, N.J.) (Huang, K. et al. "Synthesis and Characterization of Self-Assembling Block copolymers Containing Bioadhesive End Groups" Biomacromolecules 2002,3, 397-406). Another embodiment includes combining two or more of the single components in order to structurally reinforce the infarct region. For example, silk-elastin, collagen and Laminin may be used as a one-part system. The silk-elastin would likely form in situ cross-links due to the silk blocks.

In another embodiment, a reactive single component includes a component that is pH sensitive. The component remains in a liquid state if it is sufficiently protonated preventing gelation. In another embodiment, the component is initially maintained at a low pH for example pH 3.0 and later introduced to the treatment area that results in gelation of the component due to the physiological pH of the environment. One example of this is discussed in Example 3. Several possible cationic agents may be but are not limited to one of the following cationic agents that remain protonated at low pH, poly (allyl amine), DEAE-Dextran, ethoxylated Poly(ethylenimine), and Poly(lysine). Other examples may one of but are not limited to the following anionic agents for example, dextran sulfate, carboxymethyl dextran, carboxymethylcellulose, polystyrene sulfanate and chrondroitin sulfate.

Additionally, any of these microparticle components may be accompanied by one or more contrast agent and/or suitable agent(s) for treatment of the region. The contrast agent or treatment agent may be conjugated to or dissolved into the structural component prior to introduction to the infarct area. The agents that may accompany the reinforcing component(s) may include but are not limited to angiogenic agents, ACE inhibitors, angiotensin receptor blockers, SRCA (sercoplasmic reticulum calcium pump) pump increasing agents, phospholamban inhibitors and anti-apoptotic drugs. These agents may be in the form of small molecules, peptides, proteins or gene products. The small molecules may be optionally conjugated to a component of the solution, dispersed in solution, or dissolved in solution to improve the adhesion of the reinforcing components to the tissue. One embodiment is to conjugate a peptide with a conserved region that mediates adhesion processes. A conserved region of a peptide may be a sequence of amino acids having a special function of identification that has been conserved in a protein family over time. Another embodiment includes the use of a specific peptide conjugate with a conserved RGD (arginine (R)-glycine(G)-asparagine(D)) motif in the presence of the reinforcing component. In further embodiments, the RGD motif peptide may include the following such as von Willebrand factor, osteopontin, fibronectin, fibrinogen, vitronectin, laminin and collagen. One embodiment seeks to minimize thinning during remodeling of the infarct region. Thus, bulking and reinforcing the infarct region post-MI may preserve the geometry of the ventricle.

Any one or more catheters may be used to deliver the any one or multiple components of the embodiments to the infarct region area. Several catheters have been designed in order to precisely deliver agents to a damaged region within the heart for example an infarct region. Several of these catheters have been described (U.S. Pat. Nos. 6,309,370; 6,432,119; 6,485, 481). The delivery device may include an apparatus for intracardiac drug administration, including a sensor for positioning within the heart, a delivery device to administer the desired agent and amount at the site of the position sensor.

2. Dual Component Systems. FIG. 12 1240 illustrates the use of dual component systems for the formation of structurally reinforcing gels for application to the infarct region. Initially, the infarct region is identified by imaging methods previously discussed 1300. FIG. 13 1330/1340/1350/1360/1370/1380/1390 illustrates a flowchart further describing dual component systems of FIG. 13 1360 to form a structurally reinforcing gel in the infarct region 1320. In one example 1330, two components are combined at the infarct zone at around physiological pH. Component one is a principally anionic solution and the second component is principally a cationic solution at approximately physiological pH. When the two components are mixed together at the infarct zone, a gel forms rapidly and irreversibly. In one embodiment, a dual component system may comprise poly (acrylic acid) as a first component and poly (allyl amine) as a second component as illustrated in FIG. 13 1330. In another embodiment, a dual component system may comprise poly (acrylic acid) as a first component and poly (allyl amine) as a second component that may be delivered by a catheter with dual injection lumens. Other dual component systems to form a structurally reinforcing gel in the infarct region may include elastin as a first component and lysyl oxidase as a second component 1340; sodium alginate as a first component and an aqueous solution of calcium chloride as a second component 1350, and tropoelastin and collagen as a first component and cross-linker lysyl dehydrogenase as a second component and laminin 1395 may be added to this combination later. The composition of each component will depend on the mechanical property of the final cross-linked system. Other substances that can replace the lysyl dehydrogenase or complement its cross-linking ability might be used such as glutaraldehyde, and/or photoactivatable crosslinkers for example blue dye used to cross-link. Additionally, these dual component systems may be combined with other individual system utilizing commercial products such as AVITENE™ Microfibrillar Collagen Hemostat), SUGICEL™, (absorbable haemostat, Johnson & Johnson), GELFOAM™, FLOSEAL™ (Baxter, matrix hemostatic sealant with a granular physical structure and thrombin), FOCAL SEAL™ (Focal, Inc.) or FIBRIN SEAL™ (FS). FLOSEAL™ is a gel constituting collagen derived particles and topical thrombin capable of being injected. It has been approved for uses including vascular sealing. Several other possible cationic agents may be but are not limited to one of the following cationic agents that remain protonated at low pH, poly (allyl amine), DEAE-Dextran, ethoxylated Poly(ethylenimine), and Poly(lysine). Other examples may be one of but are not limited to the following anionic agents for example, dextran sulfate, carboxymethyl dextran, carboxymethylcellulose, polystyrene sulfanate and chrondroitin sulfate. In a preferred embodiment, the first material may be DEAE Dextran and the second material may be polystyrene sulfanate.

FIG. 13 1370 illustrates the use of another dual component system DOPA (3,4-dihydroxyphenyl-L-alanine), a principle component responsible for mussel adhesive proteins, capable of forming a hydrogel in conducive conditions. Specifically, a component known as star block DOPA-block-PEG undergoes cross-linking in situ forming the hydrogel after an oxidation process converts the DOPA to O-quinone. This process forms a stable in situ hydrogel. Other examples are represented as dual components in FIG. 13 1370/1380. FIG. 13 1380 includes the use of an acrylate macromer solution and a dithiol solution injected into the infarct region for structural reinforcement. These components when mixed at the infarct site undergo a cross-linking reaction leading to the formation of a hydrogel. A specific embodiment may comprise the use of PEG triacrylate as the first component and PEG thiol as the second component introduced to the infarct zone via a dual lumen needle system discussed previously. In FIG. 13 1390, a glue-like component system may be employed. One embodiment may include the use of GRF glue that is made up of gelatin, resorcinol and formaldehyde (GRF) as a structurally reinforcing agent introduced to the infarct zone. To accomplish this, a two-part system may be used to induce cross-linking upon admixture of the components at the infarct zone. In other embodiments, the following structurally reinforcing components may be added along with GRF comprising the group consisting of the cross-linking agents polyglutamic acid, polylysine and WSC (water soluble carbodimides).

FIG. 14 illustrate the introduction and action of a single component or dual components to the infarct region for structural reinforcement. FIG. 14 illustrates the identification of the infarct region 1410 of the ventricle 1400 by methods previously described and subsequent multi-injection of the separate components to the site of damage 1420. In a dual component system, the two components 1430/1440 contact each other at the site and form reinforcing structural scaffold 1430/1440. In FIG. 15B, a single pseudoplastic or thixotropic agent is introduced to the area in multiple injections 1450 and structurally reinforces the wall 1460. These agents are introduced in final form and require no additional agents. FIG. 14 illustrates the addition of at least one agent 1430/1440/1450/1480 by multiple injections each at a different site 1405/1415 that requires an endogenous component or a temperature change 1460/1490 to convert to a structurally reinforcing form 1450/1470/1495. The structurally reinforcing agent(s) is localized to the infarct region via minimally invasive procedures discussed previously.

In addition, biocompatible viscosifiers for example type 1 gels may be added in combination with any of the single or multiple component systems illustrated. For example, hyaluronic acid or PVP may be used to increase the resistance of the active formula from natural degradation once introduced to the infarct zone. In one embodiment the viscosity of the treatment agent may be about 0-100 centipoise. In other embodiments, the viscosity of the treatment agent may be about 0-50 centipoise. In a preferred embodiment, the viscosity of the treatment agent may be about 25-40 centipoise. In a preferred embodiment, the viscosity of the treatment agent may be about 35 centipoise.

In one embodiment, any of the described agents may be introduced in one or more doses in a volume of about 1 μl to 1 ml. In another embodiment, any of the described agents may be introduced in one or more doses in a volume of about 1 μl to 300 μl. In another embodiment, any of the described agents may be introduced in one or more doses in a volume of about 1 μl to 100 μl. In a preferred embodiment, the any of the described agents may be introduced in one or more doses in a volume of about 1 μl to 50 μl. IV, and IC routes may be required which would involve larger treatment volumes (for example about 2 mls to about 250 mls).

Biocompatible dyes may be added to any single or combination components of any of the described embodiments to trace the components in the infarct region in any procedure. Other dyes may be added for experimental purposes to trace the deposition of any agent for example in a rat heart. Some examples of these dyes include but are not limited to Sudan Red B, Fat Brown RR, Eosin Y and Toluidine blue.

On the other hand, tissue adhesive components may also be added in combination with any of the single or dual component systems illustrated in FIGS. 12, 13 and 14. For example, Laminin-5, polyacrylic acid, Chitosan and water soluble chitosan may be used to increase the tissue retention of the active formulation. Laminin-5 is a basement membrane extracellular matrix macromolecule that provides an attachment substrate for both adhesion and migration in a wide variety of cell types, including epithelial cells, fibroblasts, neurons and leukocytes. Chitosan is the only natural positive ion polysaccharide obtained from deacetylated chitin. It possesses decomposability, good membrane forming state, biocompatibility, anti-fungal and anti-tumor function. Chitosan has excellent viscosity, compressibility and fluidity.

Single Components Suspended in a Delivery Medium

FIG. 15 illustrate flowcharts describing other methods to prevent the remodeling and ultimate thinning of the infarct region. As with several of the previously discussed methods, these methods provide a bulking or structurally reinforcing agent to the infarct region. In FIG. 15 1510, an agent comprising microparticles in solution (a dispersion) is introduced to the infarct region after identification of the infarct region as described previously. The microparticles may be a predetermined range of about 1 to about 200 microns. In one embodiment, the microparticles may be 20 microns or less. In a preferred embodiment, the microparticles may be 10 microns or less. The microparticle size delivered to an infarct region may be determined by the delivery method used. For example an intraventricular catheter may be used to deliver particles up to 200 microns that may avoid the risk of an embolism. One suspending solution for the microparticles may be water. On the other hand, the suspending solution may also be a solvent, for example dimethylsulfoxide (DMSO) or ethanol adjuvants. In one embodiment, a suspending solution along with the microparticles may be introduced to as a dispersion to an infarct region and the microparticles remain in the region as the solution dissipates into the surrounding tissue. Thus, the microparticles provide a structurally reinforcing bulk to the region. This may result in reduction of stress to the post infarct myocardium. It may also serve as a substrate for additional site for collagen deposition. In one embodiment, the dispersion (detailed above) may be injected in to the infarct zone during an open chest procedure via a minimally invasive procedure. In another embodiment, the minimally invasive procedure includes at least one subxiphoid and percutaneously. In another embodiment, the percutaneous introduction into the infarct zone may include one of intra-ventricular needle, transvascular catheter and retrograde venous perfusion.

FIG. 15 1520 illustrates a flow chart of an additional method similar to FIG. 15 1510 except that the microparticles precipitate out of the solution (the dispersion). In FIG. 15 1520, an agent including microparticles in solution (a dispersion) is introduced to the infarct region. The microparticles may be a predetermined size of 0 to 200 microns. In a preferred embodiment, the microparticles are 10 microns or less. In one embodiment, the suspending solution along with the microparticles may be introduced to the infarct region and the microparticles precipitate out of the dispersion in the region. Thus, the microparticles provide a structurally reinforcing bulk to the region. This may result in reduction of stress to the post infarct myocardium. It may also serve as a substrate for additional site for collagen deposition. In one embodiment, the dispersion (detailed above) may be injected in to the infarct zone during an open chest procedure via a minimally invasive procedure. In another embodiment, a minimally invasive procedure including the following of sub-xiphoid and percutaneously may be employed. In another embodiment, a percutaneous introduction into the infarct zone may include one of the of intra-ventricular needle, transvascular needle catheter and retrograde venous perfusion.

Several examples of the microparticles of FIG. 15 1510 and 15 1520 are illustrated in FIG. 16. FIG. 16 1610 illustrates the viscous liquid sucrose acetate isobutyrate (SAIB). SAIB is water insoluble. SAIB may be dissolved in a solvent or a combination of solvents for example, ethanol, dimethylsulfoxide, ethyl lactate, ethyl acetate, benzyl alcohol, triacetin, 2-pyrrolidone, N-methyl pyrrolidone, propylene carbonate or glycofurol. These solvents decrease the viscosity of SAIB in order to facilitate the introduction of this agent through a needle or lumen. In one embodiment, SAIB may be introduced accompanied by a solvent to the infarct region and the solvent dissipates at the site leaving behind the viscous SAIB in the region.

Other biocompatible polymer systems may be introduced to an infarct zone (FIG. 16 1620). Some of these agents are not only biocompatible but also substantially water insoluble similar to SAIB. Solvents or mixtures of solvents may be used to dissolve the polymer in order to facilitate introduction to the infarct zone. In one embodiment, a biocompatible water insoluble polymer may include the following consisting of polylactides, polyglycolides, polycaprolactones, polyanhydrides, polyalkylene oxates, polyamides, polyurethanes, polyesteramides, polydioxanones, polyhydroxyvalerates, polyacetals, polyketals, polycarbonates, polyorthoesters, polyphosphazenes, polyhydroxybutyrates, polyalkylene succinates, and poly(amino acids). Any one of these insoluble polymers may be dissolved in solvents for example Diglyme, dimethyl isosorbide, N-methyl-2-pyrrolidone, 2-pyrrolidone, glycerol, propylene glycol, ethanol, tetraglycol, diethyl succinate, solketal, ethyl acetate, ethyl lactate, ethyl butyrate, dibutyl malonate, tributyl citrate, tri-n-hexyl acetylcitrate, dietyl glutarate, diethyl malonate, triethyl citrate, triacetin, tributyrin, diethyl carbonate, propylene carbonate acetone, methyl ethyl ketone, dimethyl sulfoxide dimethyl sulfone, tetrahydrofuran, capralactum, N,N-diethyl-m-toluamide, 1-dodecylazacycloheptan-2-one, 1,3-dimethyl-3,4,5,6-tetrahydro-2(1H)-pyrimidinone and glycerol formal to form an injectible polymer solution. The dispersion may be introduced into the infarct region of the heart where the solvent may dissipate and the polymer may precipitate out of the dispersion to structurally reinforce the infarct regional wall. In one embodiment, the disclosed polymers may be used in any combination as co-polymers of two or more polymers introduced to the infarct region.

FIG. 16 1630 illustrates a flowchart describing the use of a vinyl polymer and acrylate biocompatible polymer system. Once injected into an infarct zone, the vinyl polymer/acrylate agent contacts water and the polymer precipitates thus reinforcing the surrounding tissue of the infarct region. In one embodiment, the vinyl polymer/acrylate agent includes the following such as polyvinyl butyral, PBMA-HEMA, PEMA-HEMA, PMMA-HEMA and other acrylate copolymers that dissolve in ethanol, acetone and I-PA. In another embodiment, the vinyl polymer/acrylate agent introduced to the infarct region may be EVAL™ that has a solid phase or melt phase forming process. EVAL™ Resins have a high crystalline structure. Thermoforming grades of EVAL™ resins have monoclinic crystalline structure while most polyolefins have either a hexagonal or orthorhombic type structure. This characteristic provides flexibility within its thermoforming capabilities. In another embodiment, the vinyl polymer/acrylate agent introduced to the infarct region may be BUTVAR™ (polyvinyl butyral). In one embodiment, the agent may be P(BMA co-MMA) (Aldrich Chem.) in Diglyme. In another embodiment, the agent may be EVAL™, a co-polymer of ethylene and vinyl alcohol (EVAL Co. of America, Houston, Tex.) in dimethyl acetamide. In another embodiment, the polymer may be PLGA (poly(lactide co-glycolide) (Birmingham Polymers, Birmingham, Ala.) in Diglyme.

Other components may act as a substrate for endogenous collagen deposition and protect the precipitated or remaining microparticles described in FIG. 16 from erosion. As the reinforcing gel degrades, the highly stable and smooth microparticles may be exposed to the fibroblast cell population occupying the site. This triggers the production of collagen to replace the decomposing gel. Therefore, the infarct zone may be reinforced by the collagen replacement of the temporary gel. The dispersed material includes the following group of microparticle materials consisting of PMMA, P(MMA-co BMA), carbon microparticles (Durasphere), poly styrene, cross-linked acrylic hydrogels and PLGA. In another embodiment, the cross-linked acrylic hydrogel may include the following for example HEMA, AA, AMPS, acrylamide, N, N, di-methyl acrylamide, diacetone acrylamide, styrene sulfonate, and di or tri functional monomers. The di or trifunctional monomers may be EGDMA and DVB. Another example of durable microparticles includes pyrolytic carbon-coated microparticles. One example of pyrolytic carbon-coated microparticles was originally produced for urinary incontinence (Carbon Medical Technologies) and trisacryl gelatin microparticles for use as embolization particles (Biosphere). In addition, the use of highly crystalline (and hydrolysis resistant) PLGA microparticles may outlast the carrier gel and also provide a useful substrate for collagen deposition.

One or more contrast agents 1540 and/or suitable treatment agent(s) 1550 may accompany the previously detailed components as a treatment of the infarct region. The contrast agent or treatment agent may be conjugated to or dissolved into the structural component prior to introduction to the infarct area. The contrast agents may be used for detection in X-ray or MR analysis. The agents that may accompany the reinforcing component(s) may include but are not limited to angiogenic agents, ACE inhibitors, angiotensin receptor blockers, SRCA pump (sarcoplasmic reticulum calcium pump) increasing agents, phospholamban inhibitors and anti-apoptotic drugs. These agents may be in the form of small molecules, peptides, proteins or gene products. The small molecules may be optionally conjugated to a component of the solution, dispersed in solution, or dissolved in solution to improve the adhesion of the reinforcing components to the tissue. One embodiment is to conjugate a peptide with a conserved region that mediates adhesion processes. Another embodiment includes the use of a specific peptide conjugate with a RGD (arginine-glycine-asparagine) motif in the presence of the reinforcing component. In further embodiments, the RGD motif peptide may include von Willebrand factor, osteopontin, fibronectin, fibrinogen, vitronectin, laminin and collagen.

In one embodiment, any of the described agents may be introduced in one or more doses in a volume of about 1 µl to 1 ml. In another embodiment, any of the described agents may be introduced in one or more doses in a volume of about 1 µl to 300 µl. In another embodiment, any of the described agents may be introduced in one or more doses in a volume of about 1 µl to 100 µl. In a preferred embodiment, the any of the described agents may be introduced in one or more doses in a volume of about 1 µl to 50 µl.

Collagen Cross-linking Agents for Structural Reinforcement

FIG. 17 illustrates a flowchart describing a method to structurally reinforce the infarct region of the ventricle 1710. As previously mentioned, thinning is a key factor in the cascade of events following remodeling of the infarct region. One factor contributing to the thinning is collagen degradation by MMPs (matrix metalloproteins) and collagen helix slippage due to hemodynamic stress. The collagen slippage generates infarct scar expansion that leads to additional remodeling and remote zone hypertrophy. Previous inventions to prevent collagen slippage include a suturing procedure (Kelley et al., Circ., 1999; 99:135-142) This involves directly suturing a epicardial polymer mesh to the region. According to one embodiment, agents will be introduced to the region by a minimally invasive procedure to prevent collagen slippage. An agent or dispersion will be introduced in one embodiment by multiple injections to the infarct zone then the agent will react with the collagen scar directly to cross-link it. This results in prevention of slippage and strength to the regional wall. In one embodiment, the agent (detailed above) may be injected in to the infarct zone during an open chest procedure via a minimally invasive procedure. In another embodiment, the minimally invasive procedure may include sub-xiphoid and percutaneously. In another embodiment, the percutaneous introduction into the infarct zone may comprise one of intra-ventricular needle, transvascular needle catheter and retrograde venous perfusion.

A contrast agent or treatment agent may be conjugated to or dissolved into the structural component prior to introduction to the infarct area. The agents were detailed Several possible cross-linking agents are illustrated in FIG. 18 to illustrate the possible agents of 1720 to prevent collagen slippage 1730. The agent injected into the infarct region may be polyfunctional (either hetero or homopolymer). Another important feature of the cross-linking agent is the ability of the agent to cross-link to the side groups of the amino acids of the collagen (type I and III). In one embodiment, the agent is soluble in a biocompatible water miscible solvent that is capable of being drawn out of the dispersion by aqueous fluid present in the myocardium. This enables the cross-linking agent the ability to precipitate out into the infarct region minimizing migration of the cross-linking agent out of the area. In another embodiment, the biocompatible solvent used in the presence of the cross-linking agent may be the following Diglyme and dimethyl isosorbide. Collagen is made up of a large number of lysine and hydroxyproline residues that carry reactive side groups of primary amines and hydroxyl groups respectively. In the following examples, the cross-linking agents react with at least one of these side groups. FIG. 18 1810 illustrates a flowchart describing a method using polyepoxy functional resins for cross-linking the collagen. In one embodiment a polyepoxyl functional resin may be introduced to the infarct region. In another embodiment, the polyepoxy functional resin may comprise the following consisting of Bisphenol A epoxies (Shell 828), Epoxy-Novolak resins (Ciba 1138 and 1139, Dow 431), homopolymers of glycidyl methacrylate (GMA) or copolymers of GMA with other acrylates. In another embodiment, the polyepoxy functional resins may include a multifunctional epoxide. In another embodiment, the polyepoxy functional resins may include an acrylate. The later resins, multifunctional epoxides and acrylate, are based on a cubic silicone with eight epoxide or acrylate functionalities (Silsesquixanes). In another embodiment, the polyepoxy functional resins may include a tetra-functional epoxide silicone. In another embodiment, the polyepoxy functional resins may include di-functional epoxide silicone.

FIG. 18 1820 illustrates a flowchart describing the use of polyisocyanates as the cross-lining agent. In one embodiment, the cross-linking agent used to link the collagen may comprise a polyisocyanate. In another, the polyisocyanate may include the following the biuret of hexamethylene di-isocyanate and isocyanurate of hexamethylene di-isocyanate. Both of these products are manufactured commercially under the name DESMODUR N 100 and DESMODUR 3300 respectively (commercially available from Bayer). FIG. 18 1830 illustrates a flowchart describing the use of aromatic halogenated compounds as a possible collagen cross-linking agent. In one embodiment, the agent used to cross-link the collagen to prevent slippage and structurally reinforce the infarct region may include a halogenated compound. In another embodiment, the halogen compound used to cross-link the collagen may include 1,5 difluoro 2,4 dinitrobenzene (DFNB).

Polyhydroxyl aromatics (resorcinol groups) such as vegetable tannins have been used to cross-link collagen for processing animal hides into leather. FIG. 18 illustrates a flowchart describing the use of these resorcinol groups for collagen cross-linking. Solvent soluble resorcinol-formaldehyde resins contain numerous resorcinol groups. A methylene bridge and/or an ether bridge connect the resorcinol groups. RESORCINOL™ is capable of cross-linking collagen but one problem is that it is corrosive and water miscible in its monomeric form. In one embodiment, the cross-linking agent to secure the collagen and structurally reinforce the infarct region may be a resorcinol-formaldehyde resin.

FIG. 18 1850 illustrates a flowchart describing the use of agents that terminate in an acrylate group as a potential cross-linking agent to prevent collagen slippage in the infarct region and structurally reinforce the ventricular wall. These acrylate-terminating agents react with the primary amine groups of the collagen and form a stabilizing cross-link. In one embodiment, the cross-linking agent may be an acrylate-terminating agent. In another embodiment, the acrylate-terminating agent used to cross-link the collagen may include one of the following water-insoluble agents urethane-acrylates and epoxy-acrylates. These compounds are commercially available (Cognis Corp, OH). Another example of a cross-linking agent is illustrated in the flowchart of FIG. 18 1860. Lysyl oxidase discussed earlier may be use alone or in combination with other agents to cross-link the collagen for prevention of slippage and as a structurally reinforcing agent in the infarct region. Lysyl oxidase is an enzyme that oxidatively deaminates lysine side groups and forms reactive aldehyde groups capable of forming strong cross-linking bonds with the collagen. In one embodiment, lysyl oxidase may be introduced to the infarct region to cross-link the existing collagen for prevention of slippage.

In the final flowchart example of FIG. 18 1870 illustrates a flowchart describing the use of microparticles to cross-link and stabilize the collagen in the infarct region. One example includes the use of surfactant free styrene latex particles in narrow size distributions that also contain the following functional surface groups comprising chloromethyl, epoxy and aldehyde. The aldehyde surface groups may be tightly packed therefore borohydride reduction would not be necessary for a stable linkage. Chloromethyl groups react with primary and secondary amines thus forming a stable cross-link. Other possible functional reacting groups may include succinimidyl ester, benzotriazole carbonate and p-nitrophenyl carbonate. Other possible functional groups may be used. In one embodiment, the size limitation of the microparticles may include submicron to single digit micron size. This size range prevents the microparticles that may backwash out of the site from causing an embolic hazard. In other embodiments, the cross-linking agent may be a functionalized surfactant free styrene latex microparticle. Several examples exist of these styrene microparticles. Examples of commercially available functional stryrene microparticles are manufactured by Interfacial Dynamics Corporation and Magsphere.

Additionally, any one of these agents illustrated in FIGS. 17 and 18 may be accompanied by one or more contrast agent 1740 and/or suitable agent(s) 1750 for treatment of the region. The contrast agent or treatment agent may be conjugated to or dissolved into the structural component prior to introduction to the infarct area. The agents that may accompany the reinforcing component(s) may include but are not limited to angiogenic agents, ACE inhibitors, angiotensin receptor blockers, SRCA pump increasing agents, phospholamban inhibitors and anti-apoptotic drugs. These agents may be in the form of small molecules, peptides, proteins or gene products. The small molecules may be optionally conjugated to a component of the solution, dispersed in solution, or dissolved in solution to improve the adhesion of the reinforcing components to the tissue. One embodiment is to conjugate a peptide with a conserved region that mediates adhesion processes. Another embodiment includes the use of a specific peptide conjugate with a RGD (arginine-glycine-asparagine) motif in the presence of the reinforcing component. In further embodiments, the RGD motif peptide comprises the following consisting of von Willebrand factor, osteopontin, fibronectin, fibrinogen, vitronectin, laminin and collagen.

Prevention of Myocardial Edema and "Cementing" of the Infarct Region

FIG. 19 illustrates flowcharts describing the introduction of clotting factors immediately after an MI 1900. One of the initial responses of the process post-MI is myocardial edema. The edema is composed of extravasated blood evident within a few hours after infarction. This is followed by its dissolution within the next few hours. The process that occurs immediately post-MI is that the infarct regional wall thickens and then it thins. The present invention illustrated in FIG. 19 introduces one or more clotting factors to the region thereby "cementing" the now clotted blood to reinforce the wall and thicken the wall 1910. FIG. 19 1920/1930 illustrates one method to clot the blood using a dual solution technique. In one embodiment, the first solution includes calcium chloride and thrombin 1920 and the second solution 1930 includes fibrinogen and transexamic acid. Transexamic acid is an anti-fibrinolytic agent. The introduction of these two solutions to the infarct region sequentially result in localized clotting of the blood that forms a structurally reinforcing mass 1940 within the region preventing thinning of the infarct site. In another embodiment, intravenous pressure perfusion may be used to deliver the clot inducing solutions to the infarct zone. This prevents the possibility of the clot releasing into the arterial circulation. FIG. 19 1950 illustrates a flowchart describing the use of shear-activated platelet fraction to induce localized clotting. This platelet fraction may be isolated from the MI subject's own blood or another source. FIG. 19 1960 illustrates a flowchart of other initiators of the clotting cascade. These factors encompass factors that are termed intrinsic and extrinsic factors. Intrinsic factors initiate clotting in the absence of injury. Extrinsic factors initiate clotting that is caused by injury. In one embodiment, the clotting factor used to cease myocardial edema and reinforce the ventricular wall at the infarct zone may comprise the following consisting of von Willebrand Factor (vWF), High Molecular Weight Kininogen (HMWK), Fibrinogen, Prothrombin, and Tissue Factors III-X. In another embodiment of the present invention, any combination of the clotting factors mentioned previously may be used that may provide increased tensile strength the infarct regional wall.

Matrix Metalloproteinase Inhibitors Use in the Infarct Region

After an MI injury occurs macrophages tend to infiltrate the infarct region. The macrophages release matrix metalloproteinases (MMPs). As members of a zinc-containing endoproteinase family, the MMPs have structural similarities but each enzyme has a different substrate specificity, produced by different cells and have different inducibilities. These enzymes cause destruction in the infarct zone. One important structural component destroyed by MMPs is the extracellular matrix (ECM). The ECM is a complex structural entity surrounding and supporting cells that are found within mammalian tissues. The ECM is often referred to as the connective tissue. The ECM is composed of 3 major classes of biomolecules; structural proteins: for example collagen and elastin, specialized proteins for example fibrillin, fibronectin, and laminin, and proteoglycans: these are composed of a protein core to which is attached long chains of repeating disaccharide units termed of glycosaminoglycans (GAGs) forming extremely complex high molecular weight components of the ECM. Collagen is the principal component of the ECM and MMP induce ECM degradation and affect collagen deposition. Inhibitors of MMP(s) exist 1970 and some of these inhibitors are tissue specific. It was previously demonstrated that acute pharmacological inhibition of MMPs or in some cases a deficiency in MMP-9 that the left ventricle dilatation is attenuated in the infarct heart of a mouse (Creemers, E. et.al. "Matrix Metalloproteinase Inhibition After Myocardial Infarction" A New Approach to Prevent Heart Failure? Circ Res. Vol 89 No. 5, 2315-2326, 1994). The inhibitors of MMPs are referred to as tissue inhibitors of metalloproteinases (TIMPs). Synthetic forms of MMPIs also exist for example BB-94, AG3340, Ro32-355b and GM 6001. It was previously shown that MMPIs reduce the remodeling in the left ventricle by reducing wall thinning. These experiments were performed on rabbits. In addition, this study also demonstrated that MMPI increases rather than decreases neovascularization in the subendocardium (Lindsey et. al. "Selective matrix metalloproteinase inhibitors reduce left ventricle remodeling but does not inhibit angiogenesis after myocardial infarction," Circulation 2002 Feb. 12;105 (6): 753-8). In the one embodiment MMPIs may be introduced to the infarct region to delay the remodeling process by reducing the migration of fibroblasts and deposition of collagen and prevent ECM degradation, reduce leukocyte influx and also reduce wall stress. In one embodiment, the MMPIs may include the following TIMPs including but not limited to TIMP-1, TIMP-2, TIMP-3 and TIMP-4 introduced to the infarct region in combination with introducing any of the described structurally reinforcing agents to the infarct region. In another embodiment, naturally occurring inhibitors of MMPs may be increased by exogenous administration of recombinant TIMPs. In another embodiment, the MMPI comprises a synthetically derived MMPI introduced to the infarct region in combination with introducing any of the described structurally reinforcing agents to the infarct region. The introduction of MMPIs to the infarct zone may be accomplished by several different methods. It is critical that the introduction of these MMPI agents be accomplished by a minimally invasive technique. In one embodiment, MMPI agents will be introduced to the region by a minimally invasive procedure to prevent ECM degradation. An agent or dispersion will be introduced in one embodiment by multiple injections to the infarct region. This results in prevention of ECM degradation and increased strength to the regional wall. In one embodiment, the MMPI agent may be injected in to the infarct zone during an open chest procedure via a minimally invasive procedure. In another, the minimally invasive procedure may include one of sub-xiphoid and percutaneously. In another embodiment, the percutaneous introduction into the infarct zone may include one of intra-ventricular needle, transvascular needle catheter and retrograde venous perfusion. In addition, the MMPI agents may be introduced via suspension or sustained release formula for example introduced in microparticles detailed in the three-component system of FIG. 6. In one embodiment, the introduction of MMPIs may follow any of the cross-linking events that prevent collagen slippage. In another embodiment, the cross-linking agent may be cleared from the targeted infarct area prior to introducing the MMPI(s).

After an MI, the myocardium may be significantly affected resulting in a percentage of the tissue being akinetic or dyskinetic. This often occurs when the MI is caused by an occluded left anterior descending artery. Moderate infarct where 20 to 40 percent of the tissue is affected decreased cardiac output occurs resulting in the activation of the neurohormonal system (via a RAAS (renin-angiotensin-aldosterone) system). Thus, the neurohormonal activation causes an increase in blood pressure resulting in further stress to the myocardium. The induced necrosis results in an inflammatory response that clears the site of the necrotic tissue and ultimately leads to thinning of the myocardium. The cycle continues with an increase in stress on the myocardium and may result ultimately in heart failure.

Structural Reinforcement of the Infarct Zone by Inducible Gel Systems

FIG. 20 illustrates a flowchart describing the introduction of photo-polymerizable hydrogels to the infarct region for structural reinforcement of the infarct zone (2000). Hydrogels have been used before in tissue engineering applications. These gels are biocompatible and do not cause thrombosis or tissue damage. These hydrogels may be photo-polymerized in vivo and in vitro in the presence of ultraviolet (UV) or visible light depending on the photo initiation system. Photopolymerizing materials may be spatially and temporally controlled by the polymerization rate. These hydrogels have very fast curing rates. A monomer or macromer form of the hydrogel may be introduced to the infarct zone for augmentation with a photo initiator. Examples of these hydrogel materials include PEG acrylate derivatives, PEG methacrylate derivatives or modified polysaccharides.

Visible light 2030/2160 maybe used to initiate interfacial photopolymerization of a polyoxyethylene glycol (PEG)-co-poly(alpha-hydroxy acid) copolymer 2100 based on PEG 8000 macromonomer in the presence of an initiator for example Quanticare QTX. Initiator 2-hydroxy-3-[3,4,dimethyl-9-oxo-9H-thioxanthen-2-yloxy]N,N,N-trimethyl-1-propanium chloride photo-initiator may be obtained as Quantacure QTX. This is a specific water-soluble photo-initiator that absorbs ultraviolet and/or visible radiation and forms an excited state that may subsequently react with electron-donating sites and may produce free radicals. This technology has been used to demonstrate adherence to porcine aortic tissue, resulting in a hydrogel barrier that conformed to the region of introduction. The resulting matrix was optimized in vitro and resulted in the formation of a 5-100 microns thick barrier (Lyman, MD et.al. "Characterization of the formation of interfacially photopolymerized thin hydrogels in contact with arterial tissue Biomaterials" 1996 Feb.;17 (3):359-64). Scaffolding 2040/2130 may be directed to only the desired area of the ventricle using minimally invasive procedures discussed previously. The structural reinforcement could remain in place until it is cleared or degraded 2050/2170.

One embodiment includes introduction to the infarct zone of benzoin derivatives, hydroxalkylphenones, benziketals and acetophenone derivatives or similar compounds. These photo-initiators form radicals upon exposure to UV light by either photocleavage or by hydrogen abstraction to initiate the reaction see FIG. 21A-21E. The source of the UV or visible light may be supplied by means of a catheter 2160 for example a fiber optic tip catheter or lead on a catheter illustrated in FIG. 21C or transdermally. FIG. 22A-22B illustrates a catheter assembly that may be used to deliver a light sensitive material. The catheter 2210 is designed to provide a delivery device with at least one lumen for one or more agent(s) 2230 and a light source 2220 for modification of the delivered agent. The catheter controller 2240 may house a switch 2250 for the light source 2220 and a controller for agent delivery 2260. In another embodiment, the photo-initiator Camphorquinone may be used. Camphorquinone has been used extensively in dental applications and has a lambda max of 467 nanometers. For example, this agent can be activated by a GaN blue LED on the tip of a catheter. One embodiment includes the use of visible light at the end of the delivery catheter to induce the polymerization event in the presence of a light sensitive initiator. Another embodiment includes the use of the photoinitiator, Camphorquinone that may facilitate the cross-linking of the hydrogel by a light on the tip of a catheter within the infarct region. Another embodiment includes the use of the photoinitiator, Quanticare QTX that may facilitate the cross-linking of the hydrogel by a light on the tip of a catheter within the infarct region. Another embodiment includes the use of a catheter with a UVA light source to induce the polymerization event in the presence of a light sensitive initiator. Other initiators of polymerization in the visible group include water soluble free radical initiator 2-hydroxy-3-[3,4, dimethyl-9-oxo-9H-thioxanthen-2-yloxy] N,N,N-trimethyl-1-propanium chloride. This cascade of events provides the necessary environment for initiation of polymerization of suitable vinyl monomers or pre-polymers in aqueous form within the infarct region (Kinart et. al. Electrochemical atudies of 2-hydroxy-3-(3,4-dimethyl-9-oxo-9H-thioxanthen-2-yloxy)N,N,N-trimethyl-1-propanium chloride" J. Electroanal. Chem 294 (1990) 293-297).

One possible method of introducing a photo-polymerizable agent to the infarct region is illustrated in FIG. 21A-21E. In one embodiment the photo-polymerizable material is introduced to the infarct regions during an open chest procedure or via a minimally invasive procedure 2130. In another embodiment, the minimally invasive procedure includes the following sub-xiphoid and percutaneously. In another embodiment, the percutaneous introduction into the infarct zone may comprise one of the following consisting of intraventricular needle, transvascular needle catheter and retrograde venous perfusion. A single bore needle catheter 2120 may be used to introduce the photo-polymerizable material into the infarct zone 2140. Once the agent is introduced to the region, several heartbeats clear the excess agent into the ventricle 2150 and this excess agent is cleared from the cardiac region. Once the excess material is cleared, the light source 2160 may be introduced to induce polymerization 2170. Thus, the structural reinforcement is confined to the local area of damage where tissue augmentation is required. As illustrated in FIG. 20, the scaffolding may be made up of a resistant material or a biodegradable material 2050. Some examples of biodegradable materials include PEG-co-poly (α-hydroxy acid) diacrylate macromers, derivatives of this material that vary the length and composition of the α-hydroxy acid segment in the co-polymer, poly(propylene fumarate-co-ethylene glycol and hyaluronic acid derivatives. The degradation rates of the polymers may be varied according to the optimum length of time the material is required to remain in the infarct region. It has been shown that the degradation rates of theses gels can be modified by the appropriate choice of the oligo(α-hydroxy acid) from as little as less than one day to as long as 4 months (Sawhney, A. S. et.al., Bioerodible Hydrogels Based on Photopolymerized Poly(ethylene glycol)-co-poly(a-hydroxy acid) Diacrylare Macromers. Macromolecules (1993) 26, 581-587). Any of these polymer chains may be formed in the presence of a photoinitiator such as Quanticare QTX and a light source.

Figure 21A:
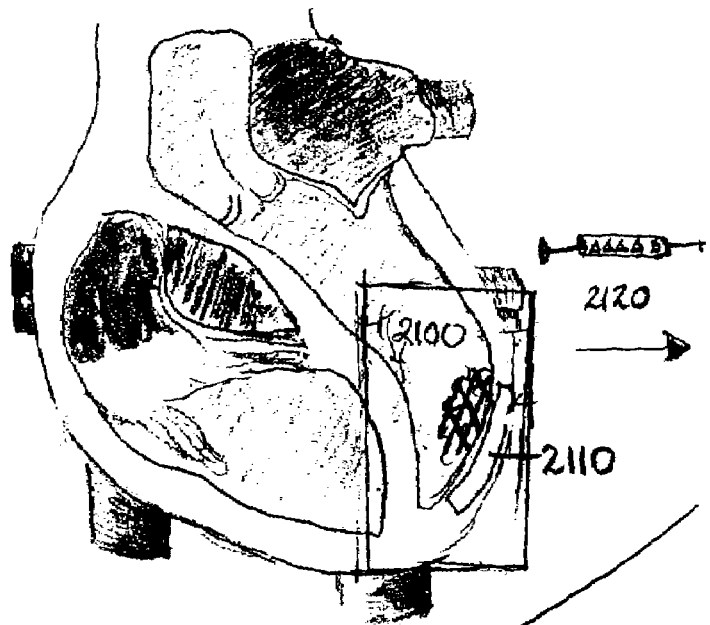
Figure 21B:
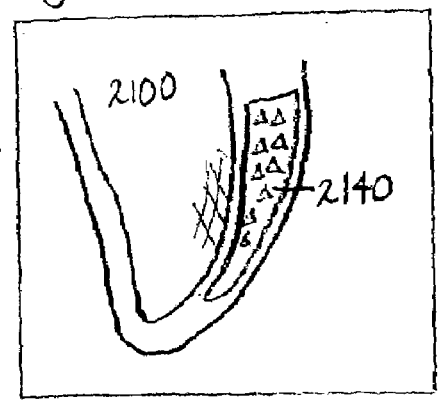
Figure 21C:
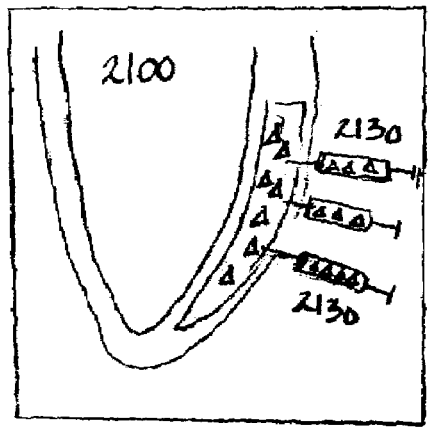
Figure 21D:
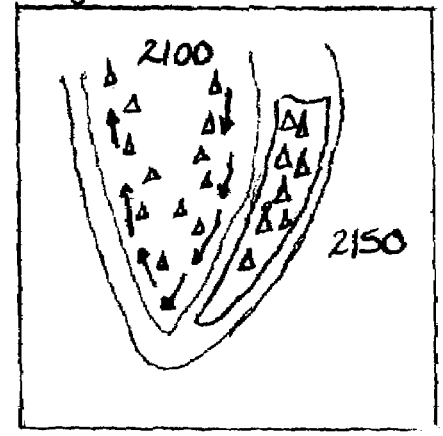
Figure 21E:
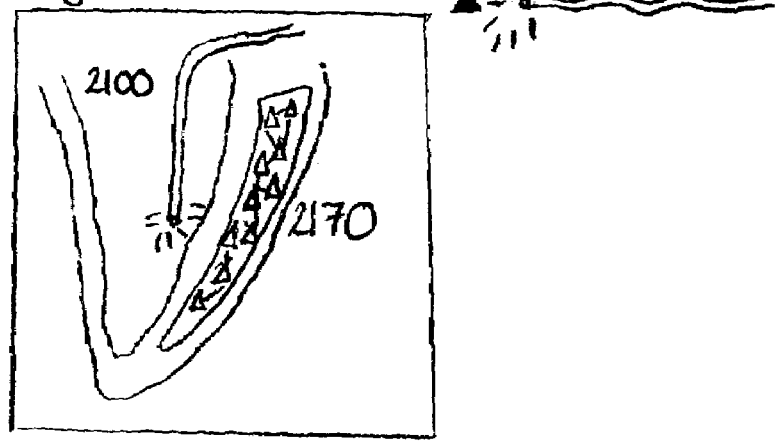

FIG. 21A-21E illustrates the process of introduction of a potential photo-polymerizable material to the infarct zone. FIG. 21A and FIG. 21B illustrates the introduction of the material to the site 2100 and 2110. FIG. 21C illustrates the clearing of the excess material into the ventricle 2150. Then, in FIG. 21C the light source may be introduced via a catheter to polymerize the material 2160. The material remains in the site 2170 as structural reinforcement until at which time it degrades or not depending on the material used.

In one embodiment, any of the described agents may be introduced in one or more doses in a volume of about 1 μl to 1 ml. In another embodiment, any of the described agents may be introduced in one or more doses in a volume of about 1 μl to 300 μl. In another embodiment, any of the described agents may be introduced in one or more doses in a volume of about 1 μl to 100 μl. In a preferred embodiment, the any of the described agents may be introduced in one or more doses in a volume of about 1 μl to 50 μl.

FIG. 24A and FIG. 24B illustrates a catheter assembly that may be used to deliver a dual component composition. In FIG. 24A, component 1 2410 and component 2 2420 are housed 2430 in separate lumen of a delivery device. Delivery of the components is controlled by a handle 2470 at the base of the device. The handle 2470 is rotated to allow one needle to extend and then the other. Only one needle is engaged at a time. A cross-sectional view illustrated in FIG. 24B illustrates the first needle port 2450 and the second needle port 2460 and the central tendon 2480 that controls the needle extention. At the distal end 2490 of the device, FIG. 24C, the handle is turned and the needle extends while retracting the other needle. In one embodiment, this catheter device may be used to deliver components to the infarct region of a left ventricle intramyocardium. In another embodiment, this catheter device may be used to deliver a first component to the area and a second component after the excess first component is allowed some time to wash away.

FIG. 25A-25D illustrates the introduction of dual components using the catheter device of FIG. 24 to an infarct region while avoiding the possibility of injecting the agents into the exact same site. The delivery device of FIG. 24 is used to deliver the components to the infarct region. The infarction is illustrated as a region between the endocardium and the epicardium. The device 2540 is advanced to this site and the first component is delivered by extending needle 1 2550 and the component 2560 is dispersed in the infarct area. Then this needle 2550 is retracted while the second needle 2570 is extended. The second component 2580 is dispersed. The delivery of the two components to the area is capable of forming a gel 2590.

FIG. 26 illustrates the delivery of the catheter device illustrated in FIG. 24 and 25. Both of the components are delivered through a lumen of a catheter (for example a balloon catheter) 2630/2640 at the same time. For example, the first component 2650 may be delivered through a venous route 2610 and the second component 2660 may be delivered through an arterial route 2620. This procedure ensures the appropriate pressure balance to contain the components in the microcirculation. This avoids leakage to either the venous or arterial side. The driving pressure for the venous side is greater than 100 mm Hg (delta P) 2670 is calculated to ensure the confinement of the component in capillary level) and the arterial side does not require an external pressure gradient. The arterial side may be accomplished by infusion. In one embodiment, the catheter may be used to deliver the first component through the venous tree followed by the second component through the arterial tree. This device may be used to deliver any of the component combination methods described in the embodiments detailed previously.

Ventricular Plugs

Another method for reinforcing the damaged wall of a ventricle may include introduction of a solid material to the damaged area. The solid material may be used to fill or bulk the region by introducing plugs of the solid material to the site and may increase the compliance of the ventricle. These materials may be made of organic or silicon-based polymers, biodegradable polymers, non-biodegradable polymers, engineered biomaterials and/or metals. In one embodiment the plug may have barbs or pointed ends in order to lodge the material into the area and ensure it remains there. In other embodiments, the sealant or plug may add bulk to the thinning wall of an infarct post myocardial infarction. This may result in an increase in the modulus of elasticity of the damaged area. In other embodiments, the sealant or plug may invoke an inflammatory response to the infarct region. The inflammatory response will result in the increase in angiogenic response capable of causing recruitment and activation of fibroblasts that deposit additional collagen to bulk the thinning infarct region and increase the modulus of elasticity of this region. Still, other embodiments include the addition of a plug to the damaged region of a ventricle that may add strength to the wall and also cause an inflammatory response to the region.

In one embodiment, the plug supplied to the damaged region of the ventricle may include biocompatible organic components. In other embodiments, the plug supplied to the damaged region of the ventricle may include a biocompatible silicone-based polymer. In other embodiments, the plug supplied to the damaged region of the ventricle may include biocompatible biodegradable polymers for example PLGA, Poly(hydroxyvalerate) and poly ortho esters etc. In other embodiments, the plug supplied to the damaged region of the ventricle may include biocompatible non-biodegradable material for example polypropylene and PMMA. In still further embodiments, the plug supplied to the damaged region of the ventricle may include biocompatible metal compounds for example 316L, Co—Cr alloy, Tantalum and titanium etc. Another advantage to using a plug directly implanted in the region of interest may be to add additional surface components to the plug such as side groups. These side groups may contain reactive side groups that react with exogenously supplied or endogenous collagen, for example type I and type III collagen. Since collagen contains a significant number of lysine and hydroxyproline residues, these residues harbor primary amine and hydroxyl groups capable of reacting with other moieties. In one embodiment, the plug supplied to the damaged region of the ventricle may include surface aldehyde groups capable of reacting with the primary amines of lysine in collagen.

The size and the shape of the plugs may vary depending on the situation. For example, polymeric plugs mentioned previously may be machined, injection molded, extruded or solution cast. In one embodiment, the shape of the plug may be elongated and thin in order to facilitate delivery by a catheter device. These plugs may also possess a barb or side protrusion to prevent the plug from slipping out of the site once it is introduced to the damaged region of the ventricle. In other embodiments, the plug may be created in the shape similar to a screw or a helix. In one embodiment, the plug may be a polymeric material. In other embodiments, the plug may be a polymeric material with SS anchors for example, a plug with a stainless steel band with anchors for embedding the plug into the site of interest. The size of the plug may also vary. In one embodiment, the radial diameter of the plug may be from about 0.1 mm to about 5 mm. In other embodiments, the radial diameter of the plug may be about 0.2 mm to about 3 mm. In other embodiments, the length of the plug may be from about 1 to about 20 mm. In other embodiments, the length of the plug may be about 2 mm to about 12 mm. In addition to the size and shape of the plug, the number of plugs supplied to a region in the ventricle may also vary depending on the extent of damage and the condition of the subject. In one embodiment, the number of plugs supplied to the region may about 1 to about 200. In other embodiments, the number of plugs supplied to the region may be about 5 to about 50. In still further embodiments, the number of plugs supplied to the region may be about 2 to about 20.

In a preferred embodiment, the plug may be a processed biocompatible biomaterial. This biomaterial may be advantageous for recruiting cells to the damaged region for additional strength to the site. One example of a biomaterial includes porcine derived Small Intestine Submucosa, termed SIS. This engineered biomaterial may be supplied from DePuy Inc and the Cook Group. It is available in sterile sheets. SIS includes the complete small intestinal sub-mucosa, including de-cellularized extracellular matrix (ECM) in a native configuration. It also includes important endogenous growth factors adhered to the matrix. SIS has previously been shown to recruit pluripotent bone marrow derived stem cells that adhere to the SIS and induce healing. SIS has previously been used to repair rotator cuff injuries, diabetic foot ulcers and hip joints. SIS has been shown to re-absorb after a period of approximately 3 to 4 months. After re-absorption, the healed live tissue has replaced the matrix. In one embodiment, small disks of SIS may be supplied to a region in the ventricle for example an infarct region. The SIS disks may provide similar recruitment of cells into the damaged myocardium. These cells may then transform into viable muscle tissue and may form contractile myocytes.

There are several methods that may be used to introduce any of the plugs described. An optimum approach for introduction of the plugs may include but is not limited to introduction to the infarct region and/or the border zone of an infarct region during an open-heart procedure; or through a minimally invasive procedure for example sub-xiphoid or percutaneously for example with an intra-ventricular catheter or transvascular catheter (venous or arterial). One embodiment for introducing the plugs to the infarct region may include directly introducing the plugs to the site during an open-heart surgical procedure.

One or more contrast agents and/or suitable treatment agent(s) may accompany the previously detailed components. The contrast agent or treatment agent may be dispersed into, conjugated to, or dissolved into the plug component prior to introduction to the infarct area. The contrast agents may be used for detection in X-ray or MR analysis. The agents that may accompany the reinforcing component(s) may include but are not limited to angiogenic agents, ACE inhibitors, angiotensin receptor blockers, SRCA pump (sarcoplasmic reticulum calcium pump) increasing agents, phospholamban inhibitors and anti-apoptotic drugs. These agents may be in the form of small molecules, peptides, proteins or gene products. The agents may be optionally conjugated to a component of the resin mix that makes the plug, dispersed in the plug solution prior to forming the plug, or dissolved in the plug solution prior to forming the plug, or packed into machined pockets or reservoirs in the plug to elicit a biological effect (e.g. improve implant adhesion, recruit cells, promote healing). One embodiment is to conjugate a peptide with a conserved region that mediates adhesion processes. Another embodiment includes the use of a specific peptide conjugate with a RGD (arginine-glycine-asparagine) motif or the peptide receptor to RGD, such as DDM (aspartate-aspartate-methionine) in the presence of the reinforcing component. In further embodiments, the RGD motif peptide may include von Willebrand factor, osteopontin, fibronectin, fibrinogen, vitronectin, laminin and collagen.

In the foregoing specification, the embodiments have been described with reference to specific exemplary embodiments. It will, however, be evident that various modifications and changes may be made without departing from the broader spirit and scope of the invention as detailed in the appended claims. The specification and drawings are, accordingly, to be regarded in an illustrative rather than a restrictive sense.

EXAMPLES

Example 1. Example 1 illustrates one possible three-component system described in FIG. 7 to treat a myocardial infarction. A cross-linking functionality can be synthesized starting from a fluorinated molecule with an ethylene functionality as in FIG. 22. Bromine 2310 is added to a fluoronated molecule 2300. Reduced thiols rapidly replace the bromine groups forming a di-functional thiol component 2320. The di-functional thiol 2330 can then react with a tetra-acryloyl(polyethylene glycol) 2340 and a difunctional polyethylene glycol with both the thiol functionality and the RGD 2380 peptide sequence. The tetra-acryloyl(polyethylene glycol) can be obtained from Shearwater Polymers as a specialty polymer (product number 0J0000D04; $M_r$=2,000 with each arm having a molecular weight of 500 g/mol or ~15 PEG sequences long). It is generated by the reaction of the tetra-hydroxyl terminated polyethylene glycol and acryloyl in the presence of a tertiary amine.

The third component is a peptide binding sequence 2350 with a polyethylene glycol functionality. The polyethylene glycol spacer 2370 must be longer then the spacer functionality of the other two components to prevent steric hindrance of the matrix components and ensure bio-availability of the peptide binding sequence. In this mixture of these three components, the average functionality must be two or greater to ensure desired gel formation.

In order to use this component system for the treatment of an MI, an aliquot of acryloyl functionalities are diluted in water preferably with a basic pH. Then the aliquot is added to a syringe that feed a bore of a dual-bore needle (described previously). The thiol component is then added to a syringe that controls the second bore of the dual bore syringe. The two components with acryloyl functionalities and thiol functionalities are added simultaneously to the infarct region via the dual bore system or via a catheter. The components come in contact with one another at the site and form a gel network with a high oxygen carrying capability.

Example 2. Example 2 incorporates all of the components of Example 1 with an additional component. Adult skin cells capable of differentiating into cardiomyocytes are added to the second component, a perfluoronated compound. The cells may be injected along with the perfluoronated thiol. This would result in the formation of a hydrogel capable of supporting the oxygen demands of the cell. In addition the gel would swell by taking up fluids, provide nutrients for the cells and is capable of eliminating cellular wastes as well as serving as a cellular scaffold for deposition of the fibroblasts. Other sources of cells that could be delivered and survive may include but are not limited to adult, fetal and embryonic stems cells (eg meschenchymal, skeletal myoblast cells etc . . .

Example 3 illustrates the use of gel introduction to the infarct region of a deceased rat heart. Ex-vivo rat hearts were obtained and the hearts were mapped for the infarct region. Less than 30 microliters of material were injected into the infarct region. An agent 10% poly (allyl amine) hydrochloride 3.1 grams plus 35% poly(acrylic acid) 0.7 grams system is protonated, resulting in a stable aqueous solution was maintained at pH 3.0 within the catheter until it reached the targeted area. The solution was injected into 10% gelatin gel in phosphate-buffered saline. The injectate gels instantly. The same injectate was used on the ex-vivo rat heart. The injectate gelled instantly at the infarct region.

Example 4. Sprague-Dawley rats were infarcted by an open chest procedure, ligature on LAD. Survived for 7 days to allow scar formation, then sacrificed. (Charles River Labs) Hearts removed and packed in ice cold PBS.

The hearts were injected in infarct region by a 1 cc syringe, 30-gauge needle. The following polymers were used in the infarct region.

1. PLGA (poly lactic co-glycolic acid polymer, Birmingham Polymers), a 20% solution in Diglyme, with 0.6% Sudan Red B was introduced. It was injected into infarcted wall. The tissue swells immediately and then the solution precipitates in the infarct region.

2. Poly(butyl methacrylate co-methyl methacrylate. Mr=100,000 daltons (Aldrich), a 20% solution in Diglyme, with 1% Fat Brown RR. It was injected into infarcted wall. The tissue swells immediately and then the solution precipitates in the infarct region.

3. A 3.1 gram aliquot of a 10% solution of Poly allyl amine (Aldrich) was mixed with 0.7 grams of 35% Poly(acrylic acid) in water (Aldrich). In addition, 1% Toluidine blue was added to the solution. This composition was injected into infarcted wall. The tissue swells immediately and the solution precipitates.

Histology sections (10 micron sliced) demonstrated that the dyed polymers precipitated within the infarct tissue in the infarct region.

TABLE 1

| Compound | | Properties | | |
|---|---|---|---|---|
| | | | Vapor | |
| Trade Name or Common Name | Chemical Name and Structure | Molecular Weight | Pressure (mmHg) | $O_2$ solubility at 37° C. (V %) |
| F-44E | 1,2-bis(perfluorobutyl)ethane $F_9C_4$—CH=CH—$C_4F_9$ | 462 | 12.6 | 50 |
| F-66E or F-i66E | 1-perfluoropropane-2-perfluorohexyl)ethane $F_7C_3$—CH=CH—$C_6F_{13}$ | 664 | 2.3 | 41 |
| FDC | Perfluorodecalin $C_{10}F_{18}$ | 462 | 12.5 | 45 |

The invention claimed is:
1. A method, comprising:
delivering particles to a ventricle
wherein the particles carry at least one pro-fibroblastic agent;
delivering to the ventricle at least one of tropoelastin and a tropoelastin precursor; and
forming a scaffold in the ventricle to facilitate attachment of fibroblasts.
2. The method of claim 1, wherein said delivering the particles to the ventricle comprises delivering the particles to an infarct region of the ventricle, and wherein forming the scaffold comprises forming the scaffold at the infarct region.

3. The method of claim 1, wherein the particles comprise a dimension of 200 microns or less.

4. The method of claim 1, wherein the pro-fibroblastic agent is selected from at least one of basic fibroblast growth factor (bFGF), leukemia inhibitory factor (LIF), vascular endothelial growth factor (VEGF), tumor necrosis factor-alpha (TNF-α), platelet-derived growth factor-BB (PDGF-BB), angiogenin, angiopoietin-1, Del-1, follistatin, granulocyte colony-stimulating factor (G-CSF), pleiotrophin (PTN), proliferin, transforming growth factor-alpha (TGF-α), and vascular permeability factor (VPF).

5. The method of claim 4, wherein the pro-fibroblastic agent comprises at least one of bFGF, LIF and PDGF-BB.

6. The method of claim 1, further comprising delivering a swellable material to the ventricle wherein the swellable material is capable of fluid uptake.

7. The method of claim 1, wherein delivering the particles comprises introducing the particles to the ventricle through a minimally invasive procedure.

8. The method of claim 7, wherein the minimally invasive procedure is selected from at least one of sub-xiphoid, percutaneous, intercoronary infusion and open-chest procedure in conjunction with Coronary Artery Bypass Graft (CABG).

9. The method of claim 8, wherein the minimally invasive procedure comprises a percutaneous introduction of the particles, and wherein the percutaneous introduction of the particles comprises at least one of intra-ventricular catheter, transvascular needle catheter and retrograde venous perfusion.

10. The method of claim 1, further comprising increasing the compliance of the ventricle with the particles.

11. The method of claim 1, further comprising preventing thinning of the ventricle with the particles.

12. The method of claim 1, further comprising delivering an agent to encourage conversion of the fibroblasts to muscular cells.

13. The method of claim 1, wherein the particles comprise particles having at least one opsonin inhibitor.

14. The method of claim 1, wherein the scaffold is operable to remain in the ventricle for at least one week.

15. A method, comprising:
delivering particles to a ventricle
wherein the particles carry at least one pro-fibroblastic agent;
delivering to the ventricle at least one of tropoelastin and a tropoelastin precursor; forming a scaffold in the ventricle to facilitate attachment of fibroblasts; and
delivering to the ventricle a dispersing agent.

16. The method of claim 15, wherein the dispersing agent comprises a macromer solution of an oligomeric functional acrylate.

17. The method of claim 16, wherein the macromer solution of the oligomeric functional acrylate comprises at least one of diacryloyl polyethylene glycol (diacyryloyl PEG), tetraacryloyl polyethylene glycol, and (acrylamidomethyl) cellulose acetate proprionate.

18. The method of claim 17, wherein the macromer solution of the oligomeric functional acrylate comprises diacryloyl-PEG.

19. The method of claim 16, further comprising delivering a thiol-containing component wherein the thiol-containing component comprises at least two thiol-groups.

20. The method of claim 19, wherein the thiol-containing component comprises at least one of polycysteine oligomers and naturally occurring peptides.

21. The method of claim 19, further comprising generating an ester linkage with the oligomeric functional acrylate and the thiol-containing component.

22. A method, comprising:
delivering particles to a ventricle
wherein the particles carry at least one pro-fibroblastic agent;
delivering to the ventricle at least one of tropoelastin and a tropoelastin precursor; forming a scaffold in the ventricle to facilitate attachment of fibroblasts; and
locally delivering at least one matrix metalloproteinase inhibitor (MMPI).

23. A kit comprising:
a delivery lumen;
at least one agent to be delivered from the delivery lumen to a ventricle
wherein the at least one agent comprises particles carrying at least one pro-fibroblastic agent; and
at least one component selected from at least one of tropoelastin and tropoelastin precursor to form a scaffold in the ventricle to facilitate attachment of fibroblasts.

24. The kit of claim 23, wherein the at least one agent is to be delivered to an infarct region of the ventricle.

25. The kit of claim 23, wherein the pro-fibroblastic agent comprises at least one of basic fibroblast growth factor (bFGF), leukemia inhibitory factor (LIF), vascular endothelial growth factor (VEGF), tumor necrosis factor-alpha (TNF-α), platelet-derived growth factor-BB (PDGF-BB), angiogenin, angiopoietin-1, Del-1, follistatin, granulocyte colony-stimulating factor (G-CSF), pleiotrophin (PTN), proliferin, transforming growth factor-alpha (TGF-α), and vascular permeability factor (VPF).

26. The kit of claim 23, further comprising a delivery device.

27. The kit of claim 23, further comprising at least one matrix metalloproteinase inhibitor (MMPI).

28. A composition comprising:
a microparticle having at least one pro-fibroblastic agent;
a biocompatible functional acrylate; and
a reduced thiol-containing compound
wherein the composition is capable of forming a bioerodible matrix in a ventricle of a subject, wherein the biocompatible acrylate and the reduced thiol-containing compound are capable of forming ester linkages, and wherein the bioerodible matrix is operable to resist decomposition in the ventricle for at least one week.

29. The composition of claim 28, wherein the biocrodible microparticle comprises PLGA 50:50.

30. The composition of claim 28, wherein the biocompatible acrylate comprises di-acryloyl polyethylene glycol.

31. The composition of claim 28, wherein the reduced thiol-containing compound comprises poly-s-benzyl-L-cysteine.

32. A method of using the composition of claim 28 comprising forming the bioerodible matrix in an infarct region of the ventricle of the subject.

33. The composition of claim 28, further comprising an agent to encourage conversion of fibroblasts to muscular cells.

34. The composition of claim 28, wherein the particles comprise particles having at least one opsonin inhibitor.

* * * * *

UNITED STATES PATENT AND TRADEMARK OFFICE
CERTIFICATE OF CORRECTION

PATENT NO. : 7,641,643 B2 Page 1 of 1
APPLICATION NO. : 10/414767
DATED : January 5, 2010
INVENTOR(S) : Michal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1814 days.

Signed and Sealed this

Sixteenth Day of November, 2010

David J. Kappos
*Director of the United States Patent and Trademark Office*